United States Patent
Lesur et al.

(10) Patent No.: US 7,119,214 B2
(45) Date of Patent: Oct. 10, 2006

(54) THIO-SUBSTITUTED TRICYCLIC AND BICYCLIC AROMATIC METHANESULFINYL DERIVATIVES

(75) Inventors: Brigitte Lesur, Champs sur Marne (FR); Christophe Yue, Vincennes (FR); Sophie Chasset, Nandy (FR); Olivier Renault, Palaiseau (FR)

(73) Assignee: Cephalon France, Maisons-Alfort (FR)

( * ) Notice: Subject to any disclaimer, the term of this patent is extended or adjusted under 35 U.S.C. 154(b) by 0 days.

(21) Appl. No.: 11/103,951

(22) Filed: Apr. 12, 2005

(65) Prior Publication Data

US 2005/0282821 A1 Dec. 22, 2005

Related U.S. Application Data

(60) Provisional application No. 60/569,330, filed on May 7, 2004.

(30) Foreign Application Priority Data

Apr. 13, 2004 (EP) .................................. 04290980

(51) Int. Cl.
- C07D 307/91 (2006.01)
- C07D 409/12 (2006.01)
- C07D 413/12 (2006.01)
- C07D 401/12 (2006.01)
- C07D 207/00 (2006.01)
- A01N 43/08 (2006.01)

(52) U.S. Cl. ...................... 549/460; 514/468; 544/375; 544/153; 546/187; 548/525; 548/543; 548/568

(58) Field of Classification Search ................ 549/460; 514/468; 544/375, 153; 546/187; 548/525, 548/543, 568
See application file for complete search history.

(56) References Cited

U.S. PATENT DOCUMENTS

| | | | |
|---|---|---|---|
| 4,066,686 A | 1/1978 | Lafon | 260/500.5 |
| 4,177,290 A | 12/1979 | Lafon | 424/324 |
| 4,927,855 A | 5/1990 | Lafon | 514/618 |
| 4,935,240 A | 6/1990 | Nakai et al. | 424/400 |
| 4,980,372 A | 12/1990 | Nakai et al. | 514/510 |
| 5,180,745 A | 1/1993 | Lafon | 514/618 |
| 5,391,576 A | 2/1995 | Lafon, deceased | 514/618 |
| 5,401,776 A | 3/1995 | Laurent | 514/618 |
| 5,563,169 A | 10/1996 | Yoshida et al. | 514/454 |
| 5,612,379 A | 3/1997 | Laurent | 514/618 |
| 5,719,168 A | 2/1998 | Laurent | 514/357 |
| 6,346,548 B1 | 2/2002 | Miller et al. | 514/618 |
| 6,455,588 B1 | 9/2002 | Scammell et al. | 514/618 |
| 6,488,164 B1 | 12/2002 | Miller et al. | 214/618 |
| 6,492,396 B1 | 12/2002 | Bacon et al. | 514/332 |

FOREIGN PATENT DOCUMENTS

| | | |
|---|---|---|
| EP | 0 105 397 A1 | 4/1984 |
| EP | 0 121 716 A1 | 10/1984 |
| EP | 0 387 603 A1 | 9/1990 |
| EP | 1 136 477 A1 | 9/2001 |
| EP | 0 4290 980.4 | 4/2004 |
| EP | 1 411 052 A1 | 4/2004 |
| WO | WO 95/01171 A1 | 1/1995 |
| WO | WO 93/05033 A1 | 3/1995 |
| WO | WO 99/25329 A1 | 5/1999 |
| WO | WO 01/87830 A2 | 11/2001 |
| WO | WO 02/10125 A1 | 2/2002 |
| WO | WO 03/002531 A2 | 1/2003 |
| WO | WO 03/029212 A1 | 4/2003 |
| WO | WO 03/037853 A1 | 5/2003 |
| WO | WO2004/037805 A1 | 5/2004 |

OTHER PUBLICATIONS

Annis, I., et al., "Novel solid-phase reagents for facile formation of intramolecular disulfide bonds in peptides under mild conditions," *Pept. Proc. Am. Pept. Symp. 15th*, meeting dated 1997, 1999, 343-344.

Cagniant, P., et al., "Syntheses beginning with 2-chloromethylbenzo 'b! furan. 3,4-dihydro-1H-thieno '3,4-b!benzo'1!furan, 1H-thieno 3,4- b!benzo furan, and their derivatives and 6,12-dihydro-12-oxobenzothiepino '3,4-benzo'1!furan," *Chem. Abstracts Ser.*, Accession No. 72825, 1975, 2 pages.

Cagniant, P., "4,5!thieno 3,2-c!thiopyrans," *Chem. Abstracts Ser.*, Accession No. 420242, 1971, 1 page.

(Continued)

*Primary Examiner*—Kamal A. Saeed
*Assistant Examiner*—Yong Chu
(74) *Attorney, Agent, or Firm*—Woodcock Washburn LLP

(57) ABSTRACT

The present invention is related to chemical compositions, processes for the preparation thereof and uses of the composition. Particularly, the present invention relates to compositions of compounds of Formula (A):

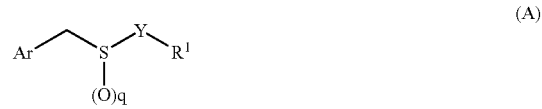

(A)

wherein Ar, Y, $R^1$ and q are as defined herein; and their use in the treatment of diseases, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder ("ADHD"), enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

19 Claims, No Drawings

OTHER PUBLICATIONS

Dzvinchuk, B., "Recyclization in hydration of 3-formyl-2-phenyl-1,4-benzodioxin," *Chem. Of Heterocy. Compds*, 1999, 35(10), 1480-1481.

Edgar, D.M., "CCD-3693: an orally bioavailable analog of the endogenous neuroactive steroid, pregnanolone, demonstrates potent sedative hypnotic actions in the rat," *J. of Pharmacol. & Exp. Ther.*, 1997, 282(1), 420-429.

Edgar, D.M., et al., "Modafinil induces wakefulness without intensifying motor activity or subsequent rebound hypersomnolence in the rat," *J. of Pharm. & Experi. Therap.*, 1997, 283, 757-769.

El-Sakka, I.A., et al., "Reactions with thiaxanthen-9-ol: new thiaxanthene derivatives with molluscicidal and nematocidal activity," *Arch. Pharm. (Weinheim)*, 1994, 327, 133-135.

Farina, G., "1,4-Benzodioxins from 1,4-Benzodioxans," *Synthesis*, 1977, p. 755.

Han, Y., et al., "Novel S-Xanthenyl protecting groups for cysteine and their applications for the $N^a$-9-fluorenylmethyloxcarbonyl (Fmoc) strategy of peptide synthesis," *Org. Chem.*, 1997, 62, 3841-3848.

Hermant, J.-F., et al., "Awakening properties of modafinil: effect on nocturnal activity in monkeys (*Macaca mulatta*) after acute and repeated adminstration," *Psychopharmacology*, 1991, 103, 28-32.

Imeri, L., et al., "Blockade of 5-hydroxytryptamine (serotonin)-receptors alters interleukin-1-induced changes in rat sleep," *Neurosci.*, 1999, 92(2), 745-749.

Lee, T.V., "Synthetic studies on 1,4-benzodioxin: the preparation of analogues of biologically important indoles," *Tetrahedron*, 1990, 46(3), 921-934 (abstract 1 page).

Lehninger, A.L., "The amino acid building blocks of proteins," *Biochemistry. 2nd Ed.*, Worth Publishers, NY, 1975, 71-77.

Lin, J.S., et al., "Role of catecholamines in the modafinil and amphetamine induced wakefulness, a comparative pharmacological study in the cat," *Brain Res.*, 1992, 591, 319-326.

Opp, M.R., et al., "Anti-interleukin-1β reduces sleep and sleep rebound after sleep deprivation in rats," *Am. J. of Physiol.*, 1994, R688-R695.

Opp, M.R., et al., "Rat strain differences suggest a role for corticotrophin-releasing hormone in modulating sleep," *Physiol. & Behav.*, 1998, 63(I), 67-74.

Panckeri, K.A., et al., "Modafinil decreases hypersomnolence in the English bulldog, a natural animal model of sleep-disordered breathing," *Sleep*, 1996, 19(8), 626-631.

Piotrowska, H., et al., "New sulfur derivatives of indole," *Chem. Abstracts Ser.*, Accession No. 494178, 1978, 2 pages.

Seidel, W.F., et al., "*Alpha*-2 adrenergic modulation of sleep: time-of-day dependent pharmacodynamic profiles of dexmedetomidine and clonidine in the rat," *J. of Pharmacol. Exp. Ther.*, 1995, 275(1), 263-273.

Shelton, J., et al., "Comparative effects of modafinil and amphetamine on daytime sleepiness and cataplexy of narcoleptic dogs," *Sleep*, 1995, 18(10), 817-826.

Terauchi, H., et al., "Nicotinamide derivatives as a new class of gastric $H^+/K^+$-ATPase inhibitors. 1. Synthesis and structure-activity relationships of N-substituted 2-(benzhydryl- and benzylsulfinyl)nicotinamides," *J. of Med. Chem.*, 1997, 40, 313-321.

Touret, M., et al., "Awakening properties of modafinil without paradoxical sleep rebound: comparative study with amphetamine in the rat," *Neurosc. Letts.*, 1995, 189, 43-46.

Van Gelder, R.N., et al., "Real-time automated sleep scoring: validation of a microcomputer-based system for mice," *Sleep*, 1991, 14(1), 48-55.

Welsh, D.K., et al., "A circadian rhythm of hippocampal theta activity in the mouse," *Physiol. & Behav.*, 1985, 35, 533-538.

THIO-SUBSTITUTED TRICYCLIC AND BICYCLIC AROMATIC METHANESULFINYL DERIVATIVES

CROSS-REFERENCE TO RELATED APPLICATIONS

This application claims priority of now abandoned U.S. Provisional Application Ser. No. 60/569,330, filed May 7, 2004 and European Patent Application No. 04290980.4, filed Apr. 13, 2004. The complete disclosures of these prior applications are incorporated herein by reference in their entireties for all purposes.

FIELD OF THE INVENTION

The present invention is related to chemical compositions, processes for the preparation thereof and uses of the composition. Particularly, the present invention relates to compositions of compounds of Formula (A):

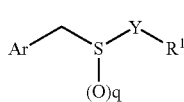

and their use in the treatment of diseases, including treatment of sleepiness, promotion and/or improvement of wakefulness, preferably improvement of wakefulness in patients with excessive sleepiness associated with narcolepsy, sleep apnea, preferably obstructive sleep apnea/hypopnea, and shift work disorder; treatment of Parkinson's disease; Alzheimer's disease; cerebral ischemia; stroke; eating disorders; attention deficit disorder ("ADD"), attention deficit hyperactivity disorder ("ADHD"); depression; schizophrenia; fatigue, preferably fatigue associated with cancer or neurological diseases, such as multiple sclerosis and chronic fatigue syndrome; stimulation of appetite and weight gain and improvement of cognitive dysfunction.

BACKGROUND OF THE INVENTION

The compounds disclosed herein are related to the biological and chemical analogs of modafinil. Modafinil, $C_{15}H_{15}NO_2S$, also known as 2-(benzhydrylsulfinyl)acetamide, or 2-[(diphenylmethyl)sulfinyl] acetamide, a synthetic acetamide derivative with wake-promoting activity, has been described in French Patent No. 78 05 510 and in U.S. Pat. No. 4,177,290 ("the '290 patent"). It has been approved by the United States Food and Drug Administration for use in the treatment of excessive daytime sleepiness associated with narcolepsy. Methods for preparing modafinil and several derivatives are described in the '290 patent. The levorotatory isomer of modafinil, along with additional modafinil derivatives are described in U.S. Pat. No. 4,927,855, and are reported to be useful for treatment of hypersomnia, depression, Alzheimer's disease and to have activity towards the symptoms of dementia and loss of memory, especially in the elderly.

Modafinil has also been described as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas and disorders of central origin (U.S. Pat. No. 5,612,379). In addition, modafinil may be used in the treatment of eating disorders, or to promote weight gain or stimulate appetite in humans or animals (U.S. Pat. No. 6,455,588), or in the treatment of attention deficit hyperactivity disorder (U.S. Pat. No. 6,346,548), or fatigue, especially fatigue associated with multiple sclerosis (U.S. Pat. No. 6,488,164). U.S. Pat. No. 4,066,686 describes various benzhydrylsulphinyl derivatives as being useful in therapy for treating disturbances of the central nervous system.

Several published patent applications describe derivative forms of modafinil and the use of modafinil derivatives in the treatment of various disorders. For example, PCT publication WO 99/25329 describes various substituted phenyl analogs of modafinil as being useful for treating drug-induced sleepiness, especially sleepiness associated with administration of morphine to cancer patients. U.S. Pat. No. 5,719,168 and PCT Publication No. 95/01171 describes modafinil derivatives that are useful for modifying feeding behavior. PCT Publication No. 02/10125 describes several modafinil derivatives of modafinil, along with various polymorphic forms of modafinil.

Additional publications describing modafinil derivatives include U.S. Pat. No. 6,492,396, and PCT Publication No. WO 02/10125.

Terauchi, H, et al. described nicotinamide derivatives useful as ATP-ase inhibitors (Terauchi, H, et al, *J. Med. Chem.*, 1997, 40, 313–321). In particular, several N-alkyl substituted 2-(Benzhydrylsulfinyl)nicotinamides are described.

U.S. Pat. Nos. 4,980,372 and 4,935,240 describe benzoylaminophenoxybutanoic acid derivatives. In particular, sulfide derivatives of modafinil containing a phenyl and substituted phenyl linker between the sulfide and carbonyl, and a substituted aryl in the terminal amide position, are disclosed.

Other modafinil derivatives have been disclosed wherein the terminal phenyl groups are constrained by a linking group. For example, in U.S. Pat. No. 5,563,169, certain xanthenyl and thiaxanthenyl derivatives having a substituted aryl in the terminal amide position are reported.

Other xanthenyl and thiaxanthenyl derivatives are disclosed in Annis, I; Barany, G. *Pept. Proc. Am. Pept. Symp.* 15th (Meeting Date 1997) 343–344, 1999 (preparation of a xanthenyl derivative of Ellman's Reagent, useful as a reagent in peptide synthesis); Han, Y.; Barany, G. *J. Org. Chem.*, 1997, 62, 3841–3848 (preparation of S-xanthenyl protected cysteine derivatives, useful as a reagent in peptide synthesis); and El-Sakka, I. A., et al. *Arch. Pharm. (Weinheim)*, 1994, 327, 133–135 (thiaxanthenol derivatives of thioglycolic acid).

Thus, there is a need for novel classes of compounds that possess the beneficial properties. It has been discovered that a class of compounds, referred to herein as substituted thioacetamides, are useful as agents for treating or preventing various diseases or disorders disclosed herein.

SUMMARY OF THE INVENTION

The present invention in one aspect is directed to various novel compounds of structure:

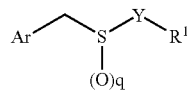

and its stereoisomeric forms, mixtures of stereoisomeric forms, or pharmaceutically acceptable salt forms thereof, wherein the constituent members are defined infra.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt or ester form thereof.

Another object of the present invention is to provide methods of treating or preventing diseases or disorders, including treatment of sleepiness, promotion and/or improvement of wakefulness, preferably improvement of wakefulness in patients with excessive sleepiness associated with narcolepsy, sleep apnea, preferably obstructive sleep apnea/hypopnea, and shift work disorder; treatment of Parkinson's disease; Alzheimer's disease; cerebral ischemia; stroke; eating disorders; attention deficit disorder ("ADD"), attention deficit hyperactivity disorder ("ADHD"); depression; schizophrenia; fatigue, preferably fatigue associated with cancer or neurological diseases, such as multiple sclerosis and chronic fatigue syndrome stimulation of appetite and weight gain and improvement of cognitive dysfunction.

These and other objects, features and advantages of the substituted benzylthioalkyl will be disclosed in the following detailed description of the patent disclosure.

DETAILED DESCRIPTION OF THE INVENTION

In a first embodiment, the present invention provides novel compounds of formula (A):

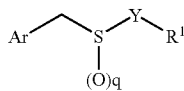

(A)

wherein:
Ar is:

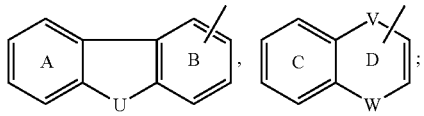

Wherein:
U is $CH_2$, $CR^{25}R^{26}$, O, $S(O)_y$, $NR^{10}$, C(=O), C(=S), CHOH, $CHOR^{14}$, $C=NOR^{14}$, or $C=NNR^{12}R^{13}$;

V and W are independently selected from a bond, $CH_2$, $CR^{25}R^{26}$, O, $S(O)_y$, $NR^{10}$, C(=O), C(=S), CHOH, $CHOR^{14}$, $C=NOR^{14}$, or $C=NNR^{12}R^{13}$;

rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1-C_6$ alkyl, $C_2-C_6$ alkenyl, $C_2-C_6$ alkynyl, $C_3-C_7$ cycloalkyl, 3–7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

ring D is optionally substituted with one group selected from $C_1-C_6$ alkyl, phenyl, and 5–10 membered heteroaryl;

Y is $C_1-C_6$alkylene; or
$(C_1-C_4$ alkylene$)_m$-Z-$(C_1-C_4$ alkylene$)_n$;
wherein said alkylene groups are optionally substituted with one to three $R^{20}$ groups;

Z is O, $NR^{10A}$, $S(O)_y$, $CR^{21}=CR^{21}$, C≡C, $C_6-C_{10}$ arylene, 5–10 membered heteroarylene, $C_3-C_6$ cycloalkylene, or 3–6 membered heterocycloalkylene; wherein said arylene, heteroarylene, cycloalkylene, and heterocycloalkylene groups are optionally substituted with one to three $R^{20}$ groups;

$R^1$ is selected from H, $NR^{12}R^{13}$, $NR^{21}C(=O)R^{14}$, C(=O)$R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, $NR^{21}S(O)_2R^{12}R^{13}$, and $C(=O)NR^{11}OR^{22}$;

$R^{10}$ and $R^{10A}$ are each independently selected from H, $C_1-C_6$ alkyl, $C_6-C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_1-C_6$ alkyl, and $C_6-C_{10}$ aryl; wherein said alkyl and aryl groups are optionally substituted with one to three $R^{20}$ groups;

$R^{12}$ and $R^{13}$ at each occurrence are each independently selected from H, $C_1-C_6$ alkyl, $C_6-C_{10}$ aryl, and $NR^{23}R^{24}$, or $R^{12}$ and $R^{13}$, together with the nitrogen to which they are attached, form a 3–7 membered heterocyclic ring; wherein said alkyl and aryl groups and heterocyclic ring are optionally substituted with one to three $R^{20}$ groups;

$R^{14}$ at each occurrence is independently selected from $C_1-C_6$ alkyl, $C_6-C_{10}$ aryl, and alkylaryl; wherein said alkyl, aryl and alkylaryl groups are optionally substituted with one to three $R^{20}$ groups;

$R^{20}$ at each occurrence is independently selected from F, Cl, Br, I, $OR^{22}$, $OR^{27}$, $NR^{23}R^{24}$, NHOH, $NO_2$, CN, $CF_3$, $C_1-C_6$ alkyl optionally substituted with OH, $C_2-C_6$ alkenyl, $C_2-C_6$ alkynyl, $C_3-C_7$ cycloalkyl, 3–7 membered heterocycloalkyl, phenyl, 5 or 6 membered heteroaryl, arylalkyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $NR^{21}CO_2R^{22}$, $OC(=O)NR^{23}R^{24}$, $NR^{21}C(=S)R^{22}$, and $S(O)_yR^{22}$;

$R^{21}$ at each occurrence is independently selected from H and $C_1-C_6$ alkyl;

$R^{22}$ at each occurrence is independently selected from H, $C_1-C_6$ alkyl optionally substituted with OH, arylalkyl and $C_6-C_{10}$ aryl;

$R^{23}$ and $R^{24}$ at each occurrence are each independently selected from H, $C_1-C_6$ alkyl, and $C_6-C_{10}$ aryl, or $R^{23}$ and $R^{24}$, together with the nitrogen to which they are attached, form a 3–7 membered heterocyclic ring optionally substituted with =O;

$R^{25}$ and $R^{26}$ at each occurrence are each independently selected from H, $C_1-C_6$ alkyl, and $C_6-C_{10}$ aryl, or $R^{25}$ and $R^{26}$, together with the carbon to which they are attached, form a 3–7 membered heterocyclic ring;

$R^{27}$ at each occurrence is independently the residue of an amino acid after the hydroxyl group of the carboxyl group is removed;

m is 0 or 1;
n is 0 or 1;
q is 0, 1, or 2;
y is 0, 1, or 2;

with the exclusion of the compounds wherein:
U is $CH_2$, $C(=O)$, $CH(CH_3)$, S or $C=NNHPh$; and
Y is $CH_2$; and
$R^1$ is H;

and with the exclusion of the compounds wherein:
U is $CH_2$; and
Y is $C_1$–$C_6$ alkylene optionally substituted with $C_1$–$C_6$ alkylene; and
$R^1$ is $CONH_2$, or $CO_2R^{11}$ with $R^{11}=H$ or $C_1$–$C_6$ alkyl;

and with the exclusion of the compounds:
3-[(methylthio)methyl]-2-phenyl-1H-inden-1-one
3-[(methylsulfinyl)methyl]-2-phenyl-1H-inden-1-one and the stereoisomeric forms, mixtures of stereoisomeric forms or pharmaceutically acceptable salts forms thereof.

Preferably, when V is a bond, and W is O, $S(O)_y$, or $NR^{10}$, ring D is substituted by a phenyl group.

In a second embodiment, the present invention provides novel compounds of formula (I):

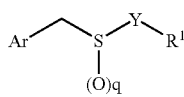
(I)

wherein
Ar is

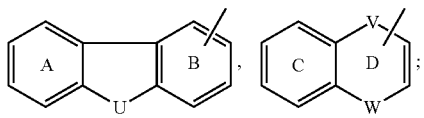

U is $CH_2$, $CR^{25}R^{26}$, O, $S(O)_y$, $NR^{10}$, $C(=O)$, $C(=S)$, CHOH, $CHOR^{14}$, $C=NOR^{14}$, or $C=NNR^{12}R^{13}$;

V and W are independently selected from a bond, $CH_2$, $CR^{25}R^{26}$, O, $S(O)_y$, $NR^{10}$, $C(=O)$, $C(=S)$, CHOH, $CHOR^{14}$, $C=NOR^{14}$, or $C=NNR^{12}R^{13}$;

rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1$–$C_6$ alkyl, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

ring D is optionally substituted with one group selected from $C_1$–$C_6$ alkyl, phenyl, and 5–10 membered heteroaryl;

Y is $C_1$–$C_6$ alkylene;
$(C_1$–$C_4$ alkylene$)_m$–$Z^1$–$(C_1$–$C_4$ alkylene$)_n$;
$C_1$–$C_4$ alkylene-$Z^2$–$C_1$–$C_4$ alkylene;
wherein said alkylene groups are optionally substituted with one to three $R^{20}$ groups;

$Z^1$ is $CR^{21}=CR^{21}$, $C\equiv C$, $C_6$–$C_{10}$ arylene, 5–10 membered heteroarylene, $C_3$–$C_6$ cycloalkylene, or 3–6 membered heterocycloalkylene; wherein said arylene, heteroarylene, cycloalkylene, and heterocycloalkylene groups are optionally substituted with one to three $R^{20}$ groups;

$Z^2$ is O, $NR^{10A}$, or $S(O)_y$;

$R^1$ is selected from H, $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})$ $NR^{12}R^{13}$, $OC(=O)NR^{12}R^{13}$, $NR^{21}S(O)_2R^{11}$, $NR^{21}C(=O)NR^{12}R^{13}$, $NR^{21}S(O)_2NR^{12}R^{13}$, and $C(=O)NR^{11}OR^{22}$;

$R^{10}$ and $R^{10A}$ are each independently selected from H, $C_1$–$C_6$ alkyl, $C_6$–$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_1$–$C_6$ alkyl, and $C_6$–$C_{10}$ aryl; wherein said alkyl and aryl groups are optionally substituted with one to three $R^{20}$ groups;

$R^{12}$ and $R^{13}$ at each occurrence are each independently selected from H, $C_1$–$C_6$ alkyl, $C_6$–$C_{10}$ aryl, and $NR^{23}R^{24}$, or $R^{12}$ and $R^{13}$, together with the nitrogen to which they are attached, form a 3–7 membered heterocyclic ring;
wherein said alkyl and aryl groups and heterocyclic ring are optionally substituted with one to three $R^{20}$ groups;

$R^{14}$ at each occurrence is independently selected from $C_1$–$C_6$ alkyl, $C_6$–$C_{10}$ aryl, and alkylaryl; wherein said alkyl, aryl and alkylaryl groups are optionally substituted with one to three $R^{20}$ groups;

$R^{20}$ at each occurrence is independently selected from F, Cl, Br, I, $OR^{22}$, $OR^{27}$, $NR^{23}R^{24}$, NHOH, $NO_2$, CN, $CF_3$, $C_1$–$C_6$ alkyl optionally substituted with OH, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, $=O$, $C(=O)R^{22}$, $CO_2R^{22}$, $OC(=O)R^{22}$, $C(=O)NR^{23}R^{24}$, $NR^{21}C(=O)R^{22}$, $NR^{21}$ $CO_2R^{22}$, $OC(=O)NR^{23}R^{24}$, $NR^{21}C(=S)R^{22}$, and $S(O)_yR^{22}$;

$R^{21}$ at each occurrence is independently selected from H and $C_1$–$C_6$ alkyl;

$R^{22}$ at each occurrence is independently selected from H, $C_1$–$C_6$ alkyl optionally substituted with OH, arylalkyl and $C_6$–$C_{10}$ aryl;

$R^{23}$ and $R^{24}$ at each occurrence are each independently selected from H, $C_1$–$C_6$ alkyl, and $C_6$–$C_{10}$ aryl, or $R^{23}$ and $R^{24}$, together with the nitrogen to which they are attached, form a 3–7 membered heterocyclic ring optionally substituted with $=O$;

$R^{25}$ and $R^{26}$ at each occurrence are each independently selected from H, $C_1$–$C_6$ alkyl, and $C_6$–$C_{10}$ aryl, or $R^{25}$ and $R^{26}$, together with the carbone to which they are attached, form a 3–7 membered heterocyclic ring;

$R^{27}$ at each occurrence is independently the residue of an amino acid after the hydroxyl group of the carboxyl group is removed;

m is 0 or 1;
n is 0 or 1;
q is 0, 1, or 2;
y is 0, 1, or 2;

and the stereoisomeric forms, mixtures of stereoisomeric forms or pharmaceutically acceptable salts forms thereof.

Preferably, when V is a bond, and W is O, $S(O)_y$, or $NR^{10}$, ring D is substituted by a phenyl group.

In another embodiment, the present invention includes a compound of formula (II):

(II)

wherein
Ar is:

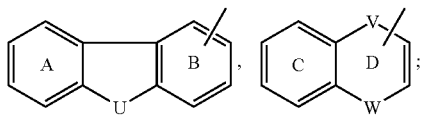

U is $CH_2$, O, $S(O)_y$, or $NR^{10}$;
V and W are independently selected from a bond, O, $S(O)_y$, or $NR^{10}$;
rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1$–$C_6$ alkyl, phenyl, arylalkyl, and $C(=O)R^{22}$;
ring D is optionally substituted with one group selected from $C_1$–$C_6$ alkyl, and phenyl;
Y is $C_1$–$C_6$ alkylene;
$C_1$–$C_4$ alkylene-$Z^1$-($C_1$–$C_4$ alkylene)$_n$;
$C_1$–$C_4$ alkylene-$Z^2$-$C_1$–$C_4$ alkylene;
wherein said alkylene groups are optionally substituted with one to three $R^{20}$ groups;
$Z^1$ is $CR^{21}$=$CR^{21}$, C≡C, $C_6$–$C_{10}$arylene, 5–10 membered heteroarylene, $C_3$–$C_6$ cycloalkylene, or 3–6 membered heterocycloalkylene; wherein said arylene, heteroarylene, cycloalkylene, and heterocycloalkylene groups are optionally substituted with one to three $R^{20}$ groups;
$Z^2$ is O, $NR^{10A}$, or $S(O)_y$;
$R^1$ is selected from $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$ $NR^{21}S(O)_2NR^{12}R^{13}$, and $C(=O)NR^{11}OR^{22}$;
$R^{10}$ and $R^{10A}$ are each independently selected from H, $C_1$–$C_6$ alkyl, $C(=O)R^{14}$, and $S(O)_yR^{14}$; wherein said alkyl and aryl groups are optionally substituted with one to three $R^{20}$ groups;
$R^{11}$ at each occurrence is independently selected from H, and $C_1$–$C_6$ alkyl; wherein said alkyl and aryl groups are optionally substituted with one to three $R^{20}$ groups;
$R^{12}$ and $R^{13}$ at each occurrence are each independently selected from H, and $C_1$–$C_6$ alkyl, and $NR^{23}R^{24}$, or $R^{12}$ and $R^{13}$, together with the nitrogen to which they are attached, form a 3–7 membered heterocyclic ring; wherein said alkyl and aryl groups and heterocyclic ring are optionally substituted with one to three $R^{20}$ groups;
$R^{14}$ at each occurrence is independently selected from $C_1$–$C_6$ alkyl and $C_6$–$C_{10}$ aryl; wherein said alkyl, aryl and alkylaryl groups are optionally substituted with one to three $R^{20}$ groups;
$R^{20}$ at each occurrence is independently selected from F, Cl, Br, I, $OR^{22}$, $OR^{27}$, $NR^{23}R^{24}$, NHOH, $NO_2$, CN, $CF_3$, $C_1$–$C_6$ alkyl optionally substituted with OH, phenyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
$R^{21}$ at each occurrence is independently selected from H and $C_1$–$C_6$ alkyl;
$R^{22}$ at each occurrence is independently selected from H. $C_1$–$C_6$ alkyl optionally substituted with OH, phenyl, and benzyl;
$R^{23}$ and $R^{24}$ at each occurrence are each independently selected from H, $C_1$–$C_6$ alkyl, and $C_6$–$C_{10}$aryl, or $R^{23}$ and $R^{24}$, together with the nitrogen to which they are attached, form a 3–7 membered heterocyclic ring optionally substituted with =O;

$R^{25}$ and $R^{26}$ at each occurrence are each independently selected from H, $C_1$–$C_6$ alkyl, and phenyl, or $R^{25}$ and $R^{26}$, together with the carbon to which they are attached, form a 3–7 membered heterocyclic ring;
$R^{27}$ at each occurrence is independently the residue of an amino acid after the hydroxyl group of the carboxyl group is removed;
n is 0 or 1;
q is 0, 1, or 2;
y is 0, 1, or 2;

and the stereoisomeric forms, mixtures of stereoisomeric forms or pharmaceutically acceptable salts forms thereof.

An additional aspect of the present invention includes compounds of formula (A) and formulas (I) and (II) wherein Y is $C_1$–$C_6$ alkylene, $C_1$–$C_4$ alkylene-$Z^1$-$C_1$–$C_4$ alkylene, or $C_1$–$C_4$ alkylene-$Z^2$-$C_1$–$C_4$ alkylene, wherein said alkylene groups are optionally substituted with one to three $C_1$–$C_6$ alkyl groups; $Z^1$ is $CR^{21}$=$CR^{21}$, C≡C, or phenyl; $Z^2$ is O, $NR^{10A}$, or $S(O)_y$; $R^1$ is selected from $NR^{21}C(=O)R^{14}$, $C(=O)R^{14}$, $CO_2R^{11}$, $OC(=O)R^{11}$, and $C(=O)NR^{12}R^{13}$. In other aspects, Y is $C_1$–$C_6$ alkylene, or $C_1$–$C_4$ alkylene-$Z^1$-$C_1$–$C_4$ alkylene. In additional aspects, Y is $C_1$–$C_6$ alkylene. In further aspects, $R^1$ is $C(=O)NR^{12}R^{13}$.

In certain aspects of the present invention, there are included compounds of formula (A) and formulas (I) and (II) wherein Ar is dibenzofuranyl. Other aspects include compounds where Ar is dibenzothienyl. Other aspects include compounds where Ar is fluorenyl. Other aspects include compounds where Ar is phenylbenzofuranyl. Other aspects include compounds where Ar is phenylbenzothiophenyl. Other aspects include compounds where Ar is phenylindolyl. Other aspects include compounds where Ar is phenylbenzodioxinyl.

In additional aspects of the present invention, there are included compounds of formula (A) and formulas (I) and (II) wherein Ar has any of the values of the previous embodiments and q is 1.

Other aspects of the present invention include compounds of formula (A) and formulas (I) and (II) wherein Ar and q have any of the values of the previous embodiments, and Y is $C_1$–$C_6$ alkylene, particularly those where Y is $CH_2$ or $CH_2CH_2$, and most particularly those where Y is $CH_2$.

Additional aspects of the present invention include compounds of formula (A) and formulas (I) and (II) wherein Ar and q have any of the values of the previous embodiments, and Y is ($C_1$–$C_4$ alkylene)$_m$-$Z^1$-($C_1$–$C_4$ alkylene)$_n$ wherein $Z^1$ is $CR^{21}$=$CR^{21}$, C≡C, $C_6$–$C_{10}$ arylene, 5–10 membered heteroarylene, $C_3$–$C_6$ cycloalkylene, or 3–6 membered heterocycloalkylene. Other aspects include those compounds where Y is $C_1$–$C_4$ alkylene-$Z^1$. Other aspects include those where Y is $Z^1$-$C_1$–$C_4$ alkylene. Additional aspects include compounds where Y is $C_1$–$C_4$ alkylene-$Z^1$-$C_1$–$C_4$ alkylene.

Further aspects of the present invention include compounds of formula (A) and formulas (I) and (II) wherein Ar, Y, and q have any of the values of the previous embodiments, and $Z^1$ is $CR^{21}$=$CR^{21}$, or C≡C. Other aspects include compounds where $Z^1$ is $C_6$–$C_{10}$ arylene, or $C_3$–$C_6$ cycloalkylene, particularly those where $Z^1$ is phenyl. Other aspects include compounds where $Z^1$ is 5–10 membered heteroarylene, or 3–6 membered heterocycloalkylene.

Further aspects of the present invention include compounds of formula (A) and formulas (I) and (II) wherein Ar and q have any of the values of the previous embodiments, and Y is ($C_1$–$C_4$ alkylene)$_m$-$Z^2$-($C_1$–$C_4$ alkylene)$_n$ wherein $Z^2$ is O, $NR^{10A}$, or $S(O)_y$. Other aspects include those compounds where Y is $C_1$–$C_4$ alkylene-$Z^2$, wherein $R^1$ cannot be H. Other aspects include those compounds where Y is $C_1$–$C_4$ alkylene-$Z^2$-$C_1$–$C_4$ alkylene. Additional aspects include any of the above embodiments of Y wherein $Z^2$ is O. Additional aspects include any of the above embodiments of Y wherein $Z^2$ is $NR^{10A}$.

Further aspects of the present invention include compounds of formula (A) and formulas (I) and (II) wherein Ar, Y, $Z^1$, and $Z^2$, and q have any of the values of the previous embodiments, and $R^1$ can be any value selected from the following 12 enumerated paragraphs:

1. H.
2. $NR^{12}R^{13}$.
3. $NR^{21}C(=O)R^{14}$.
4. $C(=O)R^{14}$.
5. $CO_2R^{11}$.
6. $OC(=O)R^{11}$.
7. $C(=O)NR^{12}R^{13}$.
8. $C(=NR^{11})NR^{12}R^{13}$.
9. $OC(=O)NR^{12}R^{13}$.
10. $NR^{21}S(O)_2R^{11}$.
11. $NR^{21}C(=O)NR^{12}R^{13}$.
12. $NR^{21}S(O)_2NR^{12}R^{13}$.
13. $C(=O)NR^{11}OR^{22}$.

Other additional aspects of the present invention include compounds of formula (A) and formulas (I) and (II) wherein Ar, Y, $Z^1$, and $Z^2$, and q have any of the values of the previous embodiments, and $R^1$ can be a combination of the values selected from the previous 13 enumerated paragraphs. The preceding 13 enumerated paragraphs may be combined to further define additional preferred embodiments of compounds of the present invention. For example, one such combination includes $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$, $C(=O)NR^{11}NR^{23}R^{24}$, $C(=O)NR^{11}OR^{22}$, and $C(=O)NR^{11}OR^{22}$.

Another such combination includes $NR^{12}R^{13}$, wherein $R^{12}$ and $R^{13}$ are each independently selected from H and $C_1$–$C_6$ alkyl; $NR^{21}C(=O)R^{14}$; $C(=O)NR^{12}R^{13}$; $C(=NR^{11})NR^{12}R^{13}$, and $NR^{21}C(=O)NR^{12}R^{13}$.

A third such combination includes $C(=O)R^{14}$, $CO_2R^{11}$, $OC(=O)R^{11}$, $C(=O)NR^{12}R^{13}$, $OC(=O)NR^{12}R^{13}$, $NR^{21}S(O)_2R^{11}$ and $NR^{21}S(O)_2NR^{12}R^{13}$.

A fourth such combination includes $NR^{21}C(=O)R^{14}$, $C(=O)R^{14}$, $CO_2R^{11}$, $OC(=O)R^{11}$, $C(=O)NR^{12}R^{13}$, and $C(=O)NR^{11}OR^{22}$.

A fifth such combination includes $NR^{21}C(=O)R^{14}$, and $C(=O)NR^{12}R^{13}$.

In still further aspects of the present invention, there are included compounds of formulas (III) and (IV):

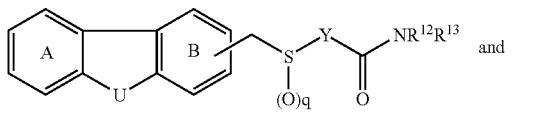

(III)

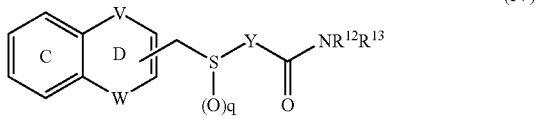

(IV)

wherein U, V and W have any of the values of the previous embodiments.

Additional aspects of the present invention include compounds of formula (A) and formulas (I) through (IV) wherein Ar, Y, $Z^1$, $Z^2$, $R^1$, and q have any of the values of the previous embodiments, and $R^{12}$ and $R^{13}$ are each independently selected from H and $C_1$–$C_6$ alkyl.

Other aspects of the present invention include compounds of formula (A) and formulas (I) through (IV) wherein Ar, Y, $Z^1$, $Z^2$, $R^1$, and q have any of the values of the previous embodiments, and $R^{12}$ and $R^{13}$ together with the nitrogen to which they are attached, form a 3–7 membered heterocyclic ring, particularly those where the heterocyclic ring is a heterocycloalkyl group, and more particularly those where the heterocyclic group is pyrrolidine or piperidine. In certain aspects, the heterocyclic ring is substituted with one $R^{20}$. In other aspects, the heterocyclic ring is unsubstituted.

In a preferred embodiment, Ar is dibenzofuranyl (U=O), dibenzothiophenyl (U=S) or fluorenyl (U=$CH_2$ or $CR^{25}R^{26}$).

Preferably, the ring A or B of such Ar groups is substituted with Cl, F or $OR^{22}$ wherein $R^{22}$ represents preferably a ($C_1$–$C_6$) alkyl group, such as a $OCH_3$ group.

In another preferred embodiment, Ar is benzofuranyl (W is a bond and V is O), benzothiophenyl (W is a bond and V is S), indol (W is a bond and V is N), or benzodioxinyl (W=V=O).

Preferably, the ring D of such Ar groups is substituted with a phenyl or Cl.

In accordance with a preferred embodiment, q is 0 or 1.

Preferably, Y is an unsubstituted ($C_1$–$C_6$) alkylene group, more preferably a $CH_2$ or $CH_2CH_2$ group and most preferably a $CH_2$ group.

In accordance with a preferred embodiment, $R^1$ is C(=O)$NR^{12}R^{13}$, wherein $R^{12}$ and $R^{13}$ independently represents H, $NR^{23}R^{24}$, ($C_1$–$C_6$) alkyl, or form a 3–7-membered heterocyclic ring together with the nitrogen atom to which they are attached.

In accordance with a preferred embodiment, $R^{12}$ and/or $R^{13}$ represent a $NR^{23}R^{24}$ wherein $R^{23}$ and $R^{24}$ together with the nitrogen to which they are attached, form a 3–7-membered heterocyclic ring, notably a 5–6-membered heterocyclic ring such as morpholine.

In accordance with another preferred embodiment, $R^{12}$ and/or $R^{13}$ represent a ($C_1$–$C_6$) alkyl group selected from methyl, ethyl, propyl, i-propyl, optionally substituted with one to three $R^{20}$ groups.

In that context, preferred substituents of $R^{12}$ and/or $R^{13}$ representing a ($C_1$–$C_6$) alkyl group are $OR^{22}$, $NR^{23}R^{24}$.

Examples of substituents $OR^{22}$ are notably OH and $O(C_1$–$C_6$) alkyl optionally substituted by OH such as $OCH_2CH_2OH$.

Examples of substituents $NR^{23}R^{24}$ are those wherein $R^{23}$ and $R^{24}$ together with the nitrogen to which they are attached, form a 3–7-membered heterocyclic ring, notably a 5–6-membered heterocyclic ring such as pyrrolidine, piperazine or morpholine, the pyrrolidine being optionally substituted by =O.

In accordance with another preferred embodiment, $R^{12}$ and/or $R^{13}$ form a 3–7-membered heterocyclic ring together with the nitrogen atom to which they are attached wherein the heterocyclic ring is preferably a 5–6-membered heterocyclic ring such as pyrrolidinyl, piperazinyl, piperidinyl or morpholinyl.

Heterocyclic ring may be substituted or unsubstituted.

Preferred heterocyclic ring substituents are $OR^{22}$, =O, $C(=O)R^{22}$, $CO_2R^{22}$, $C(=O)NR^{23}R^{24}$, ($C_1$–$C_6$) alkyl optionally substituted with one to three OH.

Examples of substituents $OR^{22}$ are notably OH.

Examples of substituents $C(=O)R^{22}$ are notably those wherein $R^{22}$ is H or a $(C_1-C_6)$ alkyl group, such as $C(=O)H$ or $C(=O)CH_3$.

Examples of substituents $CO_2R^{22}$ are notably those wherein $R^{22}$ is $(C_1-C_6)$ alkyl or arylalkyl such as $CO_2tBu$, $CO_2Et$ and $CO_2CH_2Ph$.

Examples of $C(=O)NR^{23}R^{24}$ substituents are notably those wherein $R^{23}$ and $R^{24}$ independently represent H or $(C_1-C_6)$ alkyl such as $C(=O)NH_2$, $C(=O)N(CH_3)_2$, $C(=O)NH(iPr)$, or those wherein $R^{23}$ and $R^{24}$, together with the nitrogen to which they are attached, form a 3–7-membered heterocyclic ring, notably a 5–6-membered heterocyclic ring such as pyrrolidine.

Examples of $(C_1-C_6)$ alkyl groups substituted with one to three $R^{20}$ groups are notably methyl, ethyl, propyl, —$CH_2CH_2CH_2OH$.

In a preferred embodiment of the present invention there are provided compounds of formula (A) and formula (I):

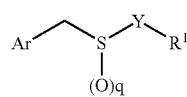

(I)

wherein Ar, q, Y—$R^1$ are defined in the table 1 below.

The positions on the Ar groups are numbered as follows:

TABLE 1

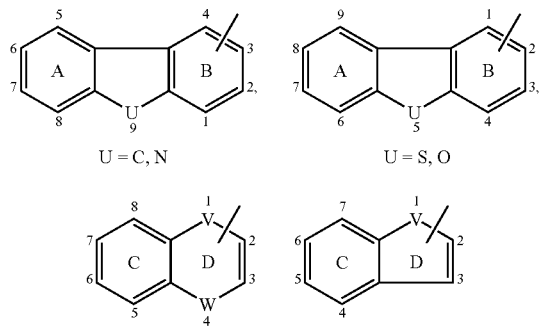

| Ex. n° | Ring Ar | q | Y—$R^1$ |
|---|---|---|---|
| 16 | Dibenzofuran-2-yl | 0 | $CH_2CONH_2$ |
| 36 | Dibenzofuran-2-yl | 1 | $CH_2CONH_2$ |
|  | Dibenzofuran-2-yl | 0 | $CH_2CON(CH_3)_2$ |
| 54 | Dibenzofuran-2-yl | 1 | $CH_2CON(CH_3)_2$ |
|  | Dibenzofuran-2-yl | 0 | $CH_2CO$—N-pyrrolidinyl |
| 55 | Dibenzofuran-2-yl | 1 | $CH_2CO$—N-pyrrolidinyl |
|  | Dibenzofuran-2-yl | 0 | $CH_2CONHCH(CH_3)_2$ |
| 56 | Dibenzofuran-2-yl | 1 | $CH_2CONHCH(CH_3)_2$ |
|  | Dibenzofuran-2-yl | 0 | $CH_2CO$-1-(4-tert-butoxycarbonyl)-piperazinyl |
| 57 | Dibenzofuran-2-yl | 1 | $CH_2CO$-1-piperazinyl |
|  | Dibenzofuran-2-yl | 0 | $CH_2CO$-1-(4-acetyl)-piperazinyl |
| 58 | Dibenzofuran-2-yl | 1 | $CH_2CO$-1-(4-acetyl)-piperazinyl |
|  | Dibenzofuran-2-yl | 0 | $CH_2CONHCH_2CH_2OH$ |
| 59 | Dibenzofuran-2-yl | 1 | $CH_2CONHCH_2CH_2OH$ |
|  | Dibenzofuran-2-yl | 0 | $CH_2CO$-1-(4-hydroxy)piperidinyl |
| 60 | Dibenzofuran-2-yl | 1 | $CH_2CO$-1-(4-hydroxy)piperidinyl |
|  | Dibenzofuran-2-yl | 0 | $CH_2CONHCH_2CH_2OCH_2CH_2OH$ |
| 61 | Dibenzofuran-2-yl | 1 | $CH_2CONHCH_2CH_2OCH_2CH_2OH$ |
| 15 | Dibenzofuran-2-yl | 0 | $CH_2CO$-1-[4-(2-hydroxyethyl)-piperazinyl] |
| 34 | Dibenzofuran-2-yl | 1 | $CH_2CO$-1-[4-(2-hydroxyethyl)-piperazinyl] |
|  | Dibenzofuran-2-yl | 0 | $CH_2CO$-1-(4-formyl)-piperazinyl |
| 62 | Dibenzofuran-2-yl | 1 | $CH_2CO$-1-(4-formyl)-piperazinyl |
| 63 | Dibenzofuran-2-yl | 1 | $CH_2CO$-1-(4-tert-butoxycarbonyl)-piperazinyl |
| 35 | Dibenzofuran-2-yl | 1 | $CH_2CO$-1-(4-ethoxycarbonyl)-piperazinyl |
| 64 | Dibenzofuran-2-yl | 1 | $CH_2CO$-1-(4-methyl)-piperazinyl |
|  | Dibenzofuran-2-yl | 0 | $CH_2CO$-1-(4-ethyl)-piperazinyl |
| 65 | Dibenzofuran-2-yl | 1 | $CH_2CO$-1-(4-ethyl)-piperazinyl |
|  | Dibenzofuran-2-yl | 0 | $CH_2CO$-1-(4-propyl)-piperazinyl |
| 66 | Dibenzofuran-2-yl | 1 | $CH_2CO$-1-(4-propyl)-piperazinyl |
|  | Dibenzofuran-2-yl | 0 | $CH_2CON$-morpholinyl |
| 67 | Dibenzofuran-2-yl | 1 | $CH_2CON$-morpholinyl |
|  | Dibenzofuran-2-yl | 0 | $CH_2CO$—N-ethyl-N-(2-hydroxy-ethyl) |
| 68 | Dibenzofuran-2-yl | 1 | $CH_2CO$—N-ethyl-N-(2-hydroxy-ethyl) |
|  | Dibenzofuran-2-yl | 0 | $CH_2CONHN$-morpholinyl |
| 69 | Dibenzofuran-2-yl | 1 | $CH_2CONHN$-morpholinyl |
|  | Dibenzofuran-2-yl | 0 | $CH_2CO$-4-(2-oxo-piperazinyl) |
| 70 | Dibenzofuran-2-yl | 1 | $CH_2CO$-4-(2-oxo-piperazinyl) |
| 71 | Dibenzofuran-2-yl | 1 | $CH_2CO$-1-(4-isopropylamino-carbonyl)-piperazinyl |
| 72 | Dibenzofuran-2-yl | 1 | $CH_2CO$-1-(4-aminocarbonyl)-piperazinyl |
| 73 | Dibenzofuran-2-yl | 1 | $CH_2CO$-1-(4-pyrrolidinyl-carbonyl)-piperazinyl |
| 74 | Dibenzofuran-2-yl | 1 | $CH_2CO$-1-(4-dimethylamino-carbonyl)-piperazinyl |
| 75 | Dibenzofuran-2-yl | 1 | $CH_2CO$-1-(4-benzyloxycarbonyl)-piperazinyl |
|  | Dibenzofuran-2-yl | 0 | $CH_2CH_2CONH_2$ |
| 76 | Dibenzofuran-2-yl | 1 | $CH_2CH_2CONH_2$ |
|  | Dibenzofuran-2-yl | 0 | $CH_2CH_2CO$-1-piperazinyl-N-Boc |
| 77 | Dibenzofuran-2-yl | 1 | $CH_2CH_2CO$-1-piperazinyl |
| 78 | Dibenzofuran-2-yl | 1 | $CH_2CH_2CO$-1-(4-acetyl)-piperazinyl |
| 79 | Dibenzofuran-2-yl | 1 | $CH_2CON$-3-(2-oxo-pyrrolidin-1-yl)-propyl] |
|  | Dibenzofuran-2-yl | 0 | $CH_2CON$-(2-pyrrolidin-1-yl-ethyl) |
| 80 | Dibenzofuran-2-yl | 1 | $CH_2CON$-(2-pyrrolidin-1-yl-ethyl) |
|  | Dibenzofuran-2-yl | 0 | $CH_2CON$-(2-piperidin-1-yl-ethyl) |
| 81 | Dibenzofuran-2-yl | 1 | $CH_2CON$-(2-piperidin-1-yl-ethyl) |
|  | Dibenzofuran-2-yl | 0 | $CH_2CON$-(2-morpholin-4-yl-ethyl) |
| 82 | Dibenzofuran-2-yl | 1 | $CH_2CON$-(2-morpholin-4-yl-ethyl |
|  | Dibenzofuran-2-yl | 0 | H |
| 83 | Dibenzofuran-2-yl | 1 | H |
|  | 6-Chloro-dibenzofuran-2-yl | 0 | $CH_2CO$-1-piperazinyl-N-Boc |
| 84 | 6-Chloro-dibenzofuran-2-yl | 1 | $CH_2CO$-1-piperazinyl |
|  | 6-Chloro-dibenzofuran-2-yl | 0 | $CH_2CO$-1-(4-acetyl)-piperazinyl |
| 85 | 6-Chloro-dibenzofuran-2-yl | 1 | $CH_2CO$-1-(4-acetyl)-piperazinyl |
| 22 | 8-Chloro-dibenzofuran-2-yl | 0 | $CH_2CO$-1-piperazinyl-N-Boc |
| 41 | 8-Chloro-dibenzofuran-2-yl | 1 | $CH_2CO$-1-piperazinyl |
|  | 8-Chloro-dibenzofuran-2-yl | 0 | $CH_2CONH_2$ |
| 86 | 8-Chloro-dibenzofuran-2-yl | 1 | $CH_2CONH_2$ |
| 23 | 8-Chloro-dibenzofuran-2-yl | 0 | $CH_2CO$-1-(4-acetyl)-piperazinyl |
| 42 | 8-Chloro-dibenzofuran-2-yl | 1 | $CH_2CO$-1-(4-acetyl)-piperazinyl |
| 146 | 8-Chloro-dibenzofuran-2-yl | 2 | $CH_2CO$-1-(4-acetyl)-piperazinyl |
| 21 | 8-Chloro-dibenzofuran-2-yl | 0 | $CH_2CO$-1-(4-hydroxyethyl)-piperazinyl |
| 40 | 8-Chloro-dibenzofuran-2-yl | 1 | $CH_2CO$-1-(4-hydroxyethyl)-piperazinyl |
| 17 | 8-Methoxy-dibenzofuran-2-yl | 0 | $CH_2CONH_2$ |
| 37 | 8-Methoxy-dibenzofuran-2-yl | 1 | $CH_2CONH_2$ |
|  | 8-Methoxy-dibenzofuran-2-yl | 0 | $CH_2CO$-1-piperazinyl-N-Boc |

TABLE 1-continued

| # | Ar | n | R |
|---|---|---|---|
| 87 | 8-Methoxy-dibenzofuran-2-yl | 1 | $CH_2CO$-1-piperazinyl |
|  | 8-Methoxy-dibenzofuran-2-yl | 0 | $CH_2CO$-1-4-acetyl)-piperazinyl |
| 88 | 8-Methoxy-dibenzofuran-2-yl | 1 | $CH_2CO$-1-(4-acetyl)-piperazinyl |
| 26 | 8-Fluoro-dibenzofuran-2-yl | 0 | $CH_2CO$-1-piperazinyl-N-Boc |
| 45 | 8-Fluoro-dibenzofuran-2-yl | 1 | $CH_2CO$-1-piperazinyl |
|  | 8-Fluoro-dibenzofuran-2-yl | 0 | $CH_2CO$-1-(4-acetyl)-piperazinyl |
| 89 | 8-Fluoro-dibenzofuran-2-yl | 1 | $CH_2CO$-1-(4-acetyl)-piperazinyl |
| 19 | 8-Fluoro-dibenzofuran-2-yl | 0 | $CH_2CONH_2$ |
| 38 | 8-Fluoro-dibenzofuran-2-yl | 1 | $CH_2CONH_2$ |
|  | 4-Chloro-dibenzofuran-2-yl | 0 | $CH_2CONH_2$ |
| 90 | 4-Chloro-dibenzofuran-2-yl | 1 | $CH_2CONH_2$ |
|  | 4-Fluoro-dibenzofuran-2-yl | 0 | $CH_2CONH_2$ |
| 91 | 4-Fluoro-dibenzofuran-2-yl | 1 | $CH_2CONH_2$ |
|  | 4-Chloro-dibenzofuran-2-yl | 0 | $CH_2CO$-1-(4-acetyl)-piperazinyl |
| 92 | 4-Chloro-dibenzofuran-2-yl | 1 | $CH_2CO$-1-(4-acetyl)-piperazinyl |
|  | 4-Fluoro-dibenzofuran-2-yl | 0 | $CH_2CO$-1-(4-acetyl)-piperazinyl |
| 93 | 4-Fluoro-dibenzofuran-2-yl | 1 | $CH_2CO$-1-(4-acetyl)-piperazinyl |
|  | 4-Fluoro-8-chloro-dibenzofuran-2-yl | 0 | $CH_2CONH_2$ |
| 94 | 4-Fluoro-8-chloro-dibenzofuran-2-yl | 1 | $CH_2CONH_2$ |
|  | Dibenzofuran-4-yl | 0 | $CH_2CONHCH_2CH_2OH$ |
| 95 | Dibenzofuran-4-yl | 1 | $CH_2CONHCH_2CH_2OH$ |
|  | Dibenzofuran-4-yl | 0 | $CH_2CONH_2$ |
| 96 | Dibenzofuran-4-yl | 1 | $CH_2CONH_2$ |
|  | Dibenzofuran-4-yl | 0 | $CH_2CO$-1-(4-acetyl)-piperazinyl |
| 97 | Dibenzofuran-4-yl | 1 | $CH_2CO$-1-(4-acetyl)-piperazinyl |
|  | Dibenzofuran-4-yl | 0 | $CH_2CO$-1-(4-hydroxy)piperidinyl |
| 98 | Dibenzofuran-4-yl | 1 | $CH_2CO$-1-(4-hydroxy)piperidinyl |
|  | Dibenzofuran-4-yl | 0 | $CH_2CO$-1-piperazinyl-N-Boc |
| 99 | Dibenzofuran-4-yl | 1 | $CH_2CO$-1-piperazinyl |
|  | Dibenzofuran-4-yl | 0 | $CH_2CON$-(2-pyrrolidin-1-yl-ethyl) |
| 100 | Dibenzofuran-4-yl | 1 | $CH_2CON$-(2-pyrrolidin-1-yl-ethyl) |
|  | Dibenzofuran-4-yl | 0 | $CH_2CON$-[3-(2-oxo-pyrrolidin-1-yl)-propyl] |
| 101 | Dibenzofuran-4-yl | 1 | $CH_2CON$-[3-(2-oxo-pyrrolidin-1-yl)-propyl] |
|  | Dibenzofuran-4-yl | 0 | $CH_2CON$-(2-piperidin-1-yl-ethyl) |
| 102 | Dibenzofuran-4-yl | 1 | $CH_2CON$-(2-piperidin-1-yl-ethyl) |
|  | Dibenzofuran-4-yl | 0 | $CH_2CON$-(2-morpholin-4-yl-ethyl) |
| 103 | Dibenzofuran-4-yl | 1 | $CH_2CON$-(2-morpholin-4-yl-ethyl) |
|  | Dibenzofuran-4-yl | 0 | $CH_2CO$-1-(4-hydroxyethyl)-piperazinyl |
| 104 | Dibenzofuran-4-yl | 1 | $CH_2CO$-1-(4-hydroxyethyl)-piperazinyl |
|  | Dibenzofuran-3-yl | 0 | $CH_2CO$-1-piperazinyl-N-Boc |
| 105 | Dibenzofuran-3-yl | 1 | $CH_2CO$-1-piperazinyl |
|  | Dibenzofuran-1-yl | 0 | $CH_2CO$-1-piperazinyl-N-Boc |
| 106 | Dibenzofuran-1-yl | 1 | $CH_2CO$-1-piperazinyl |
|  | Dibenzofuran-3-yl | 0 | $CH_2CO$-1-(4-acetyl)-piperazinyl |
| 107 | Dibenzofuran-3-yl | 1 | $CH_2CO$-1-(4-acetyl)-piperazinyl |
| 25 | Dibenzothiophen-2-yl | 0 | $CH_2CO$-1-piperazinyl-N-Boc |
| 44 | Dibenzothiophen-2-yl | 1 | $CH_2CO$-1-piperazinyl |
|  | Dibenzothiophen-2-yl | 0 | $CH_2CO$-1-(4-acetyl)-piperazinyl |
| 108 | Dibenzothiophen-2-yl | 1 | $CH_2CO$-1-(4-acetyl)-piperazinyl |
|  | Dibenzothiophen-2-yl | 0 | $CH_2CO$-1-(4-ethoxycarbonyl)-piperazinyl |
| 109 | Dibenzothiophen-2-yl | 1 | $CH_2CO$-1-(4-ethoxycarbonyl)-piperazinyl |
| 18 | Dibenzothiophen-2-yl | 0 | $CH_2CONH_2$ |
| 39 | Dibenzothiophen-2-yl | 1 | $CH_2CONH_2$ |
|  | Dibenzothiophen-4-yl | 0 | $CH_2CO$-1-(4-acetyl)-piperazinyl |
| 110 | Dibenzothiophen-4-yl | 1 | $CH_2CO$-1-(4-acetyl)-piperazinyl |
|  | Fluoren-1-yl | 0 | $CH_2CONHCH_2CH_2OH$ |
| 111 | Fluoren-1-yl | 1 | $CH_2CONHCH_2CH_2OH$ |
|  | Fluoren-1-yl | 0 | $CH_2CO$-1-(4-acetyl)-piperazinyl |
| 112 | Fluoren-1-yl | 1 | $CH_2CO$-1-(4-acetyl)-piperazinyl |
|  | Fluoren-1-yl | 0 | $CH_2CO$-1-(4-hydroxy)piperidinyl |
| 113 | Fluoren-1-yl | 1 | $CH_2CO$-1-(4-hydroxy)piperidinyl |
|  | Fluoren-1-yl | 0 | $CH_2CONH_2$ |
| 114 | Fluoren-1-yl | 1 | $CH_2CONH_2$ |
|  | Fluoren-1-yl | 0 | $CH_2CO$-1-(4-hydroxyethyl)-piperazinyl |
| 115 | Fluoren-1-yl | 1 | $CH_2CO$-1-(4-hydroxyethyl)-piperazinyl |
|  | Fluoren-1-yl | 0 | $CH_2CO$-1-piperazinyl-N-Boc |
| 116 | Fluoren-1-yl | 1 | $CH_2CO$-1-piperazinyl |
|  | Fluoren-2-yl | 0 | $CH_2CONH_2$ |
| 117 | Fluoren-2-yl | 1 | $CH_2CONH_2$ |
|  | Fluoren-2-yl | 0 | $CH_2CON(CH_3)_2$ |
| 118 | Fluoren-2-yl | 1 | $CH_2CON(CH_3)_2$ |
|  | Fluoren-2-yl | 0 | $CH_2CO$—N-pyrrolidinyl |
| 119 | Fluoren-2-yl | 1 | $CH_2CO$—N-pyrrolidinyl |
|  | Fluoren-2-yl | 0 | $CH_2CONHCH(CH_3)_2$ |
| 120 | Fluoren-2-yl | 1 | $CH_2CONHCH(CH_3)_2$ |
|  | Fluoren-2-yl | 0 | $CH_2CONHCH_2CH_2OH$ |
| 121 | Fluoren-2-yl | 1 | $CH_2CONHCH_2CH_2OH$ |
|  | Fluoren-2-yl | 0 | $CH_2CO$-1-(4-hydroxy)piperidinyl |
| 122 | Fluoren-2-yl | 1 | $CH_2CO$-1-(4-hydroxy)piperidinyl |
|  | Fluoren-2-yl | 0 | $CH_2CO$-1-(4-acetyl)-piperazinyl |
| 123 | Fluoren-2-yl | 1 | $CH_2CO$-1-(4-acetyl)-piperazinyl |
|  | Fluoren-4-yl | 0 | $CH_2CONH_2$ |
| 124 | Fluoren-4-yl | 1 | $CH_2CONH_2$ |
|  | Fluoren-4-yl | 0 | $CH_2CON(CH_3)_2$ |
| 125 | Fluoren-4-yl | 1 | $CH_2CON(CH_3)_2$ |
|  | Fluoren-4-yl | 0 | $CH_2CONHCH(CH_3)_2$ |
| 126 | Fluoren-4-yl | 1 | $CH_2CONHCH(CH_3)_2$ |
|  | Fluoren-4-yl | 0 | $CH_2CONHCH_2CH_2OH$ |
| 127 | Fluoren-4-yl | 1 | $CH_2CONHCH_2CH_2OH$ |
|  | Fluoren-4-yl | 0 | $CH_2CO$-1-(4-hydroxy)piperidinyl |
| 128 | Fluoren-4-yl | 1 | $CH_2CO$-1-(4-hydroxy)piperidinyl |
|  | Fluoren-4-yl | 0 | $CH_2CO$-1-(4-acetyl)-piperazinyl |
| 129 | Fluoren-4-yl | 1 | $CH_2CO$-1-(4-acetyl)-piperazinyl |
|  | Fluoren-4-yl | 0 | $CH_2CO$-1-piperazinyl-N-Boc |
| 130 | Fluoren-4-yl | 1 | $CH_2CO$-1-piperazinyl |
| 24 | Fluoren-4-yl | 0 | $CH_2CO$-1-(4-hydroxyethyl)-piperazinyl |
| 43 | Fluoren-4-yl | 1 | $CH_2CO$-1-(4-hydroxyethyl)-piperazinyl |
|  | Fluoren-4-yl | 0 | $CH_2CO$-1-(4-formyl)-piperazinyl |
| 131 | Fluoren-4-yl | 1 | $CH_2CO$-1-(4-formyl)-piperazinyl |
|  | 2-Phenylbenzofuran-3-yl | 0 | $CH_2CONH_2$ |
| 132 | 2-Phenylbenzofuran-3-yl | 1 | $CH_2CONH_2$ |
|  | 2-Phenylbenzofuran-3-yl | 0 | $CH_2CO$—N-pyrrolidinyl |
| 133 | 2-Phenylbenzofuran-3-yl | 1 | $CH_2CO$—N-pyrrolidinyl |
|  | 2-Phenylbenzofuran-3-yl | 0 | $CH_2CH_2CONH_2$ |
| 134 | 2-Phenylbenzofuran-3-yl | 1 | $CH_2CH_2CONH_2$ |
|  | 2-Phenylbenzofuran-3-yl | 0 | $CH_2CH_2CO$—N-pyrrolidinyl |
| 135 | 2-Phenylbenzofuran-3-yl | 1 | $CH_2CH_2CO$—N-pyrrolidinyl |
| 20 | 2-Phenylbenzofuran-3-yl | 0 | $CH_2CON(CH_3)_2$ |
| 46 | 2-Phenylbenzofuran-3-yl | 1 | $CH_2CON(CH_3)_2$ |
|  | 2-Phenylbenzofuran-3-yl | 0 | $CH_2CH_2CON(CH_3)_2$ |
| 136 | 2-Phenylbenzofuran-3-yl | 1 | $CH_2CH_2CON(CH_3)_2$ |
|  | 2-Phenylbenzofuran-3-yl | 0 | $CH_2CONHCH(CH_3)_2$ |
| 137 | 2-Phenylbenzofuran-3-yl | 1 | $CH_2CONHCH(CH_3)_2$ |
|  | 2-Phenylbenzofuran-3-yl | 0 | $CH_2CH_2CONHCH(CH_3)_2$ |
| 138 | 2-Phenylbenzofuran-3-yl | 1 | $CH_2CH_2CONHCH(CH_3)_2$ |
|  | 2-Phenylbenzofuran-3-yl | 0 | $CH_2CO$-1-(4-acetyl)-piperazinyl |
| 139 | 2-Phenylbenzofuran-3-yl | 1 | $CH_2CO$-1-(4-acetyl)-piperazinyl |
|  | 2-Phenylbenzofuran-3-yl | 0 | $CH_2CH_2CO$-1-(4-acetyl)-piperazinyl |
| 140 | 2-Phenylbenzofuran-3-yl | 1 | $CH_2CH_2CO$-1-(4-acetyl)-piperazinyl |
|  | 3-Phenylbenzothiophen-2-yl | 0 | $CH_2CONH_2$ |
| 141 | 3-Phenylbenzothiophen-2-yl | 1 | $CH_2CONH_2$ |
| 27 | 3-phenylbenzothiophen-2-yl | 0 | CH2-CO—N-pyrrolidinyl |

TABLE 1-continued

| | | | |
|---|---|---|---|
| 28 | 3-phenylbenzothiophen-2-yl | 0 | CH2-CON(CH$_3$)$_2$ |
| 29 | 3-phenylbenzothiophen-2-yl | 0 | CH2-CONHCH(CH$_3$)$_2$ |
| 30 | 3-phenylbenzothiophen-2-yl | 0 | CH2-CO-1-(4-hydroxy)-piperidinyl |
| 31 | 3-phenylbenzothiophen-2-yl | 0 | CH2-CO-1-(4-acetyl)-piperazinyl |
| 32 | 3-phenylbenzothiophen-2-yl | 0 | CH2-CONH(CH$_2$)$_2$OH |
| 47 | 3-phenylbenzothiophen-2-yl | 1 | CH2-CO—N-pyrrolidinyl |
| 48 | 3-phenylbenzothiophen-2-yl | 1 | CH2-CON(CH$_3$)$_2$ |
| 49 | 3-phenylbenzothiophen-2-yl | 1 | CH2-CONHCH(CH$_3$)$_2$ |
| 50 | 3-phenylbenzothiophen-2-yl | 1 | CH2-CO-1-(4-hydroxy)-piperidinyl |
| 51 | 3-phenylbenzothiophen-2-yl | 1 | CH2-CO-1-(4-acetyl)-piperazinyl |
| 52 | 3-phenylbenzothiophen-2-yl | 1 | CH2-CONH(CH$_2$)$_2$OH |
| 33 | 3-phenyl-1,4-benzodioxin-2-yl | 0 | CH$_2$CO-1-(4-acetyl)-piperazinyl |
| 53 | 3-phenyl-1,4-benzodioxin-2-yl | 1 | CH$_2$CO-1-(4-acetyl)-piperazinyl |
| | 3-phenyl-1,4-benzodioxin-2-yl | 0 | CH$_2$CONHCH(CH$_3$)$_2$ |
| 142 | 3-phenyl-1,4-benzodioxin-2-yl | 1 | CH$_2$CONHCH(CH$_3$)$_2$ |
| | 3-phenyl-1,4-benzodioxin-2-yl | 0 | CH$_2$CONH$_2$ |
| 143 | 3-phenyl-1,4-benzodioxin-2-yl | 1 | CH$_2$CONH$_2$ |
| | 6,7-dichloro-3-phenyl-1,4-benzodioxin-2-yl | 0 | CH$_2$CONH$_2$ |
| 144 | 6,7-dichloro-3-phenyl-1,4-benzodioxin-2-yl | 1 | CH$_2$CONH$_2$ |
| | 6,7-dichloro-3-phenyl-1,4-benzodioxin-2-yl | 0 | CH$_2$CO-1-(4-acetyl)-piperazinyl |
| 145 | 6,7-dichloro-3-phenyl-1,4-benzodioxin-2-yl | 1 | CH$_2$CO-1-(4-acetyl)-piperazinyl |
| 148 | 3-phenyl-1H-indol-2-yl | 0 | CH$_2$CONH$_2$ |
| 149 | 3-phenyl-1H-indol-2-yl | 1 | CH$_2$CONH$_2$ |
| 150 | 7-chlorodibenzofuran-1-yl | 0 | CH$_2$CONH$_2$ |
| 151 | 7-chlorodibenzofuran-1-yl | 1 | CH$_2$CONH$_2$ |
| | 8-chlorodibenzofuran-1-yl | 0 | CH$_2$CONH$_2$ |
| 152 | 8-chlorodibenzofuran-1-yl | 1 | CH$_2$CONH$_2$ |
| | 7,8-dichloro-dibenzofuran-1-yl | 0 | CH$_2$CONH$_2$ |
| 153 | 7,8-dichloro-dibenzofuran-1-yl | 1 | CH$_2$CONH$_2$ |

In a second embodiment, the present invention provides a method for treatment of diseases comprising administering to a subject in need thereof a therapeutically effective amount of a compound of formula (A) and formula (I), or a pharmaceutically acceptable salt thereof. In a preferred embodiment, the present invention is to provide methods of treating or preventing diseases or disorders, including treatment of sleepiness, promotion and/or improvement of wakefulness, preferably improvement of wakefulness in patients with excessive sleepiness associated with narcolepsy, sleep apnea, preferably obstructive sleep apnea/hypopnea, and shift work disorder; treatment of Parkinson's disease; Alzheimer's disease; cerebral ischemia; stroke; eating disorders; attention deficit disorder ("ADD"), attention deficit hyperactivity disorder ("ADHD"); depression; schizophrenia; fatigue, preferably fatigue associated with cancer or neurological diseases, such as multiple sclerosis and chronic fatigue syndrome; stimulation of appetite and weight gain and improvement of cognitive dysfunction.

Preferably, when V is a bond, and W is O, S(O)$_y$, or NR$^{10}$, ring D is substituted by a phenyl group.

In a third embodiment, the present invention provides a pharmaceutical compositions comprising the compounds of formula (A) and formula (I) wherein the compositions comprise one or more pharmaceutically acceptable excipients and a therapeutically effective amount of at least one of the compounds of the present invention, or a pharmaceutically acceptable salt or ester form thereof.

Preferably, when V is a bond, and W is O, S(O)$_y$, or NR$^{10}$, ring D is substituted by a phenyl group.

Preferably, the compounds wherein:

U is CH$_2$; and

Y is C$_1$–C$_6$ alkylene optionally substituted with C$_1$–C$_6$ alkylene; and

R$^1$ is CONH$_2$, or CO$_2$R$^{11}$ with R$^{11}$=H or C$_1$–C$_6$ alkyl are excluded.

In a fourth embodiment, the present invention provides for the use of compounds of formula (A) and formula (I) or pharmaceutically acceptable salts thereof for the manufacture of a medicament for the treatment of a disease or disorder.

Preferably, when V is a bond, and W is O, S(O)$_y$, or NR$^{10}$, ring D is substituted by a phenyl group.

These and other objects, features and advantages of the benzyl-thioalkyl derivatives will be disclosed in the following detailed description of the patent disclosure.

Definitions

The following terms and expressions contained herein are defined as follows:

As used herein, the term "about" refers to a range of values from ±10% of a specified value. For example, the phrase "about 50 mg" includes ±10% of 50, or from 45 to 55 mg.

As used herein, a range of values in the form "x-y" or "x to y", or "x through y", include integers x, y, and the integers therebetween. For example, the phrases "1–6", or "1 to 6" or "1 through 6" are intended to include the integers 1, 2, 3, 4, 5, and 6. Preferred embodiments include each individual integer in the range, as well as any subcombination of integers. For example, preferred integers for "1–6" can include 1, 2, 3, 4, 5, 6, 1–2, 1–3, 1–4, 1–5, 2–3, 2–4, 2–5, 2–6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "C$_1$–C$_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon-carbon double bond. A designation "$C_2$–$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" refers to a straight chain, or branched hydrocarbon chains of 2 to 8 carbon atoms having at least one carbon-carbon triple bond. A designation "$C_2$–$C_8$ alkynyl" refers to an alkynyl radical containing from 2 to 8 carbon atoms. Examples include ethynyl, propynyl, isopropynyl, 3,5-hexadiynyl, etc.

As used herein, the term "alkylene" refers to a substituted or unsubstituted, branched or straight chained hydrocarbon of 1 to 8 carbon atoms, which is formed by the removal of two hydrogen atoms. A designation such as "$C_1$–$C_4$ alkylene" refers to an alkylene radical containing from 1 to 4 carbon atoms. Examples include methylene (—$CH_2$—), propylidene ($CH_3CH_2CH$=), 1,2-ethandiyl (—$CH_2CH_2$—), etc.

As used herein, the term "phenylene" refers to a phenyl group with an additional hydrogen atom removed, i.e. a moiety with the structure of:

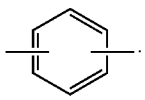

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_5$–$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include such groups as cyclopropyl, cyclobutyl, cyclopentyl, cyclohexl, cycloheptyl, cyclooctyl, pinenyl, and adamantanyl.

As used herein, the term "aryl" refers to a substituted or unsubstituted, mono- or bicyclic hydrocarbon aromatic ring system having 6 to 12 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the terms "heterocycle", "heterocyclic" or "heterocyclyl" refer to a substituted or unsubstituted carbocyclic group in which the ring portion includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

As used herein, the term "heterocycloalkyl" refers to a cycloalkyl group in which one or more ring carbon atoms are replaced by at least one hetero atom such as —O—, —N—, or —S—. Examples of heterocycloalkyl groups include pyrrolidinyl, pyrrolinyl, imidazolidinyl, imidazolinyl, pirazolidinyl, pirazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include pyrrolyl, furanyl, thienyl, pirazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl, etc.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-$NH_2$. In certain embodiments, substituent groups for the compounds of the present invention include the residue of an amino acid after removal of the hydroxyl moiety of the carboxyl group thereof, i.e., groups of formula —C(=O)CH($NH_2$)-(side chain). The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. Biochemistry, 2nd ed.; Worth Publishers: New York, 1975; 71–77, the disclosure of which is incorporated herein by reference. Non-naturally occurring amino acids also include α-amino acids wherein the side chains are replaced with synthetic derivatives.

Representative side chains of naturally occurring and non-naturally occurring α-amino acids are shown below in Table A.

TABLE A

| | | |
|---|---|---|
| H | CH₃ | CH(CH₃)₂ |
| CH₂CH(CH₃)₂ | CH(CH₃)CH₂CH₃ | CH₂OH |
| CH₂SH | CH(OH)CH₃ | CH₂CH₂SCH₃ |
| CH₂C₆H₅ | (CH₂)₄NH₂ | (CH₂)₃NHC(=NH)NH₂ |
| CH₂COOH | CH₂CH₂COOH | CH₂CONH₂ |
| CH₂CH₂CONH₂ | CH₂CH₃ | CH₂CH₂CH₃ |
| CH₂CH₂CH₂CH₃ | CH₂CH₂SH | CH₂CH₂OH |
| CH₂CH₂SCH₃ | (CH₂)₃NH₂ | (CH₂)₂CH(OH)CH₂NH₂ |
| (CH₂)₃NHC(=O)NH₂ | (CH₂)₂ONHC(=NH)NH₂ | CH₂C(=O)NHCH₂COOH |

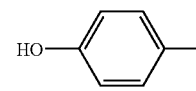
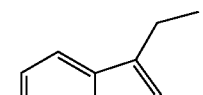
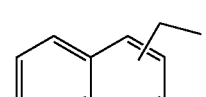
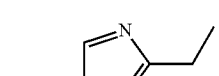
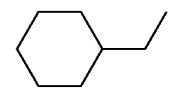

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al., *Enantiomers, Racemates, and Resolutions*; Wiley: New York, 1981, each incorporated by reference herein in their entireties.

It is further recognized that functional groups present on the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., *Protective Groups in Organic Synthesis*, 2d. Ed., Wiley & Sons, 1991.

Synthesis

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

As will be readily understood, functional groups present on the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., "Protective Groups in Organic Synthesis" 2d. Ed., Wiley & Sons, 1991.

The general routes to prepare the examples shown in Table 1 of the present invention are shown in scheme A and in scheme B. The reagents and starting materials are commercially available, or readily synthesized by well-known techniques by one of ordinary skill in the arts. All substituents in the synthetic Schemes, unless otherwise indicated, are as previously defined.

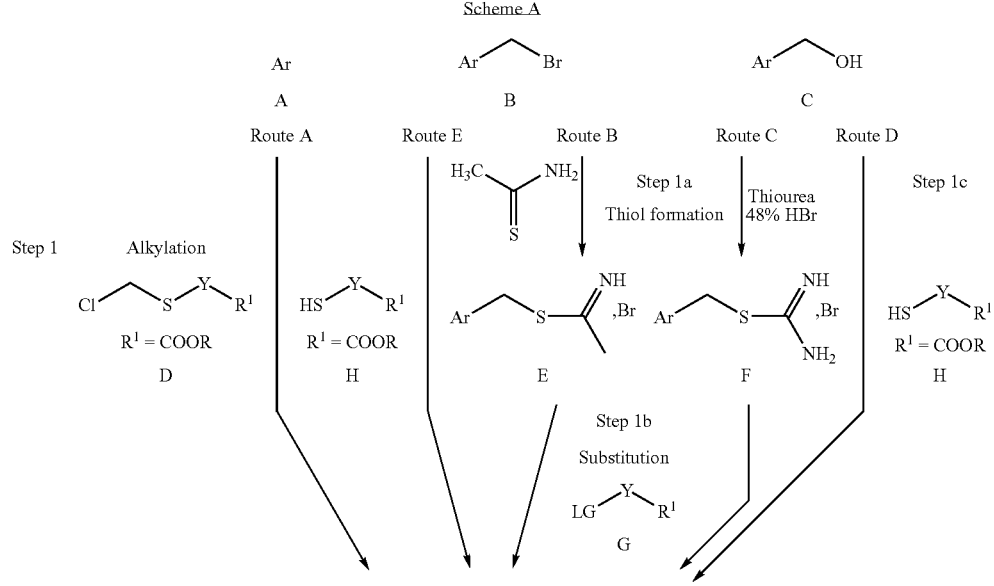

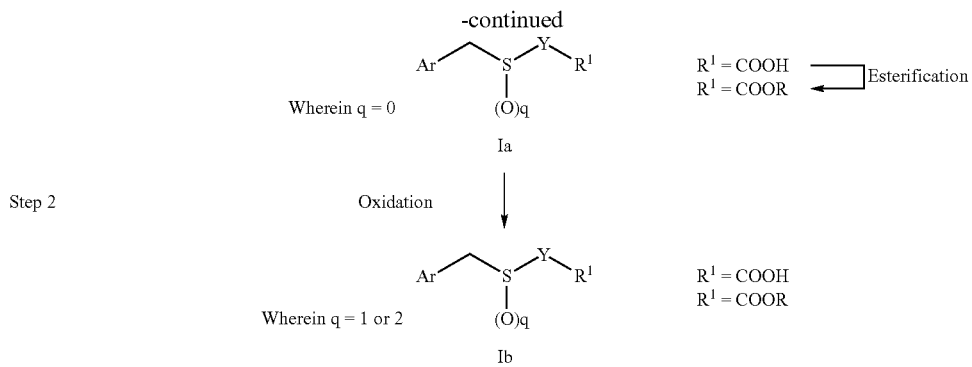

Scheme A: Synthesis of Compounds of General Structure I (Ia and Ib)

Step 1: Synthesis of Compounds of General Structure Ia wherein q is 0

Compounds of general formula Ia may be synthetized via routes A, B, C or D respectively.

Route A:

An appropriate aryl or heteroaryl, optionally substituted, of general formula A wherein Ar is as defined in the final product is reacted with an appropriate compound of general formula D wherein Y and $R^1$ are as defined, in a non-polar solvent as methylenechloride and like ($CHCl_3$, $CS_2$, $CCl_4$) in presence of a lewis acid like $Sn\ Cl_4$, $AlCl_3$, $ZnI_2$ at 0° C., under a nitrogen atmosphere to give compound Ia wherein Ar, Y and $R^1$ are as defined. Upon completion, the reaction mixture is concentrated and compound Ia, is isolated by conventional methods commonly employed by those skilled in the art.

Optionally, ester of general structure Ia ($R^1$=COOR) prepared previously may be hydrolysed in a presence of an inorganic base M-OH as NaOH, LiOH, $NH_4OH$ and the like to obtain the corresponding acid Ia ($R^1$=COOH).

Route B:

In Step 1a, the appropriate compound B wherein Ar is as defined in the final product, dissolved in a aprotic solvent as chloroform and like ($CH_2Cl_2$, Toluene, $CCl_4$ . . . ) is be treated with thioacetamide, at a temperature between 60 and 100° C., preferably at reflux, for a period of time in the 2 to 5 hours range. The reaction mixture is cooled to room temperature (in some cases, an ice-bath might be needed) and the precipitated solid is optionally filtered and thoroughly washed with methylenechloride to generate the appropriate E.

In Step 1b, compound E undergoes a substitution reaction with an appropriate compound G of structure LG-Y-$R^1$ wherein Y and $R^1$ are as defined and LG is an appropriate leaving group (for example an halogene atom as Cl, Br) to generate compounds of general structure Ia wherein q=0, Y and $R^1$ are as defined.

Optionally, the ester of general structure Ia ($R^1$=COOR) prepared previously may be hydrolysed in a presence of an inorganic base M-OH as NaOH, LiOH, NH4OH and the like to obtain the corresponding acid Ia ($R^1$=COOH).

Route C:

In Step 1a, the alcohol moiety of an appropriate compound C wherein Ar is as defined in the final product is converted to the corresponding thiouronium salt of general formula F.

In an aspect, the compound F is formed by reacting a compound C with thiourea and a suitable acid. Suitable acids include but are not limited to mineral acids, such as hydrobromic acid, hydrochloric acid, sulfuric acid.

For example, in Step 1a, an appropriate amount of thiourea in 48% HBr and water is warmed (preferably to 60–70° C.), followed by addition of compound C. The reaction mixture is refluxed and the stirring is continued for an additional period of time for completion of the reaction. The reaction mixture is cooled to room temperature (in some cases, an ice-bath might be needed) and the precipitated solid is optionally filtered and thoroughly washed with water to generate the appropriate thiouronium salt. Sometimes, there is an oil in place of the solid: in that case, the oil is thoroughly washed with water by decantation and used directly in Step 1b.

In Step 1b, the thiouronium salt is first converted into the corresponding thiol which further undergoes a substitution reaction with an appropriate reactant of generic structure structure LG-Y-$R^1$ (compound G) wherein Y and $R^1$ are as defined and LG is a suitable leaving group (for example an halogene atom as Cl, Br) to generate the corresponding compound Ia wherein q=0 and Y and R1 are as defined.

As an example the wet solid of structure F (or the oil with some remaining water) from the previous step is taken into additional water and treated with an aqueous base, preferably sodium hydroxide solution. The mixture is warmed preferably to 70–80° C., but in some cases a higher temperature might be needed) and to it an appropriate amount of LG-Y-$R^1$ in water (or in some cases, an alcoholic solvent) is added. The reaction mixture is refluxed for an appropriate period of time, cooled, taken into water and washed with an organic solvent (preferably ether). The basic aqueous layer is acidified with an inorganic acid solution (e.g. aqueous HCl solution). The aqueous (acidic) solution is then extracted several times into an organic solvent (e.g. ether or ethyl acetate). The combined organic layer is washed with brine, dried ($MgSO_4$ or $Na_2SO_4$) and concentrated to give the crude product that may be used directly in the next step. However, purification could be achieved by employing known purification techniques (e.g. recrystallization or column chromatography) to provide pure compound Ia wherein q is 0, Y and $R^1$ are as defined in the final product.

Route D:

In Step 1c, compound C wherein Ar is as defined in the final product is converted to the corresponding compound Ia by reacting with a appropriate thio derivative of general structure H wherein Y and R1 are as defined in the final product Ia in the presence of ZnI$_2$. Appropriately, the reaction may be conducted under a nitrogen atmosphere.

Alternatively, compound Ia wherein R$^1$ is COOH may be converted into the corresponding alkyl ester R$^1$ is COOR using methods known by people skilled in the art.

Route E:

A solution of compound of general formula B, wherein Ar is as defined in the final product, is reacted at 40 to 100° C. with an appropriate compound of general formula H wherein Y and R$^1$ are as defined, in a polar aprotic solvent as DMF and alkalin mixture. Upon completion, the reaction mixture is concentrated and compound Ia, is isolated by conventional methods commonly employed by those skilled in the art.

Step 2: Synthesis of Compounds of General Structure Ib Wherein q is 1 or 2

Compounds of structure Ia wherein q=0 may optionally be oxidized to generate compounds of structure Ib wherein q is 1 or 2. Compound Ib wherein q is 1 is prepared under mild oxidation conditions by reacting compound Ia wherein q is 0 in an appropriate solvent with an appropriate oxidizing agent. An appropriate oxidizing agent is one that oxidizes the sulphide group of compound Ia. The corresponding product is isolated and purified by methods well known in the art.

For example, to solution of compound Ia in acetic acid, an appropriate oxidizing agent (e.g. 30% ww H$_2$O$_2$, 1 equivalent) in the acetic acid is slowly added. Stirring is continued at low temperature until the disappearance of the starting material, as evidenced by various analytical techniques. The reaction mixture is concentrated. The desired product (compound Ib wherein q is 1) is purified, if needed, by employing known purification techniques (preferably by column chromatography and/or crystallization). In some cases, the oxidation is performed by employing 50% H$_2$O$_2$ in glacial acetic acid solvent.

Compound of formula Ib wherein q=2, may be obtained under more drastic reaction conditions such as H$_2$O$_2$ (more than 2 equivalents) in acidic medium, under heating, preferably at temperature comprise between room temperature and the boiling temperature of the solvent, preferably between 40 and 60° C., for a time sufficient to obtain the desired product, usually approximately between 2 and 10 hours, preferably approximately 8 hours.

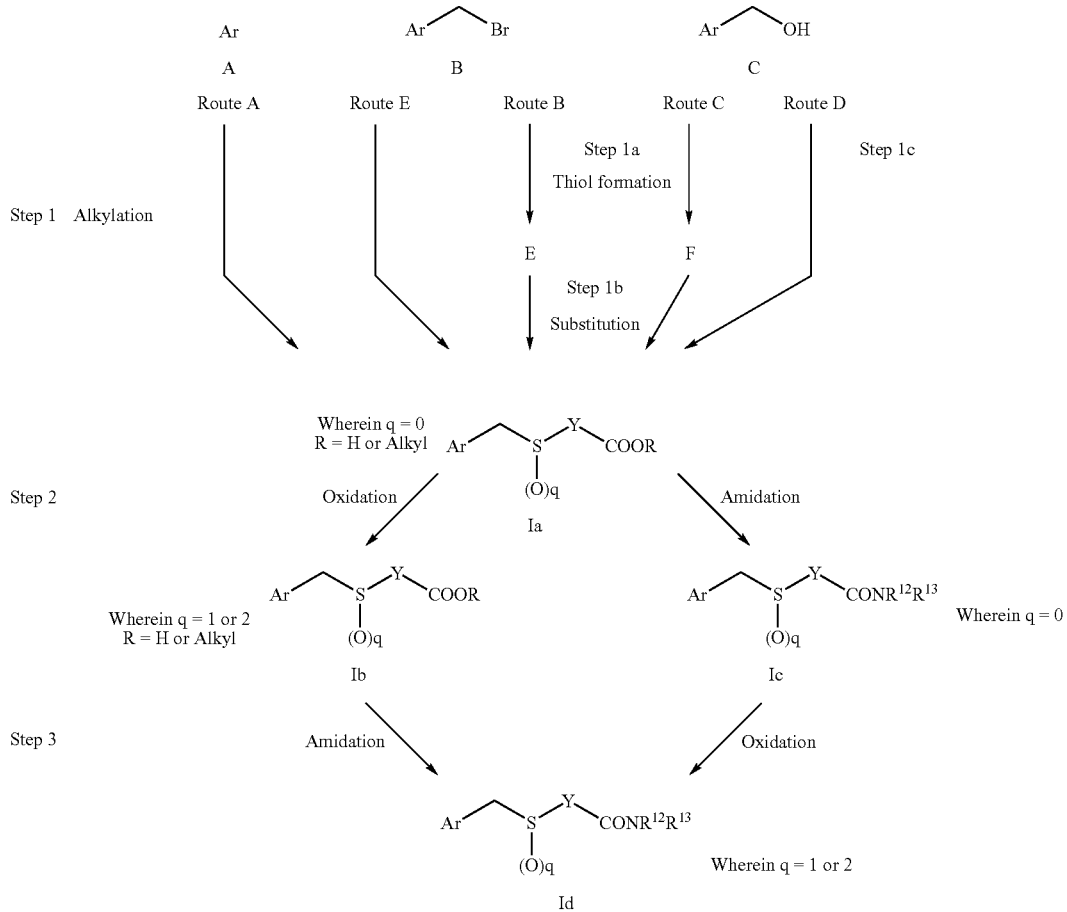

Pathway A = Route A, Ic, Id
Pathway B = Route A, Ib, Id
Pathway C = Route B, Ic, Id
Pathway D = Route B, Ib, Id
Pathway E = Route C, Ic, Id
Pathway F = Route C, Ib, Ic
Pathway G = Route D, Ic, Id
Pathway H = Route D, Ib, Id
Pathway I = Route E, Ic, Id Scheme B: Synthesis of Compounds of General Structure I (Ia, Ib, Ic and Id)

Compound Ia were prepared according to the general procedures described for Step 1 in Scheme A. Then two different synthetic routes may optionally be used to generate compounds Id wherein $R^1$ is $C(=O)NR^{12}R^{13}$.

Step 2: Synthesis of Compounds of General Structure Ic Wherein q=0:

In Step 2, the appropriate carboxylic ester of general formula Ia wherein q=0 and R is alkyl is reacted with an appropriate amine of general structure $NHR^{12}R^{13}$ and converted into the corresponding amide of general formula Ic wherein q=0, Y, Ar and $R^{12}$ and $R^{13}$ are as defined in the final product. May be used aqueous ammonium hydroxide (28%) or methanolic solution of ammonia or ammonia gas to give the desired compound Ic wherein $R^{12}=R^{13}=H$.

Alternatively, in Step 2, the appropriate carboxylic acid of general formula Ia wherein q=0 and R=H may be reacted with an appropriate amine of general formula $NH R^{12}R^{13}$, a coupling reagent such as EDCI or DCCI, or a polymer supported coupling reagent (N-cyclohexyl carbodiimide), and optionally HOBT in an aprotic solvent as methylene chloride and like to provide amide of general formula Ic wherein q=0. An appropriate amine is one which correlates to $R^{12}$ and $R^{13}$ as defined in the final product. In some cases, when the appropriate amide bears a protecting group as the tert-butyloxycarbonyl ("Boc") and like on a second nitrogen group, the protected group is further removed in a subsequent step. De-protection of "Boc" may be performed at room temperature by acid treatment such as 4N HCl in 1,4-dioxane or trifluoroacetic acid in $CH_2Cl_2$.

Step 3: Synthesis of Compounds of General Structure Id Wherein q=1 or 2:

Compounds of structure Ic wherein q=0 may optionally be oxidized to generate compounds of structure Id wherein q=1 or 2 according to the procedure described previously in Scheme A Step 2.

Alternatively, in Step 2, compound Ia wherein q=0 may be oxidized to generate the corresponding compound of general structure Ib wherein q=1 or 2, which, in turn, is amidified appropriately to give raise to compound Id in Step 3 of scheme B.

EXAMPLES

Other features of the invention will become apparent in the course of the following descriptions of exemplary embodiments. These examples are given for illustration of the invention and are not intended to be limiting thereof.

1) Synthesis of Compounds B

Synthesis of 2-Bromomethyl-dibenzofuran 1a

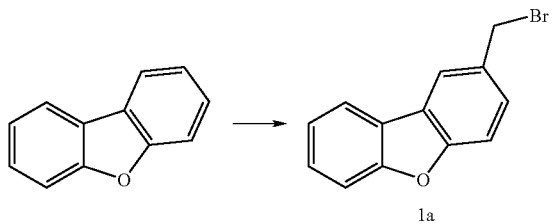

Compound 1a:

A mixture of dibenzofuran (93.5 g, 0.557 M), trioxane (20 g, 0.222 M) and myrystyltrimethylammonium bromide (6.2 g, 18.5 mmol) in 1 L acetic acid and 135 mL of 48% HBr was stirred at 50~60° C. for 28 h, then concentrated; the residue was dissolved in $CH_2Cl_2$, washed with water, dried over $Na_2SO_4$, evaporated to give the crude bromide 1a. Compound 1a was used without further purification in the next step.

Synthesis of 7-chloro-1-bromomethyl-dibenzofuran 1b, 8-chloro-1-bromomethyl-dibenzofuran 1c and 7,8-dichloro-1-bromomethyl-dibenzofuran 1d

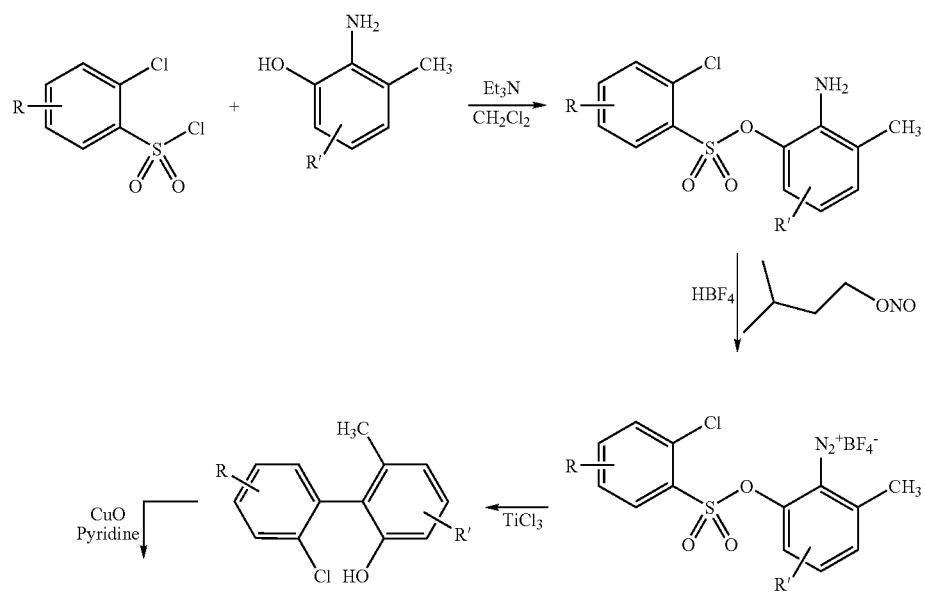

-continued

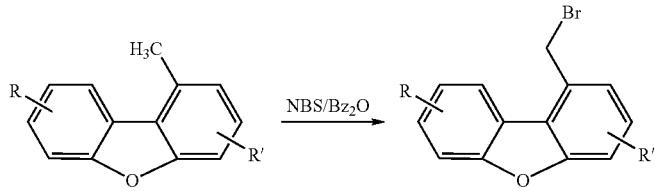

1b: R' = H, R = 4-Cl
1c: R' = H, R = 5-Cl
1d: R' = H, R = 4,5-Cl

1) Synthesis of 2,4-dichloro-benzenesulfonic acid 2-amino-3-methyl-phenyl ester To a mixture of 2,4-dichlorobenzenesulfonyl chloride (20.2 g, 82.3 mmol) and 2-amino-m-cresol (11 g, 89.4 mmol) in 200 mL of methylene chloride, triethylamine (8.5 g, 83.4 mmol) was added dropwise at 5° C. The mixture was stirred at ambient temperature for 16 hours.

The reaction was quenched by water (500 mL), the organic phase washed by water, dried over $Na_2SO_4$ and evaporated. The residue was purified by flash chromatography ($CH_2Cl_2$) to give 26.2 g of an orange oil that crystallized on stand.

1H NMR (400 MHz, $CHCl_3$) δ 2.2 (3H, s), 3.98 (2H, bs), 6.51 (1H, t), 6.75 (1H, d), 6.98 (1H, d), 7.4 (1H, d), 7.65 (1H, s), 7.98 (1H, d).

2) Synthesis of diazonium salt of 2,4-dichloro-benzenesulfonic acid 2-amino-3-methyl-phenyl ester To a suspension of 2,4-dichloro-benzenesulfonic acid 2-amino-3-methyl-phenyl ester (26.2 g, 78.9 mmol) in absolute ethanol (200 ml), was added the tetrafluoroboric acid-dimethylether complex (21.5 g, 160 mmol) at 5° C. under nitrogen to give a solution, then a solution of isoamyl nitrite (11.6 g, 95.2 mmol) in 80 mL ethanol was added dropwise during 20 minutes to give a suspension. The mixture was stirred and kept at 5° C. for one hour, and then the suspension was filtered, washed with ether, dried under vacuum to give 32.9 g of the diazonium slat as a white powder.

This compound is pure enough for the next step.

3) Synthesis of 2',4'-dichloro-6-methyl-biphenyl-2-ol

To a suspension of the diazonium (32.9 g, 76.2 mmol) in 280 mL of acetone, was added dropwise a solution of $TiCl_3$ in aqueous HCl (>10% wt in 20–30% wt HCl, 250 mL) at 5° C. during 30 minutes. The reaction was maintained for additional 2 hours, then diluted with 300 mL of water and extracted by methylenechloride (2×200 mL). The combined extracts were washed with water, dried over $Na_2SO_4$, evaporated to give the crude product which was purified twice by flash chromatography (cyclohexane/ethyl acetate, 5/1) to 16.5 g of a yellowish oil.

1H NMR (400 MHz, $CHCl_3$) δ 2.05 (3H, s), 4.55 (1H, s), 6.75 (1H, d), 6.85 (1H, d), 7.2 (2H, m), 7.4 (1H, dd), 7.65 (1H, s).

4) Synthesis of 7-chloro-1-methyl-dibenzofuran

A mixture of 2',4'-dichloro-6-methyl-biphenyl-2-ol (8.75 g, 34.7 mmol), $K_2CO_3$ (25 g, 180 mmol) and CuO (17 g, 214 mmol) in 200 mL of pyridine was refluxed under nitrogen for 2 hours. Pyridine was eliminated by distillation. To the residue were added 200 mL of water and 200 mL of methylenechloride, the resulting mixture was filtered through Celite. The organic phase was washed with water, dried over $Na_2SO_4$ and evaporated. The residue was purified by flash chromatography (cyclohexane/ethyl acetate, 5/1) to give 6.27 g of beige solid.

1H NMR (400 MHz, $CHCl_3$) δ 2.76 (3H, s), 7.12 (1H, d), 7.4 (3H, m), 7.5 (1H, d), 7.95 (1H, s).

5) Synthesis of 7-chloro-1-bromomethyl-dibenzofuran: 1b

A mixture of 7-chloro-1-methyl-dibenzofuran (6.27 g, 29.1 mmol), N-bromosuccinimide (5.4 g, 30.3 mmole) and dibenzoyl peroxide (0.82 g, 3.4 mmole) in tetrachlorocarbon (100 mL) was heated at reflux for 3 hours, and then concentrated to about 50 mL. The resulting suspension was filtered, rinsed by $CCl_4$. The solid was dissolved in $CH_2Cl_2$, washed by water, dried over $Na_2SO_4$, evaporated to give 6.16 g of beige solid.

1H NMR (400 MHz, $CHCl_3$) δ 4.95 (2H, s), 7.32 (1H, d), 7.4 (2H, m), 7.55 (1H, d), 7.62 (1H, d), 8.03 (1H, d).

Compounds 1c and 1d

Compounds 1c and 1d were synthetized according to the protocol described for compound Ib 4.1 g of 8-chloro-1-bromomethyl-dibenzofuran 1c were obtained using 2,5-dichlorobenzenesulfonyl chloride (20.2 g, 82.3 mmol) and 2-amino-m-cresol (11 g, 89.4 mmol) as starting material.

1H NMR (400 MHz, $CHCl_3$) δ: 4.95 (2H, s), 7.32 (1H, d), 7.4 (2H, m), 7.53 (2H, m), 8.1 (1H, s).

8.7 g of 7,8-dichloro-1-bromomethyl-dibenzofuran 1d were obtained using 2,4,5-trichlorobenzenesulfonyl chloride (20.2 g, 82.3 mmol) and 2-amino-m-cresol (11 g, 89.4 mmol) as starting material.

1H NMR (400 MHz, $CHCl_3$) δ: 4.95 (2H, s), 7.3 (1H, d), 7.43 (H, t), 7.53 (1H, m), 7.72 (1H, d), 8.2 (1H, s).

2) Synthesis of Compounds C

Synthesis of (3-Phenyl-benzo[b]thiophen-2-yl)-methanol 3

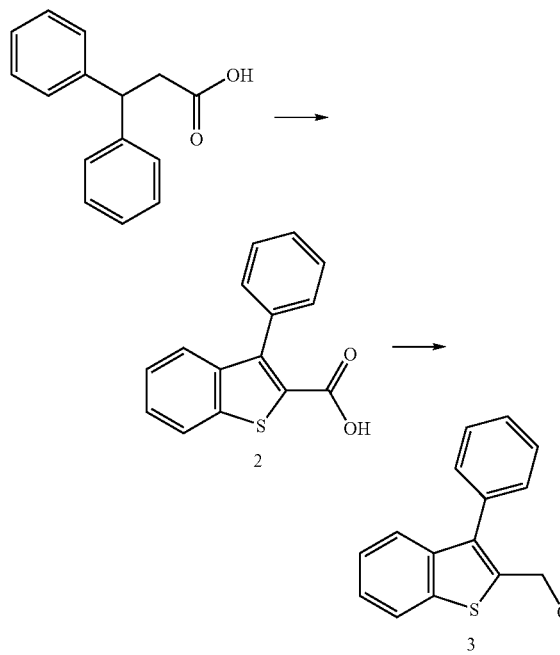

Compound 2: Synthesis of (3-Phenyl-benzo[b]thiophen-2-yl)-carboxylic acid

To a mixture of 3,3-diphenylpropionic acid (20 g, 88.5 mmol) in 9 mL pyridine was added 8 mL $SOCl_2$ at room temperature. The resulting mixture was heated to 150~160° C., then additional 23 mL $SOCl_2$ were added dropwise during 1 h to give a brownish solution, the reaction was stirred at reflux for 2 h, cooled, poured into a mixture of $H_2O$/conc. HCl/THF (100 mL/10 mL/150 mL). The mixture was refluxed for 3 h then cooled. The organic layer was separated, washed with brine, dried over $MgSO_4$ and concentrated, the residue was treated with 200 mL ethyl ether, filtered and the filtrate concentrated. The crude product was crystallized in toluene to furnish 10 g of compound 2.

1H NMR (400 MHz, $CHCl_3$) δ 7.38 (3H, m), 7.5 (5H, m), 7.89 (1H, dd).

Compound 3: Synthesis of 3-Phenyl-benzo[b]thiophen-2-yl)-methanol

To a mixture of compound 2 (21.9 g, 86 mmol) in 300 mL dry THF, was added dropwise a solution of 1 M $BH_3$-THF (105 mL, 105 mmol) at room temperature under $N_2$ during 15 minutes. The mixture was stirred at room temperature for 18 h, and then quenched by brine. The separated organic layer was washed with brine, dried over $MgSO_4$ and concentrated. The crude product was purified by flash chromatography ($CH_2Cl_2$/methanol, 100/1) yielding 17.2 g of compound 3 as a colorless oil that crystallized on stand.

1H NMR (400 MHz, $CHCl_3$) δ 2 (1H, bs), 4.83 (2H, s), 7.33 (2H, m), 7.4 (3H, m), 7.5 (2H, m), 7.6 (1H, d), 7.82 (1H, dd).

Synthesis of (2-Phenyl-benzofuran-3-yl)-methanol 7

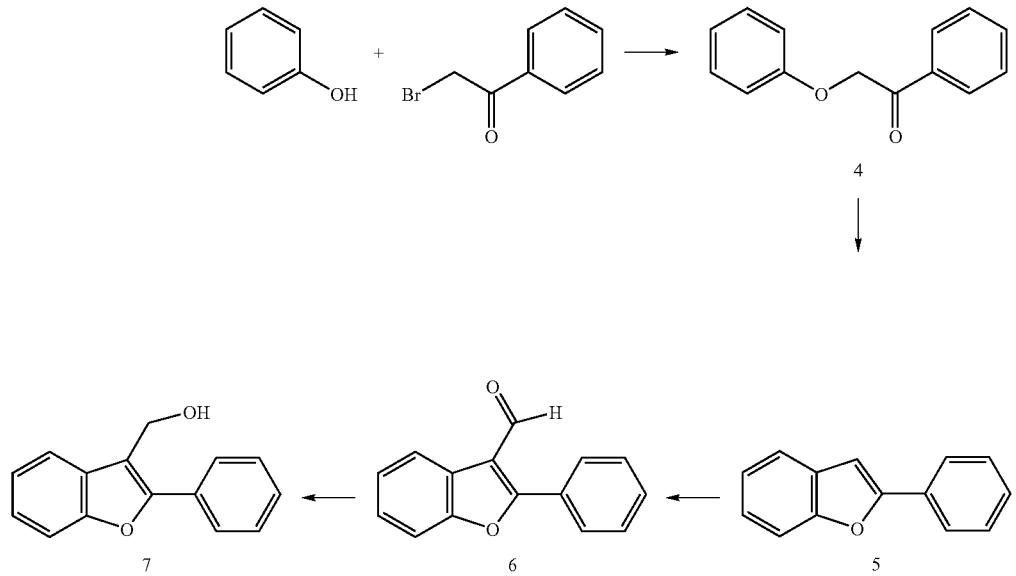

Compound 4

A mixture of phenol (23.6 g, 0.25 M), 2-bromoacetophenone (50 g, 0.25 M) and $K_2CO_3$ (35 g, 0.25 M) in 150 mL of acetone was refluxed for 4 h, cooled, poured into 1.5 L of water to give a suspension. The solid was collected by filtration, then crystallized in ethanol, dried under vacuum to give 33 g of compound 4 as a beige powder.

Compound 5

To 150 mL of polyphosphoric acid heated at 130~140° C., was added compound 4 (20 g, 94.3 mmol), the reaction was kept at 130~140° C. for 3 h and then poured into 1 L of water. The solid was filtered, rinsed with water, dried in vacuum to give crude product that was crystallized in ethanol to afford 12.2 g of compound 5 as a yellow crystal.

1H NMR (400 MHz, CHCl$_3$) δ 7.05 (1H, s), 7.25 (2H, m), 7.35 (1H, m), 7.45 (2H, t), 7.5 (1H, d), 7.6 (1H, d), 7.85 (2H, d).

Compound 6

POCl$_3$ (10.5 mL, 112.5 mmol) was added to DMF (21 mL at 0~5° C.). The mixture was stirred at room temperature for 10 minutes, then compound 5 (4 g, 20.6 mmol) was added portionwise. The resultant mixture was heated at 80~90° C. for 5 h, stirred overnight at room temperature, poured on ice, and then extracted into CH$_2$Cl$_2$, the organic layer was washed with water, dried over MgSO$_4$, concentrated to give an oil. The crude product was purified by flash chromatography (cyclohexane/ethyl acetate, 5/1) to afford 3.3 g of compound 6 as a yellow solid.

1H NMR (400 MHz, CHCl$_3$) δ: 7.4 (2H, m), 7.55 (4H, m), 7.83 (2H, m), 8.25 (1H, m), 10.33 (1H, s).

Compound 7

To a solution of compound 6 (3.16 g, 14.2 mmol) in 30 mL of 2-propanol and 20 mL of THF, NaBH$_4$ (0.8 g, 21.1 mmol) was added at room temperature. 10 minutes later, the reaction mixture was concentrated and quenched with water. The resulting precipitate was filtrated, dried under vacuum to furnish 3.19 g of pure compound 7.

1H NMR (400 MHz, CHCl$_3$) δ 4.95 (2H, d), 7.25 (2H, m), 7.45 (1H, m), 7.5 (3H, m), 7.7 (1H, d), 7.85 (2H, d).

Synthesis of (9H-Fluoren-1-yl)-methanol 9

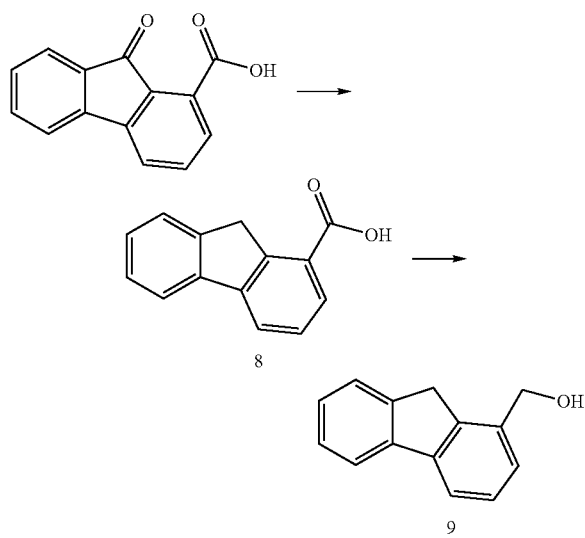

Compound 8

A mixture of 9-fluorenone-1-caboxylic acid (6 g, 26.8 mmol), a 55% HI solution HI (10.5 mL) and red phosphorous (9.6 g, 310 mmol) in 400 mL acetic acid was refluxed for 48 h, then concentrated. Following addition of 200 mL of water; the mixture was stirred overnight and filtered. The cake was treated in 200 mL water and 5 mL concentrated NaOH and filtered to remove residual phosphorous. The filtrate was adjusted to pH 2 with 4 N HCl to give a suspension that was filtered, washed with, dried in vacuum to afford 5.47 g of compound 8 as a beige solid.

1H NMR (400 MHz, DMSO-d$_6$) δ 4.25 (2H, s), 7.35 (2H, m), 7.55 (1H, t), 7.63 (1H, d), 7.92 (1H, d), 7.96 (1H, d), 8.2 (1H, d).

Compound 9

To a slurry of compound 8 (5.47 g, 26 mmol) in 50 mL dry THF, was added dropwise a 1 M solution BH$_3$-THF (28 mL) at room temperature over a 35 minutes period. The mixture was stirred at room temperature for 16 h then quenched by brine. The organic layer was washed with brine, dried over MgSO$_4$, concentrated to give 4.5 g of compound 9 as a yellow solid.

1H NMR (400 MHz, CHCl$_3$) δ 3.9 (2H, s), 4.85 (2H, s), 7.35 (4H, m), 7.55 (1H, d), 7.75 (1H, d), 7.8 (1H, d).

Synthesis of (9H-Fluoren-2-yl)-methanol 10

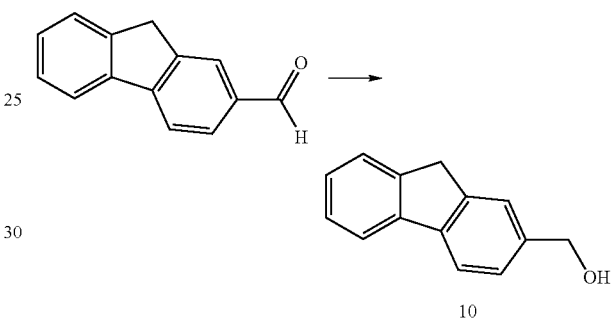

Compound 10

Compound 10 was prepared according to the process described for as for 3-hydroxymethyl-2-phenyl-benzofuran 7.

Reagents: Fluorene-2-carboxaldehyde (5.57 g, 28.7 mmol) and NaBH$_4$ (1.6 g, 42.3 mmol).

1H NMR (400 MHz, CHCl$_3$) δ 3.9 (2H, s), 4.75 (2H, s), 7.3 (3H, m), 7.55 (2H, m), 7.75 (2H, t).

Synthesis of (9H-Fluoren-4-yl)-methanol 13

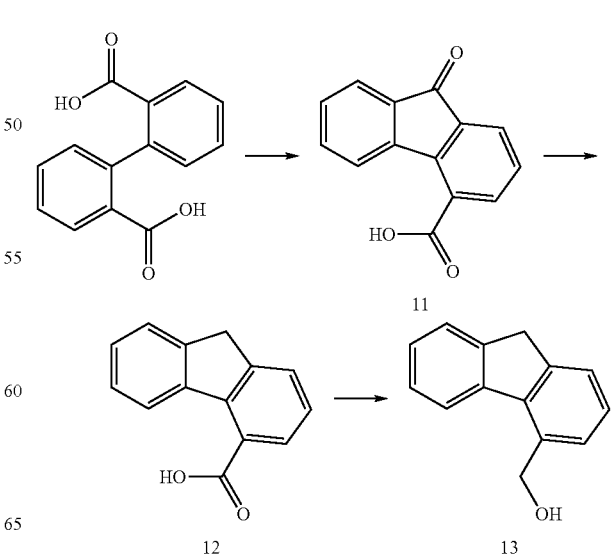

Compound 11

To 200 mL of concentrated H$_2$SO$_4$, was added biphenic acid (70 g, 0.289 M). The resulting mixture was heated to 140° C. for 20 minutes, cooled, poured into ice-water (2 L) to give a suspension. The mixture was filtered, washed with water, dried at 50° C. under vacuum to afford 56 g of compound 11 as greenish yellow solid.

1H NMR (400 MHz, DMSO-d$_6$) δ: 7.45 (2H, m), 7.65 (2H, q), 7.8 (1H, d), 7.95 (1H, d), 8.25 (1H, d).

Compound 12

Compound 12 was prepared according to the procedure described for 9-fluorenone-1-caboxylic acid 9.

Reagents: Compound 11 (22.4 g, 0.1 M), red phosphorous (35.8 g, 1.15 M) and 58% HI (39 ml).

1H NMR (400 MHz, CHCl$_3$) δ 3.95 (2H, s), 7.4 (3H, m), 7.55 (H, d), 7.75 (1H, d), 8.05 (1H, d), 8.6 (1H, d).

Compound 13

Compound 13 was synthesized in a manner substantially the same as for 3-hydroxymethyl-2-phenyl-benzofuran 8

Reagents: Compound 12 (9.66 g, 49.3 mmol) and NaBH$_4$ (1.9 g, 48.7 mmol).

1H NMR (400 MHz, CHCl$_3$) δ 2.13 (1H, t), 5.1 (2H, d), 7.33 (2H, m), 7.5 (2H, m), 7.6 (1H, d), 7.9 (1H, d), 7.95 (1H, d).

Dibenzofuran-4-yl-methanol 16 and dibenzothiophen-4-yl-methanol 17

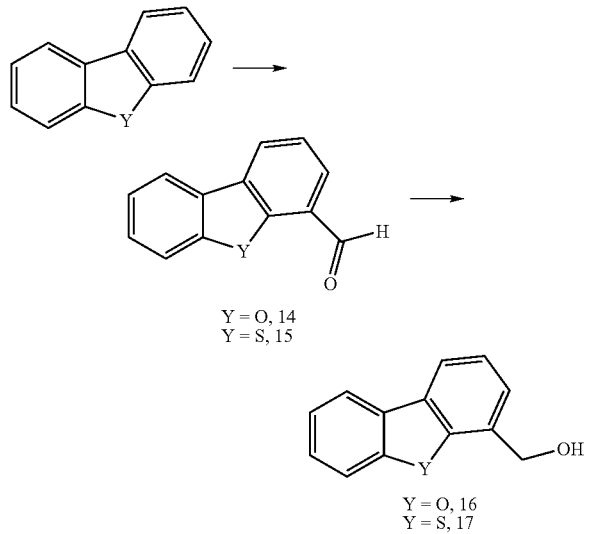

Y = O, 14
Y = S, 15

Y = O, 16
Y = S, 17

Compound 14

To a solution of dibenzofuran (6.2 g, 36.9 mmol) in 100 mL dry THF, was added a solution of 1.6 M n-BuLi in hexane (26 mL, 41.6 mmol) at 5° C. under a N$_2$ atmosphere over a 30 minutes period. The resulting solution was stirred at 5° C. for 1 h, then DMF (3.2 mL, 41.6 mmol) was added and stirring maintained for 20 minutes at room temperature before adding brine. The organic layer was washed with, dried over MgSO$_4$ and concentrated. The crude product was recrystallized in 2-propanol to furnish 3.82 g of compound 14 as a yellow crystal.

1H NMR (400 MHz, CHCl$_3$) δ 7.4 (1H, t), 7.46 (1H, t), 7.53 (1H, t), 7.7 (1H, d), 7.95 (2H, dd), 8.2 (1H, d), 10.58 (1H, s).

Compound 15

Compound 15 was prepared according to the procedure described for compound 14. Reagents: dibenzothiophene (36.8 g, 226 mmol) and 1.6 M n-BuLi in hexane (140 mL, 224 mmol), DMF (16.5 g, 226 mmol)

1H NMR (400 MHz, CHCl$_3$) δ 7.53 (2H, m), 7.68 (1H, t), 7.97 (1H, m), 7.99 (1H, dd), 8.22 (1H, m), 8.44 (1H, dd), 10.3 (1H, s).

Compound 16

Compound 16 was synthesized in a manner substantially the same as for 3-hydroxymethyl-2-phenyl-benzofuran 7

Reagents: Compound 14 (9.66 g, 49.3 mmol) and NaBH$_4$ (1.9 g, 48.7 mmol).

1H NMR (400 MHz, CHCl$_3$) δ 2.13 (1H, t), 5.1 (2H, d), 7.33 (2H, m), 7.5 (2H, m), 7.6 (1H, d), 7.9 (1H, d), 7.95 (1H, d).

Compound 17

Compound 17 was prepared according to the procedure described for compound 16

Reagents: compound 15 (22.2 g, 104.7 mmol) and NaBH4 (4.5 g, 118 mmol)

1H NMR (400 MHz, CHCl$_3$) δ 1.95 (1H, t), 5 (2H, d), 7.5 (4H, m), 7.87 (1H, m), 8.1 (1H, m), 8.2 (1H, m).

Synthesis of Dibenzothiophen-2-yl-methanol 19

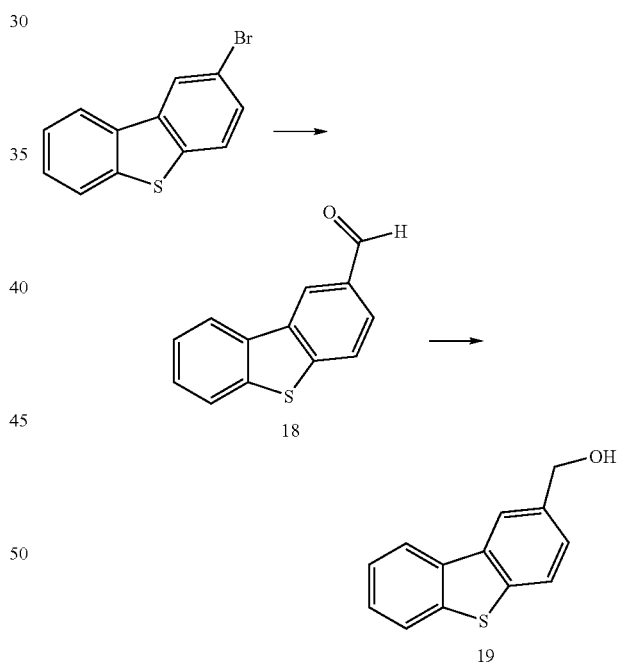

18

19

Compound 18

To a solution of 2-bromodibenzofuran (33.7 g, 0.128 M) (*Bull. Soc. Chim. Fr,* 1973, 11, 3110–3115) in 300 mL of dry ethyl ether, a solution of 1.6 M n-BuLi in hexane (85 mL, 0.136 M) was added at 5° C. under N$_2$ over a 30 minutes period, followed by the addition of DMF (10 g, 0.137 M). The mixture was stirred at room temperature for 40 minutes, then a saturated solution of NH$_4$Cl (300 mL) was added. The organic layer was washed with brine, dried over Na$_2$SO$_4$ and concentrated. The crude product was recrystallized in ethanol to furnish 25.9 g of compound 18 as a yellow crystal.

1H NMR (400 MHz, CHCl$_3$) δ 7.55 (2H, m), 7.87 (1H, m), 8.0 (2H, m), 8.25 (1H, m), 8.7 (1H, s), 10.2 (1H, s).

Compound 19

Compound 19 was synthesized in a manner substantially the same as for 3-hydroxymethyl-2-phenyl-benzofuran 7.

Reagents: Compound 18 (20.6 g, 97.2 mmol) and NaBH$_4$ (4 g, 105.8 mmol).

1H NMR (400 MHz, CHCl$_3$) δ 4.86 (2H, s), 7.5 (3H, m), 7.86 (2H, m), 8.25 (1H, m), 8.2 (2H, m).

Synthesis of Substituted dibenzofuran-2-yl-methanol 44

78.3 g of the aldehyde 20 as a brownish solid. This compound was slurried in 2-propanol (1 L), then NaBH$_4$ (14 g, 0.378 M) was added portionwise at room temperature. The resulting mixture was stirred at room temperature for 1 h, then concentrated. The residue was poured into water (1.5 L) to give a suspension. After filtration, the resulting solid, washed with water, dried at 50° C. under vacuum to give 76 g of 4-fluorophenoxybenzyl alcohol 26 as a yellowish crystal.

1H NMR (400 MHz, CHCl$_3$) δ 4.67 (2H, d), 7.0 (6H, m), 7.33 (2H, d).

Compound 32

To a solution of compound 26 (21.8 g, 0.1 M) and triethylamine (14 mL, 0.1 M) in 300 mL CH$_2$Cl$_2$, acetyl

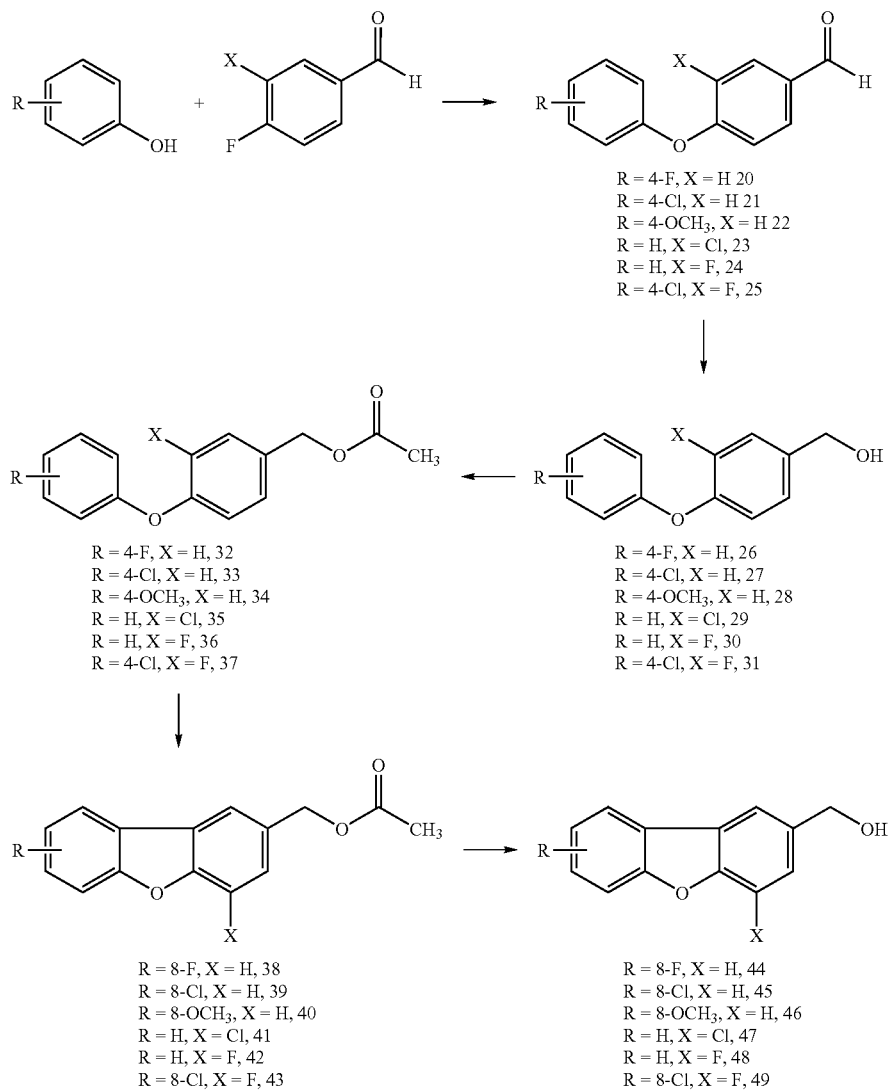

Compounds 20 and 26

A mixture of 4-fluorophenol (41.3 g, 0.37 M), 4-fluorobenzaldehyde (45.7 g, 0.37 M) and K$_2$CO$_3$ (55 g) in 450 mL DMF was refluxed for 4 h, cooled, poured into ice water (1.5 L) to give a suspension. The mixture was filtered, washed with water, dried at 50° C. under vacuum to generate chloride (8 g, 0.102 M) was added at room temperature. The mixture was kept at room temperature for 18 h, then washed with water, dried over Na$_2$SO$_4$, concentrated to afford 27.3 g of 4-chlorophenoxybenzyl acetate 32 as an oil.

1H NMR (400 MHz, CHCl$_3$) δ 2.1 (3H, s), 5.05 (2H, s), 6.93 (2H, d), 7.0 (4H, m), 7.3 (2H, d).

Compound 38

A brownish mixture of 32 (22.2 g, 85.4 mmol) and palladium acetate (35 g, 156 mmol) in acetic acid (250 mL) was refluxed for 18 h, then filtered on Celite to eliminate palladium. The filtrate was concentrated to dryness. The crude producte was purified by flash chromatography (cyclohexane/ethyl acetate, 5/1) to generate 17.6 g of 8-fluoro-2-acetoxymethyldibenzofuran 38 as an off-white solid.

1H NMR (400 MHz, CHCl$_3$) δ 2.1 (3H, s), 5.2 (2H, s), 7.12 (1H, tt), 7.46 (2H, m), 7.5 (1H, d), 7.56 (1H, dd), 7.73 (1H, s).

Compound 44

To a suspension of 38 (10.3 g, 40 mmol) in 150 mL of methanol and 50 mL of water, LiOH monohydrate (3.5 g, 83.3 mmol) was added at room temperature. The mixture was stirred at 50° C. for 30 minutes, concentrated. The mixture was quenched with water (200 mL) to give a suspension that was filtered, washed with water, dried at 50° C. under vacuum to give 8.4 g of 8-fluoro-2-hydroxymethyldibenzofuran 44 as a white crystal.

1H NMR (400 MHz, DMSO-d$_6$) δ 4.7 (2H, s), 7.33 (1H, m), 7.5 (1H, d), 7.67 (1H, d), 7.7 (1H, m), 8.03 (1H, dd), 8.11 (1H, s).

Compounds 45 to 49

Compounds 45 to 49 were processed according to the procedure described for compound 44.

Synthesis of Dibenzofuran-1-yl-methanol 54 and dibenzofuran-3-yl-methanol 53

Compounds 51 and 52

A mixture of 3-phenoxybenzyl acetate 50 (21.8 g, 90 mmol) (prepared by acetylation of commercial 3-phenoxybenzyl alcohol) and palladium acetate (40 g, 179 mmol) in acetic acid (300 mL) was refluxed for 6 h, cooled and filtered. The filtrate was evaporated to dryness and the residue treated with 100 mL of a mixture cyclohexane/ethyl acetate (6/1) and filtered. The filtrate was concentrated to give a colored oil which was purified by chromatography on silica gel (cyclohexane/ethyl acetate, 6/1) to afford pure dibenzofuran-3-yl-methyl acetate 51 (3.4 g) and a mixture of dibenzofuran-3-yl-methyl acetate 51 (Rf=0.6) and dibenzofuran-1-yl-methyl acetate 52 contaminated with compound 51 (Rf of compound 52=0.53) (8.4 g) as a white solid.

52 will be used without any further purification in the next step

Compound 51: 1H NMR (400 MHz, CHCl$_3$) δ 2.15 (3H, s), 5.3 (2H, s), 7.33 (2H, t), 7.45 (1H, t), 7.56 (1H, d), 7.59 (1H, s), 7.96 (1H, t).

Compounds 53 and 54

Acetyl group of Compound 51 is further removed to give pure compound 53 using the same procedure as described for preparation of compound 44.

Starting from 52 (contaminated by some isomer 51), a mixture of 53 and 54 was prepared according to the same method.

Compound 53: 1H NMR (400 MHz, CHCl$_3$) δ 2.0 (1H, bs), 4.84 (2H, s), 7.45 (1H, t), 7.53 (1H, d), 7.59 (1H, s), 7.92 (2H, dd).

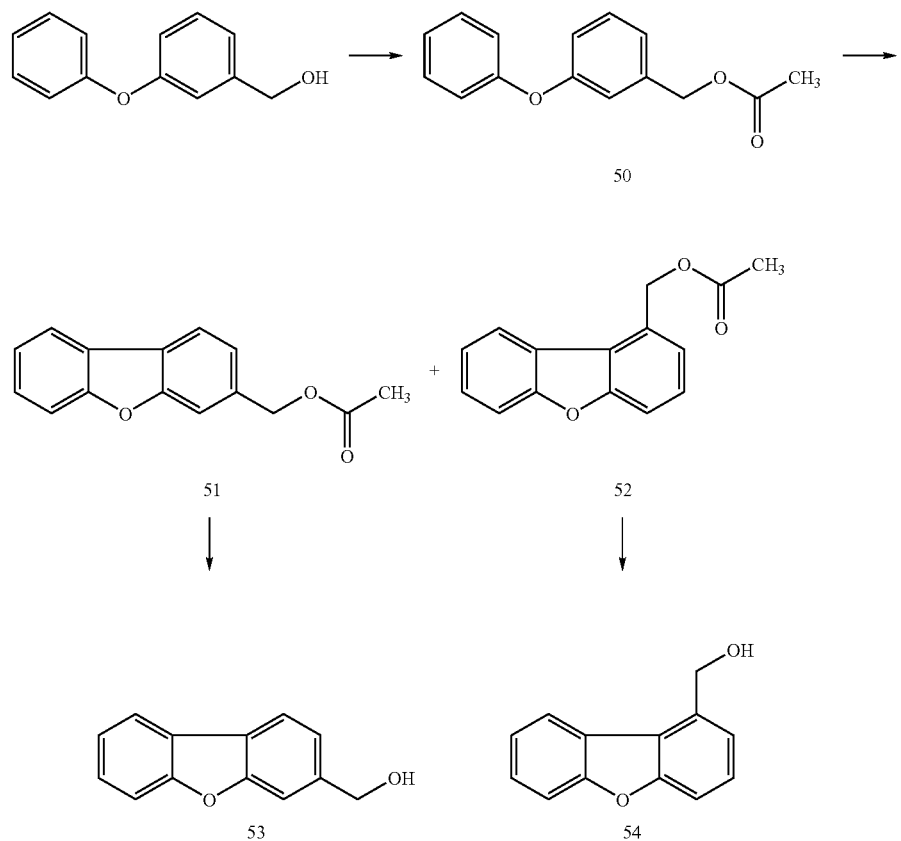

Synthesis of (3-Phenyl-benzo[1,4]dioxin-2-yl)-methanol 59a and (6,7-Dichloro-3-phenyl-benzo[1,4]dioxin-2-yl)-methanol 59b

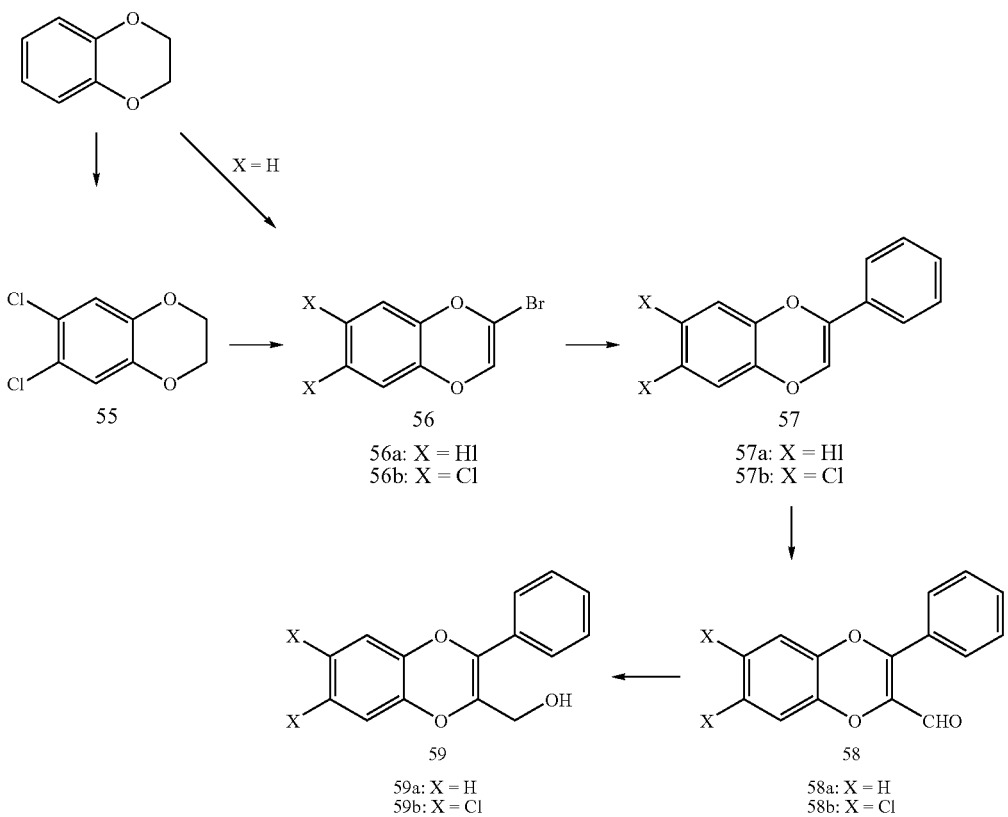

Compound 55

Compound 55 was prepared according to the procedure described in *Organic Process Research & Development*, 5(2), 2001, 116–1121.

Reagents: 1,4-benzodioxane (10 g, 73.4 mmol), N-chlorosuccinimide (20.6 g, 154 mmol) and acetic acid (20 mL).

Yield=68% (m=10.2 g).

$^1$H NMR (400 MHz, CDCl$_3$) δ 4.3 (4H, s), 6.95 (2H, s).

Compound 56a (X═H)

Compound 56a was prepared according to the procedure described in *Synthesis*, 1977, 755 and *Tetrahedron*, 46(3), 1990, 921–934.

Reagents: 1,4-benzodioxane (12 g, 88 mmol), N-bromosuccinimide (37.6 g, 211 mmol), AIBN (small amount), CCl$_4$ (120 ml), potassium t-butoxide (15 g, 134 mmol), Et$_2$O (250 ml).

Yield=66% (m=12.4 g).

$^1$H NMR (400 MHz, CDCl$_3$) δ 6.05 (1H, s), 6.6–6.9 (4H, m).

Compound 56b (X═Cl)

Similarly, compound 56b was prepared.

Under nitrogen, a mixture of compound 55 (5.6 g, 27.4 mmol), N-bromosuccinimide (11.7 g, 65.8 mmol) and a small amount of AIBN in tetrachloromethane (340 ml) is refluxed for 5 h. After cooling, the solid material is filtered off and the solution is evaporated to give 2,3-dibromo-2,3-dihydro-1,4-benzodioxin. Under nitrogen, to a stirred suspension of potassium t-butoxide (9.22 g, 82 mmol) in anhydrous tetrahydrofuran (45 ml), was added dropwise at 0° C., a solution of 2,3-dibromo-2,3-dihydro-1,4-benzodioxin in tetrahydrofuran (35 ml), and the mixture was stirred for 4 h. The solid was filtered off on celite and the solution is concentrated. 200 ml of water was added and the aqueous layer was extracted with dichloromethane. The organic layers were dried over MgSO$_4$ and concentrated to afford a residue which was purified by column chromatography (petroleum ether) to give 6.26 g (yield=81%) of compound 56b (white powder).

$^1$H NMR (400 MHz, CDCl$_3$) δ 6.05 (1H, s), 6.80 (1H, s), 6.85 (1H, s).

Compound 57a (X═H)

Compound 57a was prepared according to the procedure described in *Tetrahedron*, 53(6), 1997, 2061–2074.

Reagents: compound 56a (12.4 g, 58.2 mmol), toluene (200 ml), Na$_2$CO$_3$ 2M (58 ml), phenylboronic acid (14.2 g, 116 mmol), EtOH (70 ml), tetrakis(triphenylphosphine)palladium (2.7 g, 2.3 mmol).

Yield=74% (m=9 g).

$^1$H NMR (400 MHz, CDCl$_3$) δ 6.45 (1H, s), 6.6–6.9 (4H, m), 7.25–7.5 (5H, m).

Compound 57b (X═Cl)

Similarly, compound 57b was prepared.

Under nitrogen, to a solution of compound 56b (0.3 g, 1.07 mmol) in 4 ml of toluene, were added 1.1 ml of an aqueous solution o 2M Na$_2$CO$_3$, phenylboronic acid (0.26 g, 2.14 mmol) in 1.3 ml of ethanol and tetrakis(triphenylphosphine)palladium (0.05 g, 0.043 mmol). The mixture was heated at 78° C. for 3 h.

After concentration, 30 ml of water was added and the aqueous layer was extracted with dichloromethane. The organic layers were dried over MgSO$_4$ and concentrated to afford a residue which was purified by column chromatography (petroleum ether) to give 0.24 g (yield=81%) of compound 57b (white powder).

$^1$H NMR (400 MHz, CDCl$_3$) δ 6.45 (1H, s), 6.80 (1H, s), 6.85 (1H, s), 7.25–7.5 (5H, m).

Compound 58a (X═H)

Compound 58a was prepared according to the procedure described in Chem. of heterocyclic Compds, 35(10), 1999, 1480–1481.

Reagents: compound 57a (9 g, 42.8 mmol), phosphorus oxychloride (7.88 g, 51.4 mmol), DMF (20 ml, 257 mmol).

Yield: 74% (7.5 g).

$^1$H NMR (400 MHz, CDCl$_3$) δ 6.8–7.1 (4H, m), 7.4–7.8 (5H, m), 9.15 (1H, s).

Compound 58 b (X═Cl)

Similarly, compound 58b was prepared.

Under nitrogen, to a stirred solution of compound 57b (5.30 g, 19 mmol) in 120 ml of DMF was added dropwise POCl$_3$ (2.12 mL, 22.8 mmol). The reaction mixture was stirred at 60° C. during 22 h. Then, the mixture was treated with a solution of sodium acetate trihydrate (11.6 g) in water (14 mL) and heated with stirring until crystallization began. After cooling, water was added and the precipitate was filtered off and then washed with 2-propanol to give 4.9 g (yield=84%) of compound 58b (yellow powder).

$^1$H NMR (400 MHz, DMSO-d$_6$) δ 9.12 (1H, s), 7.75–7.52 (5H, m), 7.45 (1H, s), 7.40 (1H, s), 6.85 (1H, s).

Compound 59a (X═H)

Under nitrogen, to a stirred suspension of compound 58a (7.5 g, 31.5 mmol) in 80 ml of methanol, was added at 0° C., by fraction, sodium borohydride (0.77 g, 20.5 mmol). After 45 min, 10 ml of water was added and the mixture was neutralized with HCl 2N and then methanol was evaporated. After extraction with CH$_2$Cl$_2$ (2*150 ml), the organic layer was dried over MgSO$_4$ and concentrated to give 7.6 g (yield=100%) of compound 59a (white powder).

$^1$H NMR (400 MHz, CDCl$_3$) δ 3.95 (2H, d), 5.3 (1H, t), 6.8–7.1 (4H, m), 7.30–7.65 (5H, m).

Compound 59b (X═Cl)

Similarly, compound 59b was prepared.

Under nitrogen at 0° C., to a stirred suspension of compound 58b (5 g, 16.3 mmol) in 150 ml of methanol, was added portionwise sodium borohydride (0.50 g, 13 mmol). After 3 h, the reaction mixture was quenched with water (20 mL) and methanol was evaporated. The aqueous residue was neutralized with HCl 2N and extracted with CH$_2$Cl$_2$. The organic layer was dried over MgSO$_4$, concentrated and purified by flash chromatography (petroleum ether/dichloromethane 50/50) to give 3.1 g (yield=62%) of compound 59b (white powder).

$^1$H NMR (400 MHz, DMSO-d$_6$) δ 7.57–7.43 (5H, m), 7.26 (1H, s), 7.23 (1H, s), 5.36 (1H, t), 3.96 (2H, d).

Synthesis of 3-phenylindol-2-ylmethanol 62

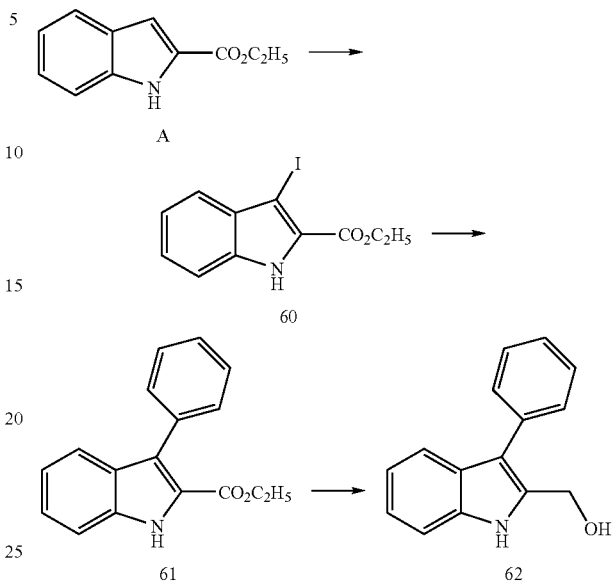

Compound 60: Ethyl 3-iodoindole-2-carboxylate

A 1 L round-bottom flask containing a magnetic stirring bar equipped with a reflux condenser was charged with 10 g (0.053 mol) of ethyl indole-2-carboxylate (A), 100 mL DMF, 50 mL of water, 30 g (0.106 mol) of iodine and 6.6 g (0.106 mol) of potassium hydroxide. The resulting mixture was heating at 70° C. for 3 hours. 500 mL of ice was poured into this flask, and the mixture was agitating for an hour. After filtration and drying, we obtained 15 g (315.1 g.mol$^{-1}$) of expected compound 60.

Yield: 90%.

1H NMR (400 MHz, CDCl3) δ 1.45 (3H, t) 4.48 (2H, q) 7.22 (1H, q) 7.38 (2H, m) 7.57 (1H, q) 9.23 (1H, bs).

Compound 61: Ethyl 3-phenylindole-2-carboxylate

A 250 mL round-bottom flask containing a magnetic stirring bar equipped with a reflux condenser was charged with 4.8 g (0.0152 mol) of B, 100 mL of toluol, 1.6 g (10%) of palladium tetrakis, 50 mL of ethanol, 2.0 g (0.0167 mol) of phenylboronic acid, 50 mL of water and 5 g of potassium carbonate. The resulting mixture was refluxed for 48 hours. At room temperature, 100 mL of water was added, the mixture was extracted with 2×100 mL of toluol. The organic layer was dried with magnesium sulfate, filtered and evaporated to dryness. The crude mixture was then triturated in 20 mL of diethyl ether and filtered. We obtained 4 g (265.31 g.mol$^{-1}$) of the expected compound 61.

Yield: 99%.

1H NMR (400 MHz, CDCl$_3$) δ 1.23 (3H, t) 4.29 (2H, q) 7.15 (1H, m) 7.36 (2H, m) 7.43 (2H, m) 7.45 (2H, m) 7.55 (1H, m) 7.63 (1H, m) 8.99 (1H, m).

Compound 62: 3-phenylindol-2-yl-methanol

A 250 mL round-bottom flask containing a magnetic stirring bar equipped with a reflux condenser was charged with 1.4 g of C (0.0053 mol) and 100 mL of dry THF. At room temperature, 10 mL of LiAlH$_4$ (1M in THF) were added slowly over 15 minutes. The mixture was stirring for 15 minutes and then 20 mL of crude ice was added. HCl (1M) was added until pH=1. The solution was evaporated to dryness. To the crude mixture obtained was added 50 mL of water. The expected product was extracted with 3×50 mL of ethyl acetate. The organic layer was dried over magnesium sulfate, filtered and evaporated to dryness. The product was purified by chromatographic column with ethyl acetate as eluant. We obtained 0.8 g (223.27 g.mol$^{-1}$) of compound 62.

Yield: 68%.

1H NMR (400 MHz, CDCl$_3$) δ 1.83 (1H, bs) 4.94 (2H, s) 7.14 (2H, m) 7.23 (2H, m) 7.25 (1H, m) 7.38 (2H, m) 7.47 (2H, m) 7.72 (1H, m) 8.53 (1H, bs).

3) Synthesis of Compounds Ia

Example 1

Compound Ia:
dibenzofuran-2-ylmethylsulfanyl-acetic acid ethyl ester

To a solution of dibenzofuran (2.5 g, 14.9 mmol), ethyl chloromethylthioacetate (2.5 g, 14.8 mmol) [prepared according to Synthesis, 1984, 326] in 20 mL CH$_2$Cl$_2$, SnCl$_4$ (1.8 ml, 15.4 mmol) was added at 0° C. under N$_2$. The reaction was concentrated after 10 minutes at 0° C. and the residue was purified by flash chromatography (cyclohexane/ ethyl acetate, 5/1) to afford 2.8 g of Example 1 as a colorless oil.

1H NMR (400 MHz, CHCl$_3$) δ 1.25 (3H, t), 3.1 (2H, s), 3.9 (2H, s), 4.15 (2H, q), 7.25 (1H, t), 7.4 (2H, m), 7.45 (1H, d), 7.5 (1H, d), 7.83 (1H, s), 7.87 (1H, d).

Example 2

Compound Ia:
dibenzofuran-2-ylmethylsulfanyl-acetic acid

Preparation from Example 1 Scheme A Route A

Example 1 (10 g, 33.3 mmol) was dissolved in 80 mL of methanol, 80 mL of THF and 40 mL of H$_2$O, then LiOH monhydrate (3.1 g, 73.8 mmol) was added. The mixture was stirred at room temperature for 2 days. After solvants evaporation, water was added and the resulting solution acidified to pH 2. The precipitate was filtered, washed with water and dried under vacuum to afford 8.7 g of Example 2 as a white solid.

1H NMR (400 MHz, DMSO-d$_6$) δ 3.2 (2H, s), 4.0 (2H, s), 7.4 (1H, t), 7.47 (1H, dd), 7.5 (1H, t), 8.05 (1H, s), 8.15 (1H, d).

Preparation via Scheme A Route B

Thioacetamide (30 g, 0.4 M) was added to a solution of compound 1 (prepared as described earlier on) in 900 mL CHCl$_3$. The mixture was refluxed for 2 h. The resulting suspension was cooled, filtered, washed with CH$_2$Cl$_2$, dried under vacuum to afford 33 g of compound E wherein Ar correspond to 2-dibenzofuryl as an off-white solid.

A suspension of compound E (20.3 g, 60.4 mmol) in 23 mL 32% NaOH and 30 mL water was heated at 70° C., then a solution of chloroacetic acid (6.4 g, 68 mmol) in 4.5 mL 32% NaOH and 25 mL water was added to give a viscous suspension which was diluted with 50 mL water. The mixture was refluxed for 1 h, diluted with 500 mL of water, acidified with concentrated HCl until pH 2. The suspension was filtered and the crude product washed with water, dried under vacuum to afford 15.4 g of Example 2 as a white solid.

1H NMR (400 MHz, DMSO-d$_6$) δ 3.2 (2H, s), 4.0 (2H, s), 7.4 (1H, t), 7.47 (1H, dd), 7.5 (1H, t), 8.05 (1H, s), 8.15 (1H, d).

Example 3

Compound Ia:
2-(8-chlorodibenzofuran-2-yl-methylsulfanyl) acetic acid

To a solution of thiourea (3 g, 39.5 mmol) in 48% HBr (25 mL), in an heated bath (100° C.), 8-chloro-2-hydroxymethyldibenzofuran 45 (6.76 g, 29 mmol) was added portionwise. The mixture was diluted with water (20 mL), heated to 110° C. for 1 h 40 minutes, cooled, then filtered. The precipitate was washed with water, dried at 50° C. under vacuum to give 10.4 g of thiouronium hydrobromide as an off-white solid. This compound (8.4 g, 22.6 mmol) was treated in 32% NaOH (20 ml) at 90° C., diluted with water (30 mL), then a solution of chloroacetic acid (2.5 g, 26.5 mmol), NaHCO$_3$ (2.3 g, 27.4 mmol) in water (20 mL) was added. The mixture was refluxed for 1 h, cooled, acidified with concentrated HCl at 5° C. The crude product was filtered, washed with water, dried under vacuum to afford 6.8 g of pure 8-chlorodibenzofuran-2-yl-methylsulfanic acid (Example 3) as a white solid.

1H NMR (400 MHz, CHCl$_3$) δ 3.13 (2H, s), 4.05 (2H, s), 7.4 (1H, dd), 7.5 (3H, m), 7.91 (2H, d).

Example 4

Compound Ia: 2-(fluoren-4-ylmethylsulfanyl)acetic acid

To a solution of thiourea (4.2 g, 55.3 mmol) in 48% HBr (25 ml) heated in a bath of 80° C., was added Compound 13 (9 g, 45.9 mmol) to give a thick suspension which was diluted with 15 ml of water. The resultant mixture was refluxed for 10 minutes, then cooled, filtered, washed with water to give a beige solid.

A mixture of above obtained compound in 16% NaOH (40 ml) was heated at 70° C., then a solution of chloroacetic acid (5 g, 52.9 mmol) in 1N NaOH (50 ml) was added. The resulting mixture was heated at reflux for 90 minutes, filtered while hot, the filtrate was cooled and acidified by concentrated HCl to pH 2 to give a suspension that was filtered, washed by water, dried in vacuum to afford 9 g of pure Example 4 as a brownish solid.

1H NMR (400 MHz, DMSO-d$_6$) δ: 3.25 (2H, s), 3.97 (2H, s), 4.25 (2H, s), 7.25 (2H, m), 7.33 (1H, t), 7.43 (1H, t), 7.53 (1H, d), 7.6 (1H, d), 8.0 (1H, d).

Example 5

Compound Ia:
2-(2-dibenzothiophen-methylsulfanyl)acetic acid

To a solution of thiourea (4.7 g, 61.8 mmol) in 48% HBr (30 ml) heated in a bath of 80° C., was added Compound 19 (10.7 g, 50 mmol) to give a very thick suspension which was diluted with 30 ml of 48% HBr and 20 ml water. The resultant mixture was refluxed for 2 hr, then cooled, filtered, washed with water, dried to give 17.3 of white solid.

The above obtained compound was mixed with 32% NaOH (25 ml) and 20 ml water, heated at 70° C., then a solution of sodium chloroacetate (6 g, 51.5 mmol) in water (50 ml) was added to give a solution. The resulting mixture was heated at reflux for 60 minutes, cooled, diluted by water (200 ml) and acidified by concentrated HCl to pH 2 to give a suspension that was extracted by methylenechloride, the organic phase was washed by brine, dried over $Na_2SO_4$, evaporated to afford 13 g of pure Example 5 as a yellowish solid.

1H NMR (400 MHz, DMSO-$d_6$) δ: 3.2 (2H, s), 4.0 (2H, s), 7.5 (3H, m), 8.0 (1H, d), 8.03 (1H, m), 8.28 (1H, s), 8.33 (1H, m).

Example 6

Compound Ia:
2-(8-fluorodibenzofuran-2-yl-methylsulfanyl)acetic acid

To a solution of thiourea (3.7 g, 48.7 mmol) in 48% HBr (45 ml) heated in a bath of 80° C., was added 8-fluoro-2-hydroxymethyldibenzofuran 44 (8.4 g, 38.9 mmol) to give a very thick suspension which was diluted with 15 ml water. The resultant mixture was refluxed for 2 hr, then cooled, filtered, washed with water, dried to give a white solid.

The above obtained compound was mixed with 32% NaOH (20 ml), heated at 70° C., then a solution of sodium chloroacetate (4.7 g, 40.3 mmol) in water (40 ml) was added to give a suspension. The resulting mixture was heated at reflux for 60 minutes, cooled, diluted by water (500 ml) and acidified by concentrated HCl to pH 2 to give a suspension that was filtered, rinsed with water dried in vacuum to afford 11 g of pure Example 6 as a beige solid.

1H NMR (400 MHz, DMSO-$d_6$) δ: 3.18 (2H, s), 4.0 (2H, s), 7.35 (1H, dt), 7.5 (1H, d), 7.66 (1H, d), 7.75 (1H, dd), 8.0 (1H, d), 8.03 (1H, dd), 8.1 (1H, s).

Example 7

Compound Ia: (3-phenyl-benzo[b]thiophen-2-ylmethylsulfanyl)-acetic acid

To a mixture of thiourea (2.74 g, 36 mmol) and 48% HBr (15.75 mL) in water (3 mL) at 60° C., compound 3 (7.2 g, 30 mmol) was added in one portion was added. The reaction mixture was then gently heated to reflux for 5 nm, cooled. The mixture of HBr and water was decanted from the resulting oil, water was added and decanted again. To the resulting residue, aqueous NaOH (10N, 12 mL) was added, and the mixture heated to 70° C. A solution of sodium chloroacetate (33 mmol) in 9 mL of water was slowly added. The reaction mixture was then heated to 110° C. for 1 h, cooled, diluted with ice-water (100 mL), and acidified with conc. hydrochloric acid (pH~2). The resulting acidic mixture was extracted into diethyl ether (2×150 mL), the separated organic layer was washed with a solution of NaOH (4 N) and the aqueous layer acidified again (pH~2), extracted into diethyl ether (400 mL). The combined organic layers were dried over $Na_2SO_4$, and solvent evaporated to generate 7 g of compound 50 as a yellow oil.

Yield=74%, $R_f$=0.4 (eluent: $CH_2Cl_2/CH_3OH$ 9/1).

In the following examples 8 to 10 compound Ia from example 2, 5 and 6 where R=H were converted into their corresponding compound Ia where R=CH3 (methyl ester).

Example 8

Compound Ia:
2-(dibenzofuran-2-ylmethylsulfanyl)acetic acid methyl ester

A mixture of the Example 2 (4.22 g, 15.5 mmol) in methanol (30 ml) and concentrated $H_2SO_4$ (1 ml) was refluxed for 2 hr and then evaporated. The residue was dissolved in 100 ml methylenechloride, washed by water, dried over $Na_2SO_4$, purified by flash chromatography (cyclohexane/ethyl acetate, 5/1) to furnish 3.7 g of Example 8 as a yellowish oil.

HPLC: Ret. Time=15.92 min (Column: Zorbax Eclipse XDB-C8; 4.6*150 mm, 5 am; Mobile Phase: A: 0.1% TFA in $H_2O$, B: 0.1% TFA in ACN; Gradient: 10~100% B in 20 min.; Flow Rate: 1 ml/min.; Temperature: 25° C.)

1H NMR (400 MHz, $CHCl_3$) δ 3.1 (2H, s), 3.75 (3H, s), 3.9 (2H, s), 7.25 (1H, t), 7.4 (2H, m), 7.45 (1H, d), 7.5 (1H, d), 7.83 (1H, s), 7.87 (1H, d).

Example 9

Compound Ia:
2-(dibenzothiophen-2-ylmethylsulfanyl) acetic acid methyl ester

A mixture of the Example 5 (2.88 g, 10 mmol) in methanol (30 ml) and concentrated $H_2SO_4$ (1 ml) was heated at reflux for 2 hr, then evaporated, the residue was dissolved in 100 ml methylenechloride, washed by water, dried over $Na_2SO_4$, purified by flash chromatography (cyclohexane/ethyl acetate, 5/1) to furnish 2.72 g of Example 9 as a yellowish oil.

1H NMR (400 MHz, $CHCl_3$) δ 3.11 (2H, s), 3.75 (3H, s), 4.3 (2H, s), 7.5 (3H, m), 7.81 (1H, d), 7.84 (1H, m), 8.13 (1H, s), 8.18 (1H, m).

Example 10

Compound Ia:
2-(8-fluorodibenzofuran-2-ylmethylsulfanyl) acetic acid methyl ester A mixture of the Example 6 (2.9 g, 10 mmol) in methanol (30 ml) and concentrated $H_2SO_4$ (1 ml) was heated at reflux for 2 hr, then evaporated, the residue was dissolved in 100 ml methylenechloride, washed by water, dried over $Na_2SO_4$, purified by flash chromatography (cyclohexane/ethyl acetate, 5/1) to furnish 2.34 g of Example 10 as a colorless oil.

1H NMR (400 MHz, $CHCl_3$) δ 3.11 (2H, s), 3.75 (3H, s), 4.3 (2H, s), 7.5 (3H, m), 7.81 (1H, d), 7.84 (1H, m), 8.13 (1H, s), 8.18 (1H, m).

Example 11

Compound Ia:
2-(8-methoxydibenzofuran-2-ylmethylsulfanyl) acetic acid ethyl ester (Synthesis: Route D)

To a solution of compound 46 (5.48 g, 24 mmol) in methylenechloride (120 ml), were added at RT ethyl thioglycolate (3.1 g, 25.8 mmol) and $ZnI_2$ (8.5 g, 26.6 mmol) to give a suspension. The reaction was stirred at RT for 2 hr, quenched by water, the organic phase was dried over Na$_2$SO$_4$, evaporated, the residue was purified by flash chromatography (cyclohexane/ethyl acetate, 6/1) to furnish 3.58 g of Example 11 as a colorless oil.

HPLC: Ret. Time=16.66 min (the same conditions as described for Example 8

Example 12

Compound Ia: 2-(2-benzofuran-2-yl-benzylsulfanyl) acetic acid ethyl ester

To a solution of compound 7 (3.18 g, 14.2 mmol) in methylenechloride (30 ml), were added at RT ethyl thioglycolate (1.75 g, 14.6 mmol) and ZnI$_2$ (4.7 g, 14.7 mmol) to give a suspension. The reaction was stirred at RT for 1 hr, quenched by water, the organic phase was dried over Na$_2$SO$_4$, evaporated, the residue was purified by flash chromatography (cyclohexane/ethyl acetate, 8/1) to furnish 3 g of Example 12 as a colorless oil.

1H NMR (400 MHz, CHCl$_3$) δ 1.25 (3H, t), 3.25 (2H, s), 4.13 (2H, q), 4.25 (2H, s), 7.3 (2H, m), 7.4 (1H, t), 7.5 (3H, t), 7.75 (1H, d), 7.86 (2H, d).

Example 13

Compound Ia: wherein Ar is 3-phenyl-1,4 benzodioxin, Y is CH$_2$, q is 0, substitution in position 2 and R$^1$ is COOCH$_3$ To a solution of (3-phenyl-1,4-benzodioxin-2-yl)methanol (compound C; 7.60 g, 31.6 mmol) in dichloroethane (200 mL) under N$_2$, was added successively methyl thioglycolate (3.35 g, 31.6 mmol) and ZnI$_2$ (10.08 g, 31.6 mmol). The mixture was stirred at room temperature for 2 h 30 and then 60 mL of water was added. After decantation, the aqueous layer was extracted with dichloromethane (100 mL). The organic layers were dried over MgSO$_4$ and concentrated to furnish 10.2 g of Example 13 (yellow oil).

Yield=98%,
$^1$H-NMR (400 MHz, CDCl$_3$): δ 3.35 (2H, s), 3.47 (2H, s), 3.59 (3H, s), 6.7–6.9 (4H, m), 7.3–7.6 (5H, m).

4) Synthesis of Compounds Ib

Example 14

Compound Ib: 2-(dibenzofuran-2-ylmethylsulfinyl)acetic acid

To a solution of Example 2 (13.6 g, 50 mmol) in acetic acid (130 mL), was added 30% H$_2$O$_2$ (8 mL, 79 mmol). The mixture was stirred at room temperature for 3 h. the obtained suspension was filtered, washed with acetic acid (50 mL) and methanol (50 mL), dried under vacuum to afford 12.5 g of Example 14 as a white solid.

1H NMR (400 MHz, DMSO-d$_6$) δ 3.6 (1H, d), 3.9 (1H, d), 4.25 (1H, d), 4.45 (1H, d), 7.45 (1H, t), 7.5 (1H, d), 7.65 (1H, t), 7.75 (2H, m), 8.1 (1H, s), 8.2 (1H, d).

5) Synthesis of Compounds Ic

Example 15

Compound Ic wherein Ar is dibenzofuran-2-yl, Y is CH$_2$, q is 0, NR$^{12}$R$^{13}$=4-(2-hydroxyethyl)piperazin-1-yl To a mixture of Example 2 (0.5 g, 1.8 mmol), N-(2-hydroxyethyl)piperazine (0.25 g, 1.9 mmol), HOBt (0.25 g, 18.5 mmol) in 50 ml methylenechloride was added EDCI (0.46 g, 2.4 mmol) at RT. The reaction was maintained for 16 h, then washed with water, dried over MgSO$_4$, evaporated, the residue was chromatographied (methylenechloride/methanol, 10/1) to furnish 0.5 g of Example 16 as a colorless oil which crystallized on stand.

1H NMR (400 MHz, CHCl$_3$) δ 2.5 (6H, m), 3.2 (2H, s), 3.45 (2H, m), 3.65 (4H, m), 4.0 (2H, s), 7.35 (1H, t), 7.5 (4H, m), 7.95 (1H, d), 7.98 (1H, s).

Example 16

Compound Ic: 2-(dibenzofuran-2-ylmethylsulfanyl)acetamide

A mixture of Example 8 (3.7 g, 12.9 mmol) in methanol (100 ml) and 28% aqueous ammonia (50 ml) was stirred at RT for 16 hr to give a suspension that was filtered, washed by water, dried in vacuum to furnish 2.7 g of Example 16 as a white solid.

1H NMR (400 MHz, DMSO-d$_6$) δ 3.04 (2H, s), 4 (2H, s), 7.03 (1H, bs), 7.6 (4H, m), 7.7 (2H, dd), 8.08 (1H, s), 8.13 (1H, d).

Example 17

Compound Ic: 2-(8-methoxy-dibenzofuran-2-ylmethylsulfanyl)acetamide

A mixture of Example 11 (1.1 g, 3.3 mmol) in ethanol (20 ml) and 28% aqueous ammonia (30 ml) was stirred at RT for 18 hr to give a suspension that was filtered, washed by water, dried in vacuum to furnish 0.71 g of example 17 as a white solid.

HPLC: Ret. Time=11.68 min. (the same conditions as described for Example 8)

Example 18

Compound Ic: 2-(dibenzothiophen-2-ylmethylsulfanyl)acetamide

A mixture of Example 9 (2.72 g, 9 mmol) in methanol (50 ml) and 28% aqueous ammonia (30 ml) was stirred at room temperature for 16 hr to give a suspension. After evaporation of methanol, the aqueous residue was filtered, washed by water, dried in vacuum to furnish 2.1 g of Example 18 as a white solid.

1H NMR (400 MHz, DMSO-d$_6$) δ 3.04 (2H, s), 4 (2H, s), 7.03 (1H, bs), 7.5 (4H, m), 7.91 (2H, d), 8.02 (1H, m), 8.3 (1H, s), 8.33 (1H, m).

Example 19

Compound Ic: 2-(8-fluorodibenzofuran-2-ylmethylsulfanyl)acetamide

A mixture of Example 10 (2.34 g, 7.7 mmol) in methanol (50 ml) and 28% aqueous ammonia (30 ml) was stirred at room temperature for 16 hr to give a suspension. The methanol was evaporated and the aqueous residue was filtered, washed by water, dried in vacuum to furnish 1.68 g of Example 19 as a white solid.

1H NMR (400 MHz, DMSO-d$_6$) δ 3.04 (2H, s), 4 (2H, s), 7.03 (1H, bs), 7.35 (1H, dt), 7.43 (1H, bs), 7.5 (1H, d), 7.67 (1H, d), 7.75 (1H, dd), 8.01 (1H, dd), 8.1 (1H, s).

Example 20

Compound Ic: 2-(2-benzofuran-2-yl-benzylsulfanyl)-N,N-dimethyl acetamide

To a mixture of Example 12 (1.12 g, 3.43 mmol) and dimethylamine hydrochloride (0.3 g, 3.68 mmol) in methylenechloride (20 ml) was added at RT a 2 N solution of Al(CH$_3$)$_3$ in toluene (2 ml, 4 mmol). The resulting mixture was stirred at RT for 24 hr, then quenched by 0.1 N HCl (20 ml), the organic phase was washed by water, dried over MgSO$_4$, purified by flash chromatography (Methylenechloride/methanol, 40/1) to furnish 1 g of Example 20 as a yellowish oil.

1H NMR (400 MHz, CHCl$_3$) δ 2.95 (6H, d), 3.4 (2H, s), 4.25 (2H, s), 4.7 (1H, d), 7.3 (2H, m), 7.4 (1H, t), 7.5 (3H, t), 7.75 (1H, dd), 7.88 (2H, d).

Example 21

Compound Ic: 2-(8-chlorodibenzofuran-2-yl-methylsulfanyl)-1-[4-(2-hydroxyethyl)piperazin-1-yl]ethanone To a mixture of Example 3 (1.48 g, 4.8 mmol), 4-(2-hydroxyethyl)-piperazine (0.65 g, 5 mmol) and HOBt (0.65 g, 4.8 mmol) in methylenechloride (50 ml), was added EDCI (1.2 g, 6.25 mmol) at RT. The reaction was maintained at RT for 16 hr, quenched by water, the organic phase was washed by water, dried over Na$_2$SO$_4$, evaporated to give 1.92 g of pure Example 21.

HPLC: Ret. Time=10.7 min. (the same conditions as described for Example 8)

Example 22

Compound Ic: 4-[2-(8-chlorodibenzofuran-2-yl-methylsulfanyl)acetyl]-piperazine-1-carboxylic acid tret-butyl ester To a mixture of Example 3 (2 g, 6.5 mmol), 4-(tert-butoxycarbonyl)-piperazine (1.3 g, 7 mmol) and HOBt (1.2 g, 8.9 mmol) in methylenechloride (50 ml), was added EDCI (1.7 g, 8.9 mmol) at RT. The reaction was maintained at RT for 1.5 hr, quenched by water, the organic phase was washed by water, dried over Na$_2$SO$_4$, evaporated, the residue was purified by flash chromatography (Methylenechloride/methanol, 40/1) to give 2.75 g of Example 22 as a white solid.

1H NMR (400 MHz, CHCl$_3$) δ 1.5 (9H, s), 3.25 (2H, s), 3.45 (6H, m), 3.59 (2H, m), 4.0 (2H, s), 7.4 (1H, dd), 7.5 (3H, m), 7.96 (2H, d).

Example 23

Compound Ic: 1-(4-acetyl-piperazin-1-yl)-2-(8-chlorodibenzofuran-2-yl-methylsulfanyl)-ethanone To a mixture of acid Example 3 (1.83 g, 6 mmol), 4-(acetyl)-piperazine (0.8 g, 6.3 mmol) and HOBt (1 g, 4.8 mmol) in methylenechloride (50 ml), was added EDCI (1.5 g, 7.8 mmol) at RT. The reaction was maintained at RT for 5 hr, quenched by water, the organic phase was washed by water, dried over Na$_2$SO$_4$, evaporated, the residue was purified by flash chromatography (methylenechloride/methanol, 30/1) to give 2.14 g of Example 23.

HPLC: Ret. Time=12.81 min. (the same conditions as described for Example 8)

Example 24

Compound Ic: 2-(9H-fluoren-4-ylmethylsulfanyl)-1-[4-(2-hydroxyethyl)-piperazin-1-yl]-ethanone To a mixture of acid Example 4 (6 g, 22.2 mmol), 4-(2-hydroxyethyl)-piperazine (3 g, 23 mmol) and HOBt (2.5 g, 18.5 mmol) in methylenechloride (200 ml), was added EDCI (4.6 g, 24 mmol) at RT. The reaction was maintained at RT for 2 hr, quenched by water, the organic phase was washed by water, dried over Na$_2$SO$_4$, evaporated, the residue was purified by flash chromatography (methylenechloride/methanol, 10/1) to give 6.26 g of Example 24.

1H NMR (400 MHz, CHCl$_3$) δ 2.43 (2H, m), 2.5 (4H, m), 3.3 (2H, s), 3.38 (2H, t), 3.63 (4H, m), 3.58 (2H, s), 3.97 (2H, s), 4.28 (2H, s), 7.25 (1H, m), 7.33 (2H, m), 7.41 (1H, t), 7.48 (1H, d), 7.57 (1H, d), 7.88 (1H, d).

Example 25

Compound Ic: 4-[2-(dibenzothiophen-2-ylmethylsulfanyl)-acetyl]-piperazine-1-carboxylic acid tert-butyl ester To a mixture of acid Example 5 (5.76 g, 20 mmol), 4-(tert-butoxycarbonyl)-piperazine (3.75 g, 20.2 mmol) and HOBt (3.4 g, 25 mmol) in methylenechloride (150 ml), was added EDCI (4.8 g, 25 mmol) at RT. The reaction was maintained at RT for 3 hr, quenched by water, the organic phase was washed by 0.5 N HCl, water, dried over Na$_2$SO$_4$, evaporated, the residue was purified by flash chromatography (cyclohexane/ethyl acetate, 3/4) to give 8.3 g of Example 25 as a white solid.

1H NMR (400 MHz, CHCl$_3$) δ 1.5 (9H, s), 3.25 (2H, s), 3.45 (6H, m), 3.59 (2H, m), 4.0 (2H, s), 7.45 (3H, m), 7.8 (1H, d), 7.87 (1H, m), 8.16 (1H, s), 8.19 (1H, m).

Example 26

Compound Ic: 4-[2-(8-fluorodibenzofuran-2-yl-methylsulfanyl)acetyl]-piperazine-1-carboxylic acid tret-butyl ester To a mixture of acid Example 6 (5.8 g, 20 mmol), 4-(tert-butoxycarbonyl)-piperazine (3.72 g, 20 mmol) and HOBt (3.4 g, 25 mmol) in methylenechloride (150 ml), was added EDCI (4.8 g, 25 mmol) at RT. The reaction was maintained at RT for 1 hr, quenched by water, the organic phase was washed by 0.5 N HCl, water, dried over Na$_2$SO$_4$, evaporated to give a beige solid which was recrystallized in ethyl acetate (30 ml) to give 6.46 g of Example 26 as a beige solid.

1H NMR (400 MHz, CHCl$_3$) δ 1.5 (9H, s), 3.25 (2H, s), 3.45 (6H, m), 3.59 (2H, m), 4.0 (2H, s), 7.18 (1H, dt), 7.45 (3H, m), 7.61 (1H, dd), 7.92 (1H, s).

Example 27

Compound Ic: 2-(3-phenyl-benzo[b]thiophen-2-ylmethylsulfanyl)-1-pyrrolidin-1-yl-ethanone To a cooled (ice-bath) solution of Example 7 (2.14 g, 6.8 mmol) in CH$_2$Cl$_2$ (40 mL), was added successively pyrrolidine (0.63 mL, 7.5 mmol), EDCI (1.44 g, 7.5 mmol) and HOBT (1.012 g, 7.5 mmol). The cooling bath was removed and the mixture was stirred at room temperature for one night, diluted with $CH_2Cl_2$ (50 mL), washed successively with water (50 mL), aqueous $Na_2CO_3$ (50 mL) water (30 mL) and dried over $Na_2SO_4$. On concentration, the solution generated a crude product that was purified by column chromatography ($CH_2Cl_2/CH_3OH$ 9.6/0.4) to give 1.76 g of Example 27 (orange oil).

Yield=70%, $R_f$=0.8(eluent: $CH_2Cl_2/CH_3OH$ 9/1).

The following examples were prepared according to the process as described for Example 27:

Example 28

Compound Ic: N,N-dimethyl-2-(3-phenyl-benzo[b] thiophen-2-ylmethylsulfanyl)-acetamide Reagents: Example 7 (2.14 g, 6.8 mmol) in $CH_2Cl_2$ (40 mL), 40% aqueous dimethylamine (0.337 g, 0.85 mL, 7.5 mmol), EDCI (1.44 g, 7.5 mmol) and HOBT (1.012 g, 7.5 mmol).

Example 28 as a yellow orange oil was directly used in the next step without any further purification.

Yield=96%, $R_f$=0.6 (eluent: $CH_2Cl_2/CH_3OH$ 9.5/0.5).

Example 29

Compound Ic: N-isopropyl-2-(3-phenyl-benzo[b] thiophen-2-ylmethylsulfanyl)-acetamide Reagents: Example 7 (2.14 g, 6.8 mmol) in $CH_2Cl_2$ (40 mL), isopropylamine (0.44 g, 0.65 mL, 7.5 mmol), EDCI (1.44 g, 7.5 mmol) and HOBT (1.012 g, 7.5 mmol).

The crude product was crystallized in diisopropyl oxyde to give 0.62 g of Example 29 (white powder)

Yield=26%.

Rf ($CH_2Cl_2/CH_3OH$ 9/1)=0.8

Example 30

Compound Ic: 1-(4-hydroxy-piperidin-1-yl)-2-(3-phenyl-benzo[b]thiophen-2ylmethylsulfanyl)-ethanone Reagents: Example 7 (2.198 g, 7 mmol) in $CH_2Cl_2$ (40 mL), N-hydroxypiperidine (0.788 g, 7.7 mmol), EDCI (1.474 g, 7.7 mmol) and HOBT (1.039 g, 7.7 mmol).

Yield=39.5%, 1.1 g of Example 30 as a yellow oil.

Rf ($CH_2Cl_2/CH_3OH$ 9/1)=0.5.

Example 31

Compound Ic: 1-(4-acetyl-piperazin-1-yl)-2-(3-phenyl-benzo[b]thiophen-2-ylmethylsulfanyl)-ethanone.

Reagents: Example 7 (3.01 g, 9.6 mmol) in $CH_2Cl_2$ (58 mL), N-acetylpiperazine (1.39 g, 10.86 mmol), EDCI (2.02 g, 10.86 mmol) and HOBT (1.46 g, 10.86 mmol).

The crude product that was purified by column chromatography ($CH_2Cl_2/CH_3OH$ 9.5/0.5) to give 1.38 g of Example 31 (yellow oil)

Yield=34.5.

Rf ($CH_2Cl_2/CH_3OH$ 9.5/0.5)=0.2.

Example 32

Compound Ic N-(2-hydroxy-ethyl)-2-(3-phenyl-benzo[b]thiophen-2-ylmethylsulfanyl)-acetamide Reagents: Example 7 (2.36 g, 7.51 mmol) in $CH_2Cl_2$ (40 mL), ethanolamine (0.506 g, 8.3 mmol), EDCI (1.59 g, 8.3 mmol) and HOBT (1.12 g, 8.3 mmol).

The crude product that was purified by column chromatography ($CH_2Cl_2/CH_3OH$ 9.4/0.6) to give 0.72 g of Example 32 as a solid.

Yield=27%.

Rf ($CH_2Cl_2/CH_3OH$ 9/1)=0.8

Example 33

Compound Ic: 1-[4-(3-Phenyl-benzo[1,4]dioxin-2-ylmethylsulfanylmethyl)-piperazin-1-yl]-ethanone Under $N_2$, to a solution of Example 13 (1.5 g, 4.57 mmol) in dichloromethane (20 mL), were added successively N-acetylpiperazine (0.70 g, 5.48 mmol) in one portion and $AlMe_3$ 2N in toluene (2.74 mL) dropwise. The mixture was stirred at room temperature for one night and then refluxed for 3 h. After cooling, few mL of water was added slowly. After decantation, the organic layer was dried over $MgSO_4$ and concentrated to afford the crude product which was purified by column chromatography ($CH_2Cl_2$/MeOH 98/2) to give 0.78 g (yield=40%) of Example 33 (yellow oil).

$^1$H-NMR (400 MHz, $CDCl_3$): δ 2.11 (3H, d), 3.3–3.7 (12H, m), 6.6–6.9 (4H, m), 7.3–7.6 (5H, m).

6) Synthesis of Compounds Id

Example 34

Compound Id: 4-[2-(dibenzofuran-2-ylmethylsulfinyl)-acetyl]-piperazine-1-carboxylic acid ethyl ester To a mixture of Example 14 (4.32 g, 15 mmol), N-(ethoxycarbony)piperazine (2.5 g, 15.8 mmol) and HOBt (2 g, 15 mmol) in 150 ml methylenechloride, was added EDCI (3.6 g, 18.8 mmol) at RT. The reaction was maintained for 2 h, then washed with 0.5 N HCl (100 ml) and water, dried over $Na_2SO_4$, evaporated to a white solid that was recrystallized in 15 ml ethyl acetate to afford 3.6 g of Example 34 as a white solid; additional 0.85 g of Example 34 were obtained from the filtrate by flash chromatography (methylenechloride/methanol, 10/1).

1H NMR (400 MHz, DMSO-$d_6$) δ 1.2 (3H, t), 3.35 (4H, m), 3.5 (4H, m), 4.0 (4H, m), 4.2 (1H, d), 4.45 (1H, d), 7.45 (1H, t), 7.5 (1H, d), 7.6 (1H, t), 7.75 (2H, dd), 8.1 (1H, s), 8.2 (1H, d).

MS: M+H=429, M+Na=451, M+K=467

7) Synthesis of Compounds Id

Example 35

Compound Id: 2-(dibenzofuran-2-ylmethylsulfinyl)-1-[4-(2-hydroxyethyl)-piperazin-1-yl]-ethanone To a solution of Example 15 (0.5 g, 1.3 mmol) in 20 ml acetic acid, was added 30% $H_2O_2$ (0.2 ml, 2 mmol) was added. The oxidation was maintained at RT for 18 h, then evaporated, the residue was purified by flash chromatography (methylenechloride/methanol, 9/1) to afford 0.39 g of Example 34 as a white solid.

1H NMR (400 MHz, CHCl$_3$) δ 2.5 (6H, m), 3.4 (2H, m), 3.65 (6H, m), 4.25 (1H, d), 4.5 (1H, d), 7.33 (1H, t), 7.5 (2H, m), 7.6 (1H, d), 7.92 (1H, d), 7.98 (1H, s).

MS: MS: M+H=401, M+Na=423

Example 36

Compound Id: 2-(dibenzofuran-2-ylmethylsulfinyl)acetamide

A mixture of Example 16 (2.7 g, 10 mmol) in acetic acid (40 ml) and 30% H$_2$O$_2$ (1.6 ml) was stirred at RT for 1.5 hr to give a solution that was evaporated to give white solid. The crystallization in ethanol (30 ml) furnished 2.6 g of Example 36 as a white solid.

1H NMR (400 MHz, DMSO-d$_6$) δ 3.43 (1H, d), 3.68 (1H, d), 4.17 (1H, d), 4.43 (1H, d), 7.33 (1H, bs), 7.43 (1H, t), 7.47 (1H, d), 7.54 (1H, t), 7.68 (1H, bs), 7.73 (2H, m), 8.07 (1H, s), 8.17 (1H, d).

MS: M+Na=310

Example 37

Compound Id: 2-(8-methoxydibenzofuran-2-ylmethylsulfinyl)acetamide

A mixture of Example 17 (0.71 g, 2.36 mmol) in acetic acid (20 ml) and 30% H$_2$O$_2$ (0.45 ml) was stirred at RT for 1 hr to give a solution that was evaporated to give an oil. The crystallization in ethanol furnished 0.48 g of Example 37 as a white solid.

1H NMR (400 MHz, DMSO-d$_6$) δ 3.46 (1H, d), 3.69 (1H, d), 3.87 (3H, s), 4.17 (1H, d), 4.41 (1H, d), 7.1 (1H, dd), 7.33 (1H, bs), 7.46 (1H, d), 7.59 (1H, d), 7.69 (3H, m), 8.06 (1H, s).

MS: M+Na=340

Example 38

Compound Id: 2-(8-fluorodibenzofuran-2-ylmethylsulfinyl)acetamide

A mixture of Example 19 (1.68 g, 5.8 mmol) in acetic acid (30 ml) and 30% H$_2$O$_2$ (0.9 ml) was stirred at RT for 3 hr to give a solution that was evaporated to give an oil. The crystallization in ethanol (30 ml) furnished 1.36 g of Example 38 as a white powder.

1H NMR (400 MHz, DMSO-d$_6$) δ 3.46 (1H, d), 3.69 (1H, d), 4.18 (1H, d), 4.43 (1H, d), 7.38 (2H, m), 7.53 (1H, d), 7.75 (3H, m), 8.03 (2H, m), 8.1 (1H, s).

MS: M+Na=328

Example 39

Compound Id: 2-(dibenzothiophen-2-ylmethylsulfinyl)acetamide

A mixture of Example 18 (2.1 g, 7.3 mmol) in acetic acid (40 ml) and 30% H$_2$O$_2$ (1.1 ml) was stirred at RT for 2.5 hr to give a solution that was evaporated to give an oil. The crystallization in ethanol (50 ml) furnished 1.45 g of Example 39 as a beige solid.

1H NMR (400 MHz, DMSO-d$_6$) δ 3.5 (1H, d), 3.75 (1H, d), 4.2 (1H, d), 4.48 (1H, d), 7.36 (1H, bs), 7.5 (1H, d), 7.54 (2H, m), 7.75 (1H, bs), 8.03 (2H, d), 8.28 (1H, s), 8.33 (1H, m).

MS: M+Na=326

Example 40

Compound Id: 2-(8-chlorodibenzofuran-2-yl-methanesulfinyl)-[4-(2-hydroxyethyl)piperazin-1-yl]ethanone A mixture of Example 21 (1.92 g, 4.6 mmol) in acetic acid (40 ml) and 30% H$_2$O$_2$ (0.85 ml) was stirred at RT for 2 hr, then evaporated to give a solid which was dissolved in methylenehloride (100 ml) and water (50 ml). The mixture was alkalized to pH 10 by 1 N NaOH. The organic phase was washed by water, dried over Na$_2$SO$_4$, purified by flash chromatography (methylenechloride/methanol, 9/1) to give 1.2 g Example 40 as a white solid.

1H NMR (400 MHz, CDCl$_3$) δ 2.5 (6H, m), 3.47 (2H, m), 3.66 (5H, m), 3.74 (1H, m), 4.25 (1H, d), 4.5 (1H, d), 7.43 (1H, dd), 7.5 (2H, m), 7.58 (1H, d), 7.92 (2H, d).

MS: M+H=435, M+Na=457

Example 41

Compound Id: 2-(8-chlorodibenzofuran-2-yl-methanesulfinyl)-1-piperazin-1-ylethanone A mixture of Example 22 (2.67 g, 5.6 mmol) in methylenechloride (15 ml) and trifluoroacetic acid (7 ml) was stirred at RT for 0.5 h, then evaporated to dryness. The residue was dissolved in 20 ml water and 20 ml methylenechloride, then neutralized to pH 8 by NaHCO$_3$ powder, the organic phase was washed by water, dried over Na$_2$SO$_4$, evaporated to give the deprotected intermediate which was mixed with acetic acid (40 ml) and 30% H$_2$O$_2$ (1 ml). The mixture was stirred at RT for 2 hr. evaporated, purified by flash chromatography (methylenechloride/methanol, 10/1 saturated by 28% aqueous ammonia) followed by crystallization in 10 ml ethyl acetate to give 1.95 g Example 41 as a white solid.

1H NMR (400 MHz, DMSO-d$_6$) δ 2.5 (4H, m), 3.25 (4H, m), 3.87 (2H, dd), 4.07 (1H, d), 4.31 (1H, d), 7.43 (2H, m), 7.63 (2H, dd), 8.0 (1H, s), 8.2 (1H, s).

MS: M+H=391, M+Na=413

Example 42

Compound Id: 1-(4-acetylpiperazin-1-yl)-2-(8-chlorodibenzofuran-2-yl-methanesulfinyl)-ethanone A mixture of Example 23 (2.1 g, 5 mmol) in acetic acid (30 ml) and 30% H$_2$O$_2$ (0.8 ml) was stirred at RT for 2 hr, then diluted with 300 ml water to give a suspension that was heated to give a solution, cooled, filtered, rinsed with water, dried in vacuum to give 1.78 g Example 42 as a white solid.

1H NMR (400 MHz, CDCl$_3$) δ 2.16 (3H, d), 3.4~3.83 (10H, m), 4.25 (1H, dd), 4.5 (1H, dd), 7.43 (1H, dd), 7.5 (2H, m), 7.59 (1H, d), 7.91 (1H, s), 7.96 (1H, d).

MS: M+H=433, M+Na=455

Example 43

Compound Id: 2-(9H-fluoren-4-ylmethanesulfinyl)-1-[4-(2-hydroxyethyl)piperazin-1-yl]-ethanone A mixture of Example 24 (2.9 g, 7.6 mmol) in acetic acid (40 ml) and 30% $H_2O_2$ (1.2 ml) was stirred at RT for 3 hr, then evaporated. The residue was dissolved in 50 ml water and neutralized at pH 7 by $K_2CO_3$ powder to give a solution that was extracted methylenechloride (3*50 ml). The extracts were washed by brine, dried over $Na_2SO_4$, evaporated. Flash chromatography (methylenechloride/methanol, 9/1) followed by recrystallization in ethyl acetate/methylenechloride (10/1) afforded 2 g Example 43 as a white crystal.

1H NMR (400 MHz, $CDCl_3$) δ 2.5 (7H, m), 3.43 (2H, m), 3.61 (4H, m), 3.69 (1H, d), 3.86 (1H, d), 3.92 (2H, s), 4.61 (1H, d), 4.91 (1H, d), 7.3 (2H, m), 7.4 (2H, m), 7.56 (2H, m), 8.0 (1H, d).

MS: M+H=399, M+Na=421, M+K=437

Example 44

Compound Id: 2-(dibenzothiophen-2-yl-methanesulfinyl)-1-piperazin-1-yl-ethanone

A mixture of Example 25 (2 g, 4.4 mmol) in methylenechloride (20 ml) and trifluoroacetic acid (8 ml) was stirred at RT for 0.5 h, then evaporated to dryness. The residue was dissolved in 50 ml water and 20 ml methylenechloride, then neutralized to pH 8 by 0.5 N NaOH, the organic phase was washed by water, dried over $Na_2SO_4$, evaporated to give the deprotected intermediate which was mixed with acetic acid (30 ml) and 30% $H_2O_2$ (0.8 ml). The mixture was stirred at RT for 1.5 hr, evaporated, purified by flash chromatography (methylenechloride/methanol, 10/1 saturated by 28% aqueous ammonia) to give 0.6 g Example 44 as a white solid.

1H NMR (400 MHz, $CDCl_3$) δ 2.81 (2H, m), 2.87 (2H, m), 3.36 (2H, m), 3.63 (4H, m), 4.28 (1H, d), 4.5 (1H, d), 7.46 (3H, m), 7.86 (2H, m), 8.17 (2H, m).

MS: M+H=373, M+Na=395

Example 45

Compound Id: 2-(8-fluorodibenzofuran-2-yl-methanesulfinyl)-1-piperazin-1-ylethanone A mixture of Example 26 (6.4 g, 14 mmol) in methylenechloride (40 ml) and trifluoroacetic acid (20 ml) was stirred at RT for 0.5 h, then evaporated to dryness. The residue was dissolved in 100 ml water and 100 ml methylenechloride, then neutralized to pH 8 by 0.5 N NaOH, the organic phase was washed by water, dried over $Na_2SO_4$, evaporated to give the deprotected intermediate which was mixed with acetic acid (100 ml) and 30% $H_2O_2$ (2.5 ml). The mixture was stirred at RT for 2 hr, evaporated, purified by flash chromatography (methylenechloride/methanol, 15/1 saturated by 28% aqueous ammonia) and recrystallization in 50 ml ethyl acetate to give 4 g Example 45 as a white solid.

1H NMR (400 MHz, DMSO-$d_6$) δ 2.63 (4H, m), 3.25~3.5 (4H, m), 3.96 (2H, dd), 4.2 (1H, d), 4.43 (1H, d), 7.36 (1H, dt), 7.5 (1H, d), 7.75 (2H, m), 8.03 (1H, dd), 8.07 (1H, s).

MS: M+H=375, M+Na=397

Example 46

Compound Id: 2-(2-benzofuran-2-yl-phenyl-methanesulfinyl)-N,N-dimethyl acetamide A mixture of Example 20 (1 g, 3.1 mmol) in acetic acid (10 ml) and 30% $H_2O_2$ (0.35 ml) was stirred at RT for 4 hr to give a solution that was evaporated. The flash chromatography (methylenechloride/methanol, 20/1) furnished 0.71 g of Example 46 as a white solid.

1H NMR (400 MHz, $CHCl_3$) δ 2.95 (6H, s), 3.9 (2H, dd), 4.47 (1H, d), 4.7 (1H, d), 7.31 (2H, m), 7.43 (1H, m), 7.5 (3H, m), 7.75 (1H, d), 7.93 (2H, d).

MS: M+Na=364.

Example 47

Compound Id: 2-(3-phenyl-benzo[b]thiophen-2-ylmethanesulfinyl)-1-pyrrolidin-1-yl-ethanone To a solution of Example 27 (1.76 g, 4.8 mmol) in glacial acetic acid (5 mL), 35% aqueous hydrogen peroxide (0.5 mL) was added. The mixture was stirred until no more starting material was detected (TLC). After a 3 h-stirring, the reaction mixture was concentrated, the resulting oil was diluted with water and ethyl acetate (50 mL). The organic layer was washed successively with water (25 mL), aqueous $NaHCO_3$ (25 mL), water (25 mL) and dried over $Na_2SO_4$. On concentration, the solution generated a yellow oil that was purified by column chromatography ($CH_2Cl_2$/$CH_3OH$ 9.6/0.4) to give 0.638 g of Example 47 (white meringue; yield=35%).

$^1$H-NMR (DMSO) δ (ppm): 8.05 (d, 1H), 7.6–7.35 (m, 8H), 4.45 (q, 2H), 3.95 (q, 2H), 3.4 (m, 2H), 3.25 (m, 2H) 1.9–1.7 (m, 4H).

MS: M+H=384

The following examples were prepared according to the process as described for Example 47: following Scheme B Step 3 Pathway E

Example 48

Compound Id: N,N-dimethyl-2-(3-phenyl-benzo[b]thiophen-2-ylmethanesulfinyl)-acetamide Reagents: Example 28 (2.24 g, 6.5 mmol) in glacial acetic acid (6.5 mL) and 35% aqueous hydrogen peroxide (0.66 mL).

The crude product that was purified by column chromatography ($CH_2Cl_2$/$CH_3OH$ 9.6/0.4) to give 0.38 g of Example 48 (white meringue; yield=16.4%).

$^1$H-NMR (DMSO) δ (ppm): 8.05 (d, 1H), 7.6–7.35 (m, 8H), 4.45 (q, 2H), 4.05 (s, 2H), 2.95 (s, 3H), 2.8 (s, 3H).

MS: M+Na=380, 2M+Na=737

Example 49

Compound Id: N-isopropyl-2-(3-phenyl-benzo[b]thiophen-2-ylmethanesulfinyl)-acetamide Reagents: Example 29 (0.62 g, 1.8 mmol) in glacial acetic acid (5 mL) and 35% aqueous hydrogen peroxide (0.2 mL).

Solvent evaporation generated a yellow oil that crystallized slowly on standing. The residue was stirred with diisopropyl oxide, filtered and dried in vacuo to give 0.48 g of Example 49 (white powder; yield=72%).

¹H-NMR (DMSO) δ (ppm): 8.2 (d, 1H), 8.05 (d, 1H), 7.55–7.35 (m, 8H), 4.4 (q, 2H), 3.8 (h, 1H), 3.65 (q, 2H), 1 (t, 6H).
MS: M+Na=394, M+K=410

Example 50

Compound Id: -(4-hydroxy-piperidin-1-yl)-2-(3-phenyl-benzo[b]thiophen-2ylmethanesulfinyl)ethanone Reagents: Example 30 (1.1 g, 2.77 mmol) in glacial acetic acid (3 mL) and 35% aqueous hydrogen peroxide (0.3 mL).

The crude product that was purified by column chromatography ($CH_2Cl_2/CH_3OH$ 9.5/0.5) to give ⁻0.625 g of Example 50 (white meringue; yield=56%).

¹H-NMR (DMSO) δ (ppm): 8.05 (d, 1H), 7.6–7.35 (m, 8H), 4.75 (t, 1H), 4.4 (q, 2H), 4.2–4 (m, 2H), 3.85 (m, 1H), 3.75–3.55 (m, 2H), 3.2 (m, 1H), 3.05 (m, 1H), 1.7 (m, 2H), 1.4 (m, 1H), 1.25 (m, 1H).
MS: M+H=414

Example 51

Compound Id: 1-(4-acetyl-piperazin-1-yl)-2-(3-phenyl-benzo[b]thiophen-2-ylmethanesulfinyl)-ethanone Reagents: Example 31 (1.38 g, 3.25 mmol) in glacial acetic acid (4 mL) and 35% aqueous hydrogen peroxide (0.34 mL).

The crude product that was purified by column chromatography ($CH_2Cl_2/CH_3OH$ 9.2/0.8) to give 1.01 g of Example 50 (white meringue; yield=70%).

¹H-NMR (DMSO) δ (ppm): 8.05 (d, 1H), 7.6–7.35 (m, 8H), 4.45 (q, 2H), 4.15 (q, 2H), 3.4 (m, 8H), 2 (s, 3H).
MS: M+Na=463

Example 52

Compound Id N-(2-hydroxy-ethyl)-2-(3-phenyl-benzo[b]thiophen-2-ylmethanesulfinyl)-acetamide Reagents: Example 32 (0.72 g, 2 mmol) in glacial acetic acid (3 mL) and 35% aqueous hydrogen peroxide (0.23 mL).

The crude product was purified by column chromatography ($CH_2Cl_2/CH_3OH$ 9.2/0.8) to give after washing in diisopropyl oxyde 0.478 g of Example 52 (white powder; yield=64%).

¹H-NMR (DMSO) δ (ppm): 8.25 (t, 1H), 8.05 (d, 1H), 7.6–7.35 (m, 8H), 4.7 (t, 1H), 4.4 (q, 2H), 3.7 (q, 2H), 3.4 (m, 2H), 3.15 (m, 2H)
MS: M+Na=396

Example 53

Compound Id: 1-[4-(3-Phenyl-benzo[1,4]dioxin-2-ylmethanesulfinylmethyl)-piperazin-1-yl]-ethanone To a solution of Example 33 (0.78 g, 1.84 mmol) in 3.6 mL of acetic acid, was added 30% aqueous hydrogen peroxide (0.20 mL). After 4 h of stirring at room temperature, the mixture was neutralized with aqueous $NaHCO_3$ and then extracted with $CH_2Cl_2$ (2×70 mL). The organic layer was dried over $MgSO_4$ and concentrated to afford the crude product which was purified by column chromatography ($CH_2Cl_2$/MeOH 98/2) to give 0.60 g (yield=74%) of Example 53 (white powder).

¹H-NMR (400 MHz, $CDCl_3$): δ 2.10 (3H, d), 3.3–4.1 (12H, m), 6.6–6.9 (4H, m), 7.3–7.7 (5H, m).
MS: M+Na=463; M+K=479

Examples 54 through 150 were prepared following the same multistep general method as described in scheme B utilizing the appropriate substituted amine-$NR^{12}R^{13}$ in Steps 2 or 3. The analytical data as well as the synthetic pathway used are presented by each compounds molecular formula and masse spectrum (M+H) or (M+Na) are shown in the following Table 2.

TABLE 2

| Example n° | MF | MS | SYNTHETIC PATHWAY |
|---|---|---|---|
| 54 | $C_{17}H_{17}NO_3S$ | M + H = 316 | A |
|  |  | M + Na = 338 |  |
| 55 | $C_{19}H_{19}NO_3S$ | M + H = 342 | A |
|  |  | M + Na = 364 |  |
| 56 | $C_{18}H_{19}NO_3S$ | M + H = 330 | A |
|  |  | M + Na = 352 |  |
| 57 | $C_{19}H_{20}N_2O_3S$ | M + H = 357 | C |
|  |  | M + Na = 379 |  |
| 58 | $C_{21}H_{22}N_2O_4S$ | M + H = 399 | C |
|  |  | M + Na = 421 |  |
| 59 | $C_{17}H_{17}NO_4S$ | M + Na = 354 | C |
| 60 | $C_{20}H_{21}NO_4S$ | M + H = 372 | C |
|  |  | M + Na = 394 |  |
| 61 | $C_{19}H_{21}NO_5S$ | M + Na = 398 | C |
|  |  | M + K = 414 |  |
| 62 | $C_{20}H_{20}N_2O_4S$ | M + H = 385 | C |
|  |  | M + Na = 407 |  |
|  |  | M + K = 423 |  |
| 63 | $C_{24}H_{28}N_2O_5S$ | M + H = 457 | D |
|  |  | M + Na = 479 |  |
| 64 | $C_{20}H_{22}N_2O_3S$ | M + H = 371 | D |
|  |  | M + Na = 393 |  |
| 65 | $C_{21}H_{24}N_2O_3S$ | M + H = 385 | D |
|  |  | M + Na = 407 |  |
| 66 | $C_{22}H_{26}N_2O_3S$ | M + H = 399 | D |
|  |  | M + Na = 421 |  |
| 67 | $C_{19}H_{20}N_2O_4S$ | M + H = 373 | D |
|  |  | M + Na = 395 |  |
|  |  | M + K = 411 |  |
| 68 | $C_{19}H_{21}NO_4S$ | M + H = 360 | D |
|  |  | M + Na = 382 |  |
|  |  | M + K = 398 |  |
| 69 | $C_{19}H_{19}NO_4S$ | M + H = 358 | D |
|  |  | M + Na = 380 |  |
|  |  | M + K = 396 |  |
| 70 | $C_{19}H_{18}N_2O_4S$ | M + H = 371 | D |
| 71 | $C_{23}H_{27}N_3O_4S$ | M + H = 442 | D |
|  |  | M + Na = 464 |  |
| 72 | $C_{20}H_{21}N_3O_4S$ | M + H = 400 | D |
| 73 | $C_{24}H_{27}N_3O_4S$ | M + H = 454 | D |
| 74 | $C_{22}H_{25}N_3O_4S$ | M + H = 428 | D |
| 75 | $C_{27}H_{26}N_2O_5S$ | M + H = 491 | D |
| 76 | $C_{16}H_{15}NO_3S$ | M + H = 302 | C |
| 77 | $C_{20}H_{22}N_2O_3S$ | M + H = 371 | C |
|  |  | M + Na = 393 |  |
| 78 | $C_{22}H_{24}N_2O_4S$ | M + H = 413 | D |
| 79 | $C_{22}H_{24}N_2O_4S$ | M + H = 413 | D |
|  |  | M + Na = 435 |  |
| 80 | $C_{21}H_{24}N_2O_3S$ | M + H = 385 | C |
| 81 | $C_{22}H_{26}N_2O_3S$ | M + H = 399 | C |
| 82 | $C_{21}H_{24}N_2O_4S$ | M + H = 401 | C |
| 83 | $C_{14}H_{12}O_2S$ | M + H = 245 |  |
|  |  | M + Na = 267 |  |
| 84 | $C_{19}H_{19}N_2O_3SCl$ | M + H = 391 | E |
|  |  | M + Na = 413 |  |
| 85 | $C_{21}H_{21}N_2O_4SCl$ | M + H = 433 | E |
|  |  | M + Na = 455 |  |
| 86 | $C_{15}H_{12}NO_3SCl$ | M + Na = 344 | E |
| 87 | $C_{20}H_{22}N_2O_4S$ | M + H = 387 | E |
|  |  | M + Na = 409 |  |
| 88 | $C_{22}H_{24}N_2O_5S$ | M + Na = 451 | E |
|  |  | M + K = 467 |  |

TABLE 2-continued

| Example n° | MF | MS | SYNTHETIC PATHWAY |
|---|---|---|---|
| 89 | $C_{21}H_{21}N_2O_4SF$ | M + H = 417 | E |
|  |  | M + Na = 439 |  |
| 90 | $C_{15}H_{12}NO_3SCl$ | M + Na = 344 | E |
| 91 | $C_{15}H_{12}NO_3SF$ | M + Na = 328 | E |
| 92 | $C_{21}H_{21}N_2O_4SCl$ | M + H = 433 | E |
|  |  | M + Na = 455 |  |
| 93 | $C_{21}H_{21}N_2O_4SF$ | M + H = 417 | E |
|  |  | M + Na = 439 |  |
| 94 | $C_{21}H_{20}N_2O_4SClF$ | M + Na = 362 | E |
|  |  | 2M + Na = 701 |  |
| 95 | $C_{17}H_{17}NO_4S$ | M + Na = 354 | E |
| 96 | $C_{15}H_{13}NO_3S$ | M + Na = 310 | E |
| 97 | $C_{21}H_{22}N_2O_4S$ | M + Na = 421 | E |
|  |  | M + K = 437 |  |
| 98 | $C_{20}H_{21}NO_4S$ | M + Na = 394 | E |
|  |  | M + K = 410 |  |
| 99 | $C_{19}H_{20}N_2O_3S$ | M + H = 357 | E |
| 100 | $C_{21}H_{24}N_2O_3S$ | M + H = 385 | E |
| 101 | $C_{22}H_{24}N_2O_4S$ | M + H = 413 | F |
|  |  | M + Na = 435 |  |
| 102 | $C_{22}H_{26}N_2O_3S$ | M + H = 399 | E |
| 103 | $C_{21}H_{24}N_2O_4S$ | M + H = 401 | E |
| 104 | $C_{21}H_{24}N_2O_4S$ | M + H = 401 | E |
|  |  | M + Na = 423 |  |
| 105 | $C_{19}H_{20}N_2O_3S$ | M + H = 357 | E |
|  |  | M + Na = 379 |  |
| 106 | $C_{19}H_{20}N_2O_3S$ | M + H = 357 | E |
|  |  | M + Na = 379 |  |
| 107 | $C_{21}H_{22}N_2O_4S$ | M + H = 399 | E |
|  |  | M + Na = 421 |  |
| 108 | $C_{21}H_{22}N_2O_3S_2$ | M + H = 415 | E |
|  |  | M + Na = 437 |  |
| 109 | $C_{22}H_{24}N_2O_4S_2$ | M + H = 445 | E |
|  |  | M + Na = 467 |  |
| 110 | $C_{21}H_{22}N_2O_3S_2$ | M + H = 415 | E |
|  |  | M + Na = 437 |  |
| 111 | $C_{18}H_{19}NO_3S$ | M + H = 330 | E |
|  |  | M + Na = 352 |  |
| 112 | $C_{22}H_{24}N_2O_3S$ | M + H = 397 | E |
|  |  | M + Na = 419 |  |
| 113 | $C_{21}H_{23}NO_3S$ | M + H = 370 | E |
|  |  | M + Na = 392 |  |
| 114 | $C_{16}H_{15}NO_3S$ | M + Na = 308 | E |
|  |  | M + K = 324 |  |
| 115 | $C_{22}H_{26}N_2O_3S$ | M + H = 399 | E |
|  |  | M + Na = 421 |  |
| 116 | $C_{20}H_{22}N_2O_2S$ | M + H = 355 | E |
|  |  | M + Na = 377 |  |
| 117 | $C_{16}H_{15}NO_2S$ | M − H = 284 | E |
|  |  | M + Na = 308 |  |
| 118 | $C_{18}H_{19}NO_2S$ | M + H = 314 | E |
|  |  | M + Na = 336 |  |
| 119 | $C_{20}H_{21}NO_2S$ | M + H = 340 | E |
|  |  | M + Na = 362 |  |
| 120 | $C_{19}H_{21}NO_2S$ | M + H = 328 | E |
|  |  | M + Na = 350 |  |
| 121 | $C_{18}H_{19}NO_3S$ | M + Na = 352 | E |
|  |  | M + K = 368 |  |
| 122 | $C_{21}H_{23}NO_3S$ | M + H = 370 | E |
|  |  | M + Na = 392 |  |
| 123 | $C_{22}H_{24}N_2O_3S$ | M + Na = 419 | E |
| 124 | $C_{16}H_{15}NO_2S$ | M + H = 286 | E |
| 125 | $C_{18}H_{19}NO_2S$ | M + H = 314 | E |
| 126 | $C_{19}H_{2}NO_2S$ | M + Na = 328 | E |
| 127 | $C_{18}H_{19}NO_3S$ | M + Na = 352 | E |
| 128 | $C_{21}H_{23}NO_3S$ | M + H = 370 | E |
|  |  | M + Na = 392 |  |
| 129 | $C_{22}H_{24}N_2O_3S$ | M + H = 397 | E |
|  |  | M + Na = 419 |  |
| 130 | $C_{20}H_{22}N_2O_2S$ | M + H = 355 | E |
|  |  | M + Na = 377 |  |
| 131 | $C_{21}H_{22}N_2O_3S$ | M + H = 383 | E |
|  |  | M + Na = 405 |  |
|  |  | M + K = 421 |  |
| 132 | $C_{17}H_{15}NO_3S$ | M + Na = 336 | G |
| 133 | $C_{21}H_{21}NO_3S$ | M + H = 368 | G |
|  |  | 2M + Na = 757 |  |
| 134 | $C_{18}H_{17}NO_3S$ | M + Na = 350 | G |
| 135 | $C_{22}H_{23}NO_3S$ | M + H = 382 | G |
|  |  | M + Na = 404 |  |
| 136 | $C_{20}H_{21}NO_3S$ | M + H = 356 | G |
|  |  | M + Na = 378 |  |
| 137 | $C_{20}H_{21}NO_3S$ | M − H = 354 | G |
|  |  | M + Na = 378 |  |
| 138 | $C_{21}H_{23}NO_3S$ | M + H = 370 | G |
|  |  | M + Na = 392 |  |
| 139 | $C_{23}H_{24}N_2O_4S$ | M + H = 425 | G |
|  |  | M + Na = 427 |  |
|  |  | M + K = 463 |  |
| 140 | $C_{24}H_{26}N_2O_4S$ | M + Na = 461 | G |
| 141 | $C_{17}H_{15}NO_2S_2$ | M + Na = 352 | G |
| 142 | $C_{20}H_{21}NO_4S$ | M + Na = 394 | G |
|  |  | M + K = 410 |  |
| 143 | $C_{17}H_{15}NO_4S$ | M + Na = 352 | G |
|  |  | 2M + Na = 681 |  |
| 144 | $C_{17}H_{13}Cl_2NO_4S$ | M + Na = 420 | G |
|  |  | 2M + Na = 817 |  |
| 145 | $C_{23}H_{22}Cl_2N_2O_5S$ | M + Na = 531 | G |

Example 146

Compound Id: 1-(4-acetyl-piperazin-1-yl)-2-(8-chloro-dibenzofuran-2-ylmethanesulfonyl)-ethanone To a solution of Example 23 (1 g, 2.4 mmol) in acetic acid (15 ml) and TFA (1.5 ml), was added 30% $H_2O_2$ (0.8 ml, 7.8 mmol). The mixture was stirred at 50° C. for 5 h, then evaporated to dryness. Water (100 ml) was added and heated at 80° C. to give a suspension that was filtered while hot, rinsed by water, dried in vacuum at 50° C. The crude product was recrystallized in acetonitrile (30 ml) and water (5 ml) to give 0.79 g of Example 146 as a white solid.

1H NMR (400 MHz, DMSO-$d_6$) δ 2.0 (3H, s), 3.5 (8H, m), 4.5 (2H, d), 4.8 (2H, d), 7.65 (2H, t), 7.75 (2H, m), 8.2 (1H, s), 8.35 (1H, s).

MS: M+Na=471

Were also synthetized according to Pathway G (Scheme B):

Example 147

Compound Ia: Ethyl 2-{[(3-phenyl-1H-indol-2-yl)methyl]sulfanyl}acetate

A 250 mL round-bottom flask containing a magnetic stirring bar equipped with a reflux condenser was charged with 1.6 g (0.00717 mol) of compound 62, 0.8 mL (0.00717 mol) of thioglycolic acid and 50 mL of 1,2-dichloroethane. At 0° C., 1.4 mL (0.0107 mol) of $BF_3.Et_2O$ dissolved in 10 mL of 1,2-dichloroethane was added slowly. The resulting mixture was stirred for 15 minutes and then 100 mL of water and 10 mL of HCl (1N) were added. The product was extracted with 2×50 mL of ethyl acetate. The organic layer was dried over magnesium sulfate, filtered and evaporated to dryness. The crude product was used for the next step (preparation of Example 18).

Example 148

Compound Ic: 2-{[(3-phenyl-1H-indol-2-yl)methyl]sulfanyl}acetamide

A 250 mL round-bottom flask containing a magnetic stirring bar equipped with a reflux condenser was charged with the crude ester Example 147, 100 mL of ethanol and 50 mL of an aqueous solution of $NH_3$ (28%). The mixture was stirred for 5 days and then evaporated to dryness. After chromatographic purification (ethyl acetate/petroleum ether: 9/1), we obtained 0.6 g (296.38 g.mol_1) of Example 148.

1H NMR (400 MHz, $CDCl_3$) δ 3.16 (2H, s) 4.03 (2H, s) 5.52 (1H, bs) 5.93 (1H, bs) 7.12 (1H, m) 7.20 (1H, m) 7.25 (1H, m) 7.39 (2H, m) 7.42 (2H, m) 7.54 (1H, m) 8.29 (1H, bs).

Example 149

Compound Id: 2-{[(3-phenyl-1H-indol-2-yl)methyl]sulfinyl}acetamide

A 100 mL round-bottom flask containing a magnetic stirring bar equipped with a reflux condenser was charged with 0.6 g (0.00202 mol) of Example 148, 50 mL of methanol, 10 mL of water and 0.48 g (0.00223 mol) of sodium periodate. The reaction mixture was stirred for 16 hours at 0° C. After evaporation to dryness, the resulting mixture was treated with 100 mL of water, triturated for 30 minutes, filtered and dried. Were obtained 0.50 g (312.38 g.mol⁻1) of the expected Example 149.

Yield: 79%.

1H NMR (400 MHz, $CDCl_3$) δ 3.34 (2H, s) 3.67 (1H, dd) 4.34 (1H, dd) 7.04 (1H, m) 7.16 (1H, m) 7.32 (1H, m) 7.39 (1H, bs) 7.47 (3H, m) 7.55 (1H, m) 7.75 (2H, m) 11.45 (1H, bs). m/z 335 [M+Na⁺], m/z 351 [M+K⁺].

8) Synthesis of Compounds Ia, Ib and Ic via Scheme B Pathway I

Example 150

Compound Ic: 2-(7-chlorodibenzofuran-1-ylmethyl-sulfanyl)acetamide

To a solution of 7-chloro-1-bromomethyl-dibenzofuran (compound 1b; 7.63 g, 25.9 mmole) in 80 ml of DMF, were added ethyl thioglycolate (2.75 g, 25.94 mmole) and potassium carbonate (4 g, 29 mmole). The mixture was kept at 40–50° C. for 30 minutes. Water (500 mL) was added to give a suspension which was extracted by 2×100 mL dichloromethane, the extracts were washed by water, dried over sodium sulfate, evaporated to give 8.9 g of 2-(7-chlorodibenzofuran-1-ylmethylsulfanyl)acetic acid ethyl ester (compound Ia). This compound is pure enough for the next step without further purification.

A suspension of 2-(7-chlorodibenzofuran-1-ylmethylsulfanyl)acetic acid ethyl ester (Compound Ic; 3.77 g, 11.8 mmole) in 50 ml 7N methanol/ammonia was stirred at 45° C. for one hour, and then at RT for 2 days. The suspension was filtered, washed by methanol, dried in vacuum to give 2.56 g of white solid.

1H NMR (400 MHz, DMSO-$d_6$) δ 3.1 (2H, s), 4.37 (2H, s), 7.1 (1H, bs), 7.33 (1H, d), 7.5 (3H, m), 7.67 (1H, d), 7.93 (1H, s), 8.2 (1H, d).

Example 151

Compound Id: 2-(7-chlorodibenzofuran-1-ylmethyl-sulfinyl)acetamide

To a suspension of 2-(7-chlorodibenzofuran-1-ylmethylsulfanyl)acetamide (Example 151 2.56 g, 8.38 mmole) in acetic acid (90 mL), were added 1.4 mL of 35% hydrogen peroxide (14.4 mmole). The mixture was heated at 50° C. for 30 minutes to give a solution, then stirred at RT for 24 hours to give a thick suspension which was filtered, washed by ethanol, ether, dried in vacuum to give 2 g of white solid.

1H NMR (400 MHz, DMSO-$d_6$) δ 3.7 (1H, d), 3.93 (1H, d), 4.6 (1H, d), 4.72 (1H, d), 7.37 (1H, d), 7.45 (2H, m), 7.57 (1H, t), 7.75 (1H, d), 7.78 (1H, bs), 7.93 (1H, s), 8.32 (1H, d).

MS: M+Na=344, 2M+Na=665

Examples 153 through 154 were prepared following the same multistep general method as described in scheme B utilizing the appropriate substituted amine —$NR^{12}R^{13}$ in Steps 2 and 3. The analytical data as well as the synthetic pathway used are presented by each compounds molecular formula and masse spectrum (M+H) or (M+Na) are shown in the following Table 3.

TABLE 3

| Example n° | MF | MS | SYNTHETIC PATHWAY |
|---|---|---|---|
| 153 | $C_{15}H_{12}ClNO_3S$ | M + Na = 344<br>2M + Na = 665 | I |
| 154 | $C_{15}H_{11}Cl_2NO_3S$ | M + Na = 378<br>2M + Na = 735 | I |

Biological Data

Methodology: Evaluation of Wake Promoting Activity in Rats

The methodology utilized for evaluating wake promoting activity of test compounds is based on that described by Edgar and Seidel, *Journal of Pharmacology and Experimental Therapeutics*, 283:757–769, 1997, and incorporated herein in its entirety by reference.

Animal Surgery. Adult, male Wistar rats (275–320 g from Charles River Laboratories, Wilmington, Mass.) were anesthetized (Nembutal, 45 mg/kg, ip.) and surgically prepared with implants for recording of chronic EEG (encephalographic) and EMG (electromyographic) recording. The EEG implants were made from commercially available components (Plastics One, Roanoke, Va.). EEG signals were recorded from stainless steel screw electrodes: 2 frontal (+3.0 mm AP from bregma, ±2.0 mm ML), and 2 occipital (−4.0 mm AP from bregma, ±2.0 mm ML). Two Teflon-coated stainless steel wires were positioned under the nuchal trapezoid muscles for EMG recording. All electrode leads were inserted into a connector pedestal and the pedestal affixed to the skull by application dental acrylic. Antibiotic was administered post surgically and antibiotic cream was applied to the wound edges to prevent infection. At least one week elapsed between surgery and recording.

Recording environment. Postsurgically, rats were housed in pairs in an isolated room. Food and water were available ad libitum, ambient temperature was 21° C., and humidity was 55%. At least 24 hrs prior to recording, they were placed in Nalgene containers (31×31×31 cm) with a wire-grid top, and entry to the room was prohibited during the day of recording except for dosing. The containers were placed on a rack with two shelves, 4 containers per shelf. Fluorescent overhead room lights were set to a 24 hr. light/dark cycle (on at 7 AM, off at 7 PM). Light levels inside the containers were 38 and 25 lux for the top and bottom shelves respectively. Background white-noise (68 db inside the containers) was present in the room to mask ambient sounds.

Data acquisition. EEG and EMG signals were led via cables to a commutator (Plastics One) and then to pre-amplifiers (model 1700, A-M Systems, Carlsborg, Wash.). EEG and EMG signals were amplified (10K and 1K respectively) and bandpass filtered between 0.3 and 500 Hz for EEG and between 10 and 500 Hz for EMG. These signals were digitized at 128 samples per second using ICELUS sleep research software (M. Opp, U. Texas; see Opp, Physiology and Behavior 63:67–74, 1998, and Imeri, Mancia, and Opp, *Neuroscience* 92:745–749, 1999, incorporated by reference herein in their entirety) running under Labview 5.1 software and data acquisition hardware (PCI-MIO-16E-4; National Instruments, Austin, Tex.). On the day of dosing, data was recorded for 6 to 10 hours beginning at 11 AM.

Drug administration and study design. Compounds were evaluated on groups of from 4 to 8 rats carried out over one or two separate test sessions. Each animal was tested with a different compound or vehicle for up to 10 weeks with at least 7 days between successive tests. A vehicle group was included in all experiments, and each animal received vehicle every $4^{th}$ test. Test compounds were suspended in sterile 0.25% methylcellulose (pH=6.2; Upjohn Co., Kalamazoo, Mich.) at 30 mg/mL. Although compounds can be administered at dosages greater than 100 mg/kg and are expected to be active under the selection criteria of data analysis, unless otherwise noted, compounds were administered at a single dose of 100 mg/kg. Dosing was carried out at noon, while the rats were predominantly asleep. Each rat was lifted out of its container, given an intraperitoneal injection in a volume of 5 mL/kg, and replaced. Dosing required approximately 30 sec per rat.

Sleep/wake scoring. Sleep and wake activity were determined manually using ICELUS software. This program displays the EEG and EMG data in blocks of 6 sec along with the EEG frequency spectrum. Arousal state was scored as awake, rapid eye-movement (REM), or slow-wave or non-REM sleep (NREM) according to visual analysis of EEG frequency and amplitude characteristics and EMG activity (Opp and Krueger, 1994; Van Gelder, et al., 1991; Edgar, et al., 1991, 1997; Seidel, et al, 1995, incorporated by reference herein in their entirety). Essentially, waking activity consists of relatively low-amplitude EEG activity with relatively lower power in the frequency band from 0.5–6 Hz, accompanied by moderate to high level EMG activity. In a particular waking state ("theta-waking"), EEG power can be relatively focused in the 6–9 Hz (theta) range, but significant EMG activity is always present. NREM sleep is characterized by relative high-amplitude EEG activity with relatively greater power in the low frequency band from 0.5–6 Hz, accompanied by little or no EMG activity. REM sleep is characterized by moderate and constant amplitude EEG focused in the theta (6–9 Hz) range, similar to waking theta, but with no EMG activity.

Data analysis and statistics. Two basic outcome measures were used to ascertain whether a compound exhibited wake-enhancing activity. The first was the percent time spent awake for each 30 min period following dosing. The second was the total time spent awake in the first 3 hrs following dosing (3 hr AUC; maximum 180 min). For purposes of ascertaining activity of a test compound, wake activity values were compared against corresponding vehicle values. The vehicle values were of two types. The first type was the corresponding within-experiment vehicle, that is, a value for the vehicle group run concurrently with the test compound. A second "reference" vehicle value consisted of the mean 3 hr AUC value calculated from 234 animals in 59 separate experiments carried out during the same time period as the evaluations of the test compounds (mean±SD=69.22±20.12; 95% confidence limits=66.63–71.81). Two-tailed, unpaired t-tests were performed on the wake time values for drug versus vehicle treated animals, and compounds with $p \leq 0.05$ were deemed significantly wake-promoting. A test compound was considered "active" if it met one of the following three criteria.

(i) The 3 hr AUC value for the test compound was significantly greater ($p \leq 0.05$) than the mean wake value for the reference vehicle group (N=234).

(ii) The 3 hr AUC value for the test compound was significantly greater ($p \leq 0.05$) than the corresponding value for the vehicle group within the same experiment.

(iii) One or more of the half-hour wake time values from 0.5 to 2 hrs after dosing was significantly greater ($p \leq 0.05$) in the test compound group than in the corresponding vehicle group within the same experiment.

Results:

Compounds of the inventionn either have demonstrated or are expected to demonstrate utility for wake promoting activity.

As an example, the three-hours AUC values (mean±sem) for the reference vehicle group and for the test compounds are reported Table 4 for Examples 26, 99 and 130. These test compounds were administered by i.p. route at a 100 mg/kg dose and the time-course of the percent time awake as function of time was estimated from 1 hr prior to 5 hours post dosing.

TABLE 4

Mean AUC 0–3 h values (±sem) for the reference vehicle group and for test compounds

| | Vehicle | | Test compound | | |
|---|---|---|---|---|---|
| | Mean | sem | Mean | sem | p |
| Example 26 | 73.6 | 7.7 | 132.0 | 13.2 | 0.002 |
| Example 99 | 53.0 | 3.3 | 129.1 | 17.3 | 0.022 |
| Example 130 | 76.2 | 17.5 | 149.2 | 2.9 | 0.006 |

AUC 0–3 h (% of waiking time × hr) – n = 4 Rats per test compound and 8 rats per control groups.

As compared to the control groups, compounds of Example 26, 99 and 130 produced a significantly greated wakefulness than that observed in the vehicle-treated animals (p<0.05).

REFERENCES

The following references, to the extent that they provide exemplary procedural or other details supplementary to those set forth herein, are specifically incorporated in their entirety herein by reference:

Touret, et al., *Neuroscience Letters,* 189:43–46, 1995.
Van Gelder, R. N. et al., *Sleep* 14:48–55, 1991.
Edgar, D. M., *J. Pharmacol. Exp. Ther.* 282:420–429, 1997.
Edgar and Seidel, *J. Pharmacol. Exp. Ther.,* 283:757–69, 1997.
Hernant et al., *Psychopharmacology,* 103:28–32, 1991.
Lin et al., *Brain Research,* 591:319–326, 1992.

Opp and Krueger, *American Journal of Physiology* 266: R688–95, 1994

Panckeri et al., *Sleep,* 19(8):626–631, 1996.

Seidel, W. F., et al., *J. Pharmacol. Exp. Ther.* 275:263–273, 1995.

Shelton et al., *Sleep* 18(10):817–826, 1995.

Welsh, D. K., et al., *Physiol. Behav.* 35:533–538, 1985.

Utility

The present invention provides a method of treating diseases and conditions in a subject in need thereof comprising administering to said subject a therapeutically effective amount of a compound of formula (I). For example, the compounds of of the present invention are use in the treatment of diseases, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder ("ADHD"), enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

Dosage and Formulation

The compounds of the present invention can be administered for therapeutic purposes by any means that results in the contact of the active agent with the agent's site of action in a subject. The compounds may be administered by any conventional means available for use in conjunction with pharmaceuticals, either as individual therapeutic agents or in a combination with other therapeutic agents, such as, for example, analgesics, or in combination with antidepressants, including but are not limited to tricyclic antidepressants ("TCAs"), Selective Serotonin Reuptake Inhibitors ("SSRIs"), Serotonin and Noradrenaline Reuptake Inhibitors ("SNRIs"), Dopamine Reuptake Inhibitors ("DRIs"), Noradrenaline Reuptake Inhibitors ("NRUs"), Dopamine, Serotonin and Noradrenaline Reuptake Inhibitors ("DSNRIs") and Monoamine Oxidase Inhibitors ("MAOIs) including reversible inhibitors of monoamine oxidase type A (RIMAs). The compounds of the present invention are preferably administered in therapeutically effective amounts for the treatment of the diseases and disorders described herein.

A therapeutically effective amount can be readily determined by the attending diagnostician, as one skilled in the art, by the use of conventional techniques. The effective dose will vary depending upon a number of factors, including the pharmacodynamics of the active agent, the type and extent of progression of the disease or disorder, the age, weight and health of the particular patient, the formulation of the active and its mode and frequency of administration, and the desired effect with a minimization of side effects. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A typical daily dose for adult humans can range from about 1 to about 1000 mg of the active agent, particularly from about 1 to about 400 mg, and including 25, 50, 85, 100, 150, 170, 200, 255, 250, 255, 340, 400, 425, 500, 600, 700, 750, 800, and 900 mg doses, and equivalent doses for a human child.

The compounds may be administered in one or more unit dose forms, and they may be administered in a single daily dose or in two, three or four doses per day. The unit dose ranges from about 1 to about 1000 mg, particlularly from about 1 to about 400 mg, and including 25, 50, 85, 100, 150, 170, 200, 255, 250, 255, 340, 400, 425, 500, 600, 700, 750, 800, and 900 mg unit doses, and equivalent unit doses for a human child. In particular, the unit dosages range from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The active agent may be present in about 0.5–95% by weight of the composition. The excipients are selected on the basis of the chosen route of administration and standard pharmaceutical practice, as described, for example, in *Remington: The Science and Practice of Pharmacy*, 20$^{th}$ ed.; Gennaro, A. R., Ed.; Lippincott Williams & Wilkins: Philadelphia, Pa., 2000.

The compositions can be prepared for administration by oral means, including tablets, pills, powders, capsules, troches and the like; parenteral means, including intravenous, intramuscular, and subcutaneous means; topical or transdermal means, including patches, creams, ointments, lotions, pastes, gels, solutions, suspensions, aerosols, and powders and the like; transmucosal means, including nasal, rectal, vaginal, sublingual and buccal means; ophthalmic or inhalation means. Preferably the compositions are prepared for oral administration, particularly in the form of tablets, capsules or syrups; parenteral administration, particularly in the form of liquid solutions, suspensions or emulsions; intranasal administration, particularly in the form of powders, nasal drops, or aerosols; or for topical use, such as patches, creams, ointments, and lotions.

For oral administration, the tablets, pills, powders, capsules, troches and the like can contain one or more of the following: diluents or fillers such as starch, or cellulose; binders such as microcrystalline cellulose, gelatins, or polyvinylpyrrolidone; disintegrants such as starch or cellulose derivatives; lubricants such as talc or magnesium stearate; glidants such as colloidal silicon dioxide; sweetening agents such as sucrose or saccharin; and flavoring agents such as peppermint or cherry flavoring. Capsules may contain any of the above ingredients, and may also contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers; suspending agents; thickening agents; and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

The compositions of the present invention may be formulated to control and/or delay the release of the active agent(s). Such controlled-, delayed, sustained-, or extended-release compositions are well-known in the art, and may include, for example, reservoir or matrix diffusion products, as well as dissolution systems. Some compositions may utilize, for example biocompatible, biodegradable lactide polymer, lactide/glycolide copolymer, or polyoxyethylene-polyoxypropylene copolymers as excipients.

Preferred embodiments of the invention include the following:

1. A compound of formula (A):

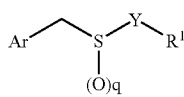
(A)

wherein:
Ar is:

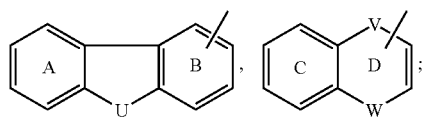

wherein:
U is $CH_2$, $CR^{25}R^{26}$, O, $S(O)_y$, $NR^{10}$, $C(=O)$, $C(=S)$, CHOH, $CHOR^{14}$, $C=NOR^{14}$, or $C=NNR^{12}R^{13}$;

V and W are independently selected from a bond, $CH_2$, $CR^{25}R^{26}$, O, $S(O)_y$, $NR^{10}$, $C(=O)$, $C(=S)$, CHOH, $CHOR^{14}$, $C=NOR^{14}$, or $C=NNR^{12}R^{13}$;

rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1$–$C_6$ alkyl, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$,g and $S(O)_yR^{22}$;

ring D is optionally substituted with one group selected from $C_1$–$C_6$ alkyl, phenyl, and 5–10 membered heteroaryl; provided that when V is a bond, and W is O, $S(O)_y$, or $NR^{10}$, ring D is substituted by a phenyl group;

Y is $C_1$–$C_6$ alkylene; or
$(C_1$–$C_4$ alkylene$)_m$-Z-$(C_1$–$C_4$ alkylene$)_n$;
wherein said alkylene groups are optionally substituted with one to three $R^{20}$ groups;

Z is O, $NR^{10A}$, $S(O)_y$, $CR^{21}=CR^{21}$, C≡C, $C_6$–$C_{10}$ arylene, 5–10 membered heteroarylene, $C_3$–$C_6$ cycloalkylene, or 3–6 membered heterocycloalkylene; wherein said arylene, heteroarylene, cycloalkylene, and heterocycloalkylene groups are optionally substituted with one to three $R^{20}$ groups;

$R^1$ is selected from H, $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, $NR^{21}S(O)_2NR^{12}R^{13}$, and $C(=O)NR^{11}OR^{22}$;

$R^{10}$ and $R^{10A}$ are each independently selected from H, $C_1$–$C_6$ alkyl, $C_6$–$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_1$–$C_6$ alkyl, and $C_6$–$C_{10}$ aryl; wherein said alkyl and aryl groups are optionally substituted with one to three $R^{20}$ groups;

$R^{12}$ and $R^{13}$ at each occurrence are each independently selected from H, $C_1$–$C_6$ alkyl, $C_6$–$C_{10}$ aryl, and $NR^{23}R^{24}$, or $R^{12}$ and $R^{13}$, together with the nitrogen to which they are attached, form a 3–7 membered heterocyclic ring; wherein said alkyl and aryl groups and heterocyclic ring are optionally substituted with one to three $R^{20}$ groups;

$R^{14}$ at each occurrence is independently selected from $C_1$–$C_6$ alkyl, $C_6$–$C_{10}$ aryl, and alkylaryl;
wherein said alkyl, aryl and alkylaryl groups are optionally substituted with one to three $R^{20}$ groups;

$R^{20}$ at each occurrence is independently selected from F, Cl, Br, I, $OR^{22}$, $OR^{27}$, $NR^{23}R^{24}$, NHOH, $NO_2$, CN, $CF_3$, $C_1$–$C_6$ alkyl optionally substituted with OH, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}C(=O)OR^{22}$, $OC(=O)NR^{23}R^{24}$, $NR^{21}C(=S)R^{22}$ and $S(O)_yR^{22}$;

$R^{21}$ at each occurrence is independently selected from H and $C_1$–$C_6$ alkyl;

$R^{22}$ at each occurrence is independently selected from H, $C_1$–$C_6$ alkyl optionally substituted with OH, arylalkyl and $C_6$–$C_{10}$ aryl;

$R^{23}$ and $R^{24}$ at each occurrence are each independently selected from H, $C_1$–$C_6$ alkyl, and $C_6$–$C_{10}$ aryl, or $R^{23}$ and $R^{24}$, together with the nitrogen to which they are attached, form a 3–7 membered heterocyclic ring optionally substituted with =O;

$R^{25}$ and $R^{26}$ at each occurrence are each independently selected from H, $C_1$–$C_6$ alkyl, and $C_6$–$C_{10}$ aryl, or $R^{25}$ and $R^{26}$, together with the carbon to which they are attached, form a 3–7 membered heterocyclic ring;

$R^{27}$ at each occurrence is independently the residue of an amino acid after the hydroxyl group of the carboxyl group is removed;

m is 0 or 1;
n is 0 or 1;
q is 0, 1, or 2;
y is 0, 1, or 2;

with the exclusion of the compounds wherein:
U is $CH_2$, C(=O), $CH(CH_3)$, S or C=NNHPh; and
Y is $CH_2$; and
$R^1$ is H;

and with the exclusion of the compounds wherein:
U is $CH_2$; and
Y is $C_1$–$C_6$ alkylene optionally substituted with $C_1$–$C_6$ alkylene; and
$R^1$ is $CONH_2$, or $CO_2R^{11}$ with $R^{11}$=H or $C_1$–$C_6$ alkyl;

and with the exclusion of the compounds:
3-[(methylthio)methyl]-2-phenyl-1H-inden-1-one
0.3-[(methylsulfinyl)methyl]-2-phenyl-1H-inden-1-one and the stereoisomeric forms, mixtures of stereoisomeric forms or pharmaceutically acceptable salts forms thereof.

2. The compound according to claim 1:

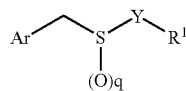

wherein
Y is $C_1$–$C_6$alkylene;
$(C_1$–$C_4$ alkylene$)_m$-$Z^1$-$(C_1$–$C_4$ alkylene$)_n$;
$C_1$–$C_4$ alkylene-$Z^2$-$C_1$–$C_4$ alkylene;
wherein said alkylene groups are optionally substituted with one to three $R^{20}$ groups;
$Z^1$ is $CR^{21}$=$CR^1$, C≡C, $C_6$–$C_{10}$arylene, 5–10 membered heteroarylene, $C_3$–$C_6$ cycloalkylene, or 3–6 membered heterocycloalkylene; wherein said arylene, heteroarylene, cycloalkylene, and heterocycloalkylene groups are optionally substituted with one to three $R^{20}$ groups;
$Z^2$ is O, $NR^{10A}$ or $S(O)_y$;
m is 0 or 1;
n is 0 or 1;
q is 0, 1, or 2;
y is 0, 1, or 2;

and the stereoisomeric forms, mixtures of stereoisomeric forms or pharmaceutically acceptable salts forms thereof.

3. The compound according to any of claims 1 or 2, wherein q is 1.

4. The compound according to any of claims 1 to 3, wherein $R^1$ is H.

5. The compound according to any of claims 1 to 3, wherein $R^1$ is selected from $NR^{12}R^{13}$, $NR^{21}C$(=O)$R^{14}$, C(=O)$R^{14}$, $CO_2R^{11}$, OC(=O)$R^{11}$, C(=O)$NR^{12}R^{13}$, C(=$NR^{11}$)$NR^{12}R^{13}$, OC(=O)$NR^{12}R^{13}$, $NR^{21}S(O)_2R^{11}$, $NR^{21}C$(=O)$NR^{12}R^{13}$, $NR^{21}S(O)_2NR^{12}R^{13}$, and C(=O)$NR^{11}OR^{22}$.

6. The compound according to claim 5, wherein $R^1$ is selected from $NR^{12}R^{13}$, $NR^{21}C$(=O)$R^{14}$; C(=O)$NR^{12}R^{13}$; C(=$NR^{11}$)$NR^{12}R^{13}$, $NR^{21}C$(=O)$NR^{12}R^{13}$.

7. The compound according to claim 6, wherein $R^1$ is C(=O)$NR^{12}R^{13}$.

8. The compound according to any of claims 5 to 7, wherein $R^{12}$ and $R^{13}$ are each independently selected from H, $C_1$–$C_6$ alkyl and $NR^{23}R^{24}$.

9. The compound according to any of claims 5 to 7, wherein $R^{12}$ and $R^{13}$ together with the nitrogen to which they are attached, form a 3–7 membered heterocyclic ring, wherein said heterocyclic ring is optionally substituted with one $R^{20}$ group.

10. The compound according to claim 9, wherein said heterocyclic ring is unsubstituted.

11. The compound according to claim 5, wherein $R^1$ is selected from C(=O)$R^{14}$, $CO_2R^{11}$, OC(=O)$R^{11}$, C(=O)$NR^{12}R^{13}$, OC(=O)$NR^{12}R^{13}$, $NR^{21}S(O)_2R^{11}$, and $NR^{21}S(O)_2NR^{12}R^{13}$;

12. The compound according to any of claims 1 to 11, wherein Ar is:

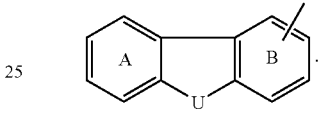

13. The compound according to claim 12, wherein U is $CH_2$, O, $S(O)_y$, or $NR^{10}$.

14. The compound according to claim 13, wherein U is $CH_2$, O or $S(O)_y$.

15. The compound according to any of claims 1 to 11, wherein Ar is:

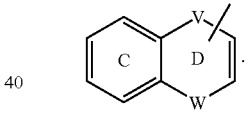

16. The compound according to claim 15, wherein V is O, $S(O)_y$ or $NR^{10}$, W a bond and ring D is substituted with a phenyl.

17. The compound according to claim 15, wherein V is O, W is O and ring D is substituted with a phenyl.

18. The compound according to claims 1 to 17, wherein Y is $C_1$–$C_6$ alkylene.

19. The compound according to claim 18, wherein Y is $CH_2$.

20. The compound according to any of claims 2 to 17, wherein Y is $(C_1$–$C_4$ alkylene$)_m$-$Z^1$-$(C_1$–$C_4$ alkylene$)_n$.

21. The compound according to claim 20, wherein $Z^1$ is $C_6$–$C_{10}$ arylene or $C_3$–$C_6$ cycloalkylene.

22. The compound according to claim 20, wherein $Z^1$ is 5–10 membered heteroarylene or 3–6 membered heterocycloalkylene.

23. The compound according to claim 20, wherein $Z^1$ is $CR^{21}$=$CR^{21}$ or C≡C.

24. The compound according to any of claims 2 to 17, wherein Y is $C_1$–$C_4$ alkylene-$Z^2$-$C_1$–$C_4$ alkylene.

25. The compound according to claim 24, wherein $Z^2$ is O.

26. The compound according to claim 1, with the structure of formula (I):

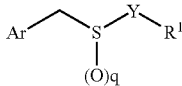

wherein
Ar is:

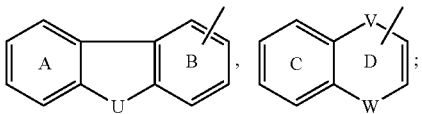

U is $CH_2$, O, $S(O)_y$, or $NR^{10}$;

V and W are independently selected from a bond, O, $S(O)_y$, or $NR^{10}$;

rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1$–$C_6$ alkyl, phenyl, arylalkyl, and $C(=O)R^{22}$;

ring D is optionally substituted with one group selected from $C_1$–$C_6$ alkyl, and phenyl;

Y is $C_1$–$C_6$ alkylene;
$C_1$–$C_4$ alkylene-$Z^1$-($C_1$–$C_4$ alkylene)$_n$;
$C_1$–$C_4$ alkylene-$Z^2$-$C_1$–$C_4$ alkylene;
wherein said alkylene groups are optionally substituted with one to three $R^{20}$ groups;

$Z^1$ is $CR^{21}=CR^{21}$, C≡C, $C_6$–$C_{10}$arylene, 5–10 membered heteroarylene,
$C_3$–$C_6$ cycloalkylene, or 3–6 membered heterocycloalkylene; wherein said arylene, heteroarylene, cycloalkylene, and heterocycloalkylene groups are optionally substituted with one to three $R^{20}$ groups;

$Z^2$ is O, $NR^{10A}$, or $S(O)_y$;

$R^1$ is selected from $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, $NR^{21}S(O)_2NR^{12}R^{13}$, and $C(=O)NR^{11}$ $OR^{22}$;

$R^{10}$ and $R^{10A}$ are each independently selected from H, $C_1$–$C_6$ alkyl, $C(=O)R^{14}$, and $S(O)_yR^{14}$;
wherein said alkyl group is optionally substituted with one to three $R^{20}$ groups;

$R^{11}$ at each occurrence is independently selected from H, and $C_1$–$C_6$ alkyl; wherein said alkyl group is optionally substituted with one to three $R^{20}$ groups;

$R^{12}$ and $R^{13}$ at each occurrence are each independently selected from H, and $C_1$–$C_6$ alkyl, and $NR^{23}R^{24}$, or $R^{12}$ and $R^{13}$, together with the nitrogen to which they are attached, form a 3–7 membered heterocyclic ring; wherein said alkyl group and heterocyclic ring are optionally substituted with one to three $R^{20}$ groups;

$R^{14}$ at each occurrence is independently selected from $C_1$–$C_6$ alkyl and $C_6$–$C_{10}$ aryl; wherein said alkyl, aryl and alkylaryl groups are optionally substituted with one to three $R^{20}$ groups;

$R^{20}$ at each occurrence is independently selected from F, Cl, Br, I, $OR^{22}$, $OR^{27}$, $NR^{23}R^{24}$, NHOH, $NO_2$, CN, $CF_3$, $C_1$–$C_6$ alkyl optionally substituted with OH, phenyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}$ $CO_2R^{22}$, $OC(=O)NR^{23}R^{24}$, $NR^{21}C(=S)R^{22}$, and $S(O)_yR^{22}$;

$R^{21}$ at each occurrence is independently selected from H and $C_1$–$C_6$ alkyl;

$R^{22}$ at each occurrence is independently selected from H. $C_1$–$C_6$ alkyl optionally substituted with OH, phenyl, and benzyl $R^{23}$ and $R^{24}$ at each occurrence are each independently selected from H, $C_1$–$C_6$ alkyl, and $C_6$–$C_{10}$aryl, or $R^{23}$ and $R^{24}$, together with the nitrogen to which they are attached, form a 3–7 membered heterocyclic ring optionally substituted with =O;

$R^{27}$ at each occurrence is independently the residue of an amino acid after the hydroxyl group of the carboxyl group is removed;

n is 0 or 1;

q is 0, 1, or 2;

y is 0, 1, or 2;

and the stereoisomeric forms, mixtures of stereoisomeric forms or pharmaceutically acceptable salts forms thereof.

27. The compound according to claim 26, wherein Y is $C_1$–$C_6$ alkylene, $C_1$–$C_4$ alkylene-$Z^1$-$C_1$–$C_4$ alkylene, or $C_1$–$C_4$ alkylene-$Z^2$-$C_1$–$C_4$ alkylene, wherein said alkylene groups are optionally substituted with one to three $C_1$–$C_6$ alkyl groups;

$Z^1$ is $CR^{21}=CR^{21}$, C≡C, or phenyl;

$Z^2$ is O, $NR^{10A}$, or $S(O)_y$;

$R^1$ is selected from $NR^{21}C(=O)R^{14}$, $C(=O)R^{14}$, $CO_2R^{11}$, $OC(=O)R^{11}$, $C(=O)NR^{12}R^{13}$, and $C(=O)NR^{11}$ $OR^{22}$.

28. The compound according to claim 27, wherein Y is $C_1$–$C_6$ alkylene, or $C_1$–$C_4$ alkylene-$Z^1$-$C_1$–$C_4$ alkylene.

29. The compound according to claim 28, wherein Y is $C_1$–$C_6$alkylene.

30. The compound according to any of claims 26 to 29, wherein $R^1$ is $C(=O)NR^{12}R^{13}$.

31. The compound according to claim 30, having the structure of formula (III):

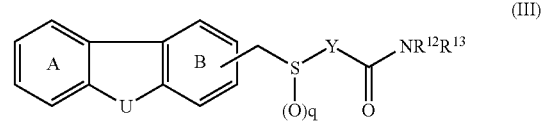

32. The compound according to claim 31, wherein U is $CH_2$, O, or $S(O)_y$.

33. The compound according to claim 32, wherein U is O, or $S(O)_y$.

34. The compound according to claim 32, wherein U is $CH_2$.

35. The compound according to any of claims 31 to 34, wherein Y is $C_1$–$C_6$ alkylene.

36. The compound according to claim 35, wherein Y is $CH_2$, or $CH_2$—$CH_2$.

37. The compound according to any of claims 31 to 34, wherein Y is $C_1$–$C_4$ alkylene-$Z^1$-($C_1$–$C_4$ alkylene), and $Z^1$ is phenylene, 5–6 membered heteroarylene, $CR^{21}=CR^{21}$, or C≡C.

38. The compound according to claim 37, wherein Y is $C_1$–$C_4$ alkylene-$Z^1$-($C_1$–$C_4$ alkylene)$_n$ and $Z^1$ is phenylene, $CR^{21}=CR^{21}$, or C≡C.

39. The compound according to claim 30, having the structure of formula (IV)

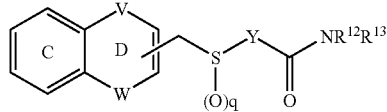

40. The compound according to claim 39, wherein V is O, $S(O)_y$, or $NR^{10}$, W is a bond and ring D is substituted with a phenyl.

41. The compound according to claim 40, wherein V is O, or $S(O)_y$, W is a bond and ring D is substituted with a phenyl.

42. The compound according to claim 39, wherein V is O, W is O and ring D is substituted with a phenyl.

43. The compound according to any of claims 39 to 42, wherein Y is $C_1$–$C_6$ alkylene.

44. The compound according to claim 43, wherein Y is $CH_2$, or $CH_2$—$CH_2$.

45. The compound according to any of claims 39 to 42, wherein Y is $C_1$–$C_4$ alkylene-$Z^1$-$(C_1$–$C_4$ alkylene)$_n$ and $Z^1$ is phenylene, 5–6 membered heteroarylene, $CR^{21}$=$CR^{21}$, or C≡C.

46. The compound according to claim 45, wherein Y is $C_1$–$C_4$ alkylene-$Z^1$-$(C_1$–$C_4$ alkylene)$_n$ and $Z^1$ is phenylene, $CR^{21}$=$CR^{21}$, or C≡C.

47. The compound according to claim 1, selected in accordance with the following table:

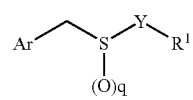

wherein Ar, q, Y—$R^1$ are defined in the table below;

| Ex. n° | Ring Ar | q | Y-R¹ |
|---|---|---|---|
| 16 | Dibenzofuran-2-yl | 0 | $CH_2CONH_2$ |
| 36 | Dibenzofuran-2-yl | 1 | $CH_2CONH_2$ |
|  | Dibenzofuran-2-yl | 0 | $CH_2CON(CH_3)_2$ |
| 54 | Dibenzofuran-2-yl | 1 | $CH_2CON(CH_3)_2$ |
|  | Dibenzofuran-2-yl | 0 | $CH_2CO$-N-pyrrolidinyl |
| 55 | Dibenzofuran-2-yl | 1 | $CH_2CO$-N-pyrrolidinyl |
|  | Dibenzofuran-2-yl | 0 | $CH_2CONHCH(CH_3)_2$ |
| 56 | Dibenzofuran-2-yl | 1 | $CH_2CONHCH(CH_3)_2$ |
|  | Dibenzofuran-2-yl | 0 | $CH_2CO$-1-(4-tert-butoxycarbonyl)-piperazinyl |
| 57 | Dibenzofuran-2-yl | 1 | $CH_2CO$-1-piperazinyl |
|  | Dibenzofuran-2-yl | 0 | $CH_2CO$-1-(4-acetyl)-piperazinyl |
| 58 | Dibenzofuran-2-yl | 1 | $CH_2CO$-1-(4-acetyl)-piperazinyl |
|  | Dibenzofuran-2-yl | 0 | $CH_2CONHCH_2CH_2OH$ |
| 59 | Dibenzofuran-2-yl | 1 | $CH_2CONHCH_2CH_2OH$ |
|  | Dibenzofuran-2-yl | 0 | $CH_2CO$-1-(4-hydroxy)piperidinyl |
| 60 | Dibenzofuran-2-yl | 1 | $CH_2CO$-1-(4-hydroxy)piperidinyl |
|  | Dibenzofuran-2-yl | 0 | $CH_2CONHCH_2CH_2OCH_2CH_2OH$ |
| 61 | Dibenzofuran-2-yl | 1 | $CH_2CONHCH_2CH_2OCH_2CH_2OH$ |
| 15 | Dibenzofuran-2-yl | 0 | $CH_2CO$-1-[4-(2-hydroxyethyl)-piperazinyl] |
| 34 | Dibenzofuran-2-yl | 1 | $CH_2CO$-1-[4-(2-hydroxyethyl)-piperazinyl] |
|  | Dibenzofuran-2-yl | 0 | $CH_2CO$-1-(4-formyl)-piperazinyl |
| 62 | Dibenzofuran-2-yl | 1 | $CH_2CO$-1-(4-formyl)-piperazinyl |
| 63 | Dibenzofuran-2-yl | 1 | $CH_2CO$-1-(4-tert-butoxycarbonyl)-piperazinyl |
| 35 | Dibenzofuran-2-yl | 1 | $CH_2CO$-1-(4-ethoxycarbonyl)-piperazinyl |
| 64 | Dibenzofuran-2-yl | 1 | $CH_2CO$-1-(4-methyl)-piperazinyl |
|  | Dibenzofuran-2-yl | 0 | $CH_2CO$-1-(4-ethyl)-piperazinyl |
| 65 | Dibenzofuran-2-yl | 1 | $CH_2CO$-1-(4-ethyl)-piperazinyl |
|  | Dibenzofuran-2-yl | 0 | $CH_2CO$-1-(4-propyl)-piperazinyl |
| 66 | Dibenzofuran-2-yl | 1 | $CH_2CO$-1-(4-propyl)-piperazinyl |
|  | Dibenzofuran-2-yl | 0 | $CH_2CON$-morpholinyl |
| 67 | Dibenzofuran-2-yl | 1 | $CH_2CON$-morpholinyl |
|  | Dibenzofuran-2-yl | 0 | $CH_2CO$-N-ethyl-N-(2-hydroxy-ethyl) |
| 68 | Dibenzofuran-2-yl | 1 | $CH_2CO$-N-ethyl-N-(2-hydroxy-ethyl) |
|  | Dibenzofuran-2-yl | 0 | $CH_2CONHN$-morpholinyl |
| 69 | Dibenzofuran-2-yl | 1 | $CH_2CONHN$-morpholinyl |
|  | Dibenzofuran-2-yl | 0 | $CH_2CO$-4-(2-oxo-piperazinyl) |
| 70 | Dibenzofuran-2-yl | 1 | $CH_2CO$-4-(2-oxo-piperazinyl) |
| 71 | Dibenzofuran-2-yl | 1 | $CH_2CO$-1-(4-isopropylaminocarbonyl)-piperazinyl |
| 72 | Dibenzofuran-2-yl | 1 | $CH_2CO$-1-(4-aminocarbonyl)-piperazinyl |
| 73 | Dibenzofuran-2-yl | 1 | $CH_2CO$-1-(4-pyrrolidinylcarbonyl)-piperazinyl |
| 74 | Dibenzofuran-2-yl | 1 | $CH_2CO$-1-(4-dimethylaminocarbonyl)-piperazinyl |
| 75 | Dibenzofuran-2-yl | 1 | $CH_2CO$-1-(4-benzyloxycarbonyl)-piperazinyl |
|  | Dibenzofuran-2-yl | 0 | $CH_2CH_2CONH_2$ |
| 76 | Dibenzofuran-2-yl | 1 | $CH_2CH_2CONH_2$ |
|  | Dibenzofuran-2-yl | 0 | $CH_2CH_2CO$-1-piperazinyl-N-Boc |
| 77 | Dibenzofuran-2-yl | 1 | $CH_2CH_2CO$-1-piperazinyl |
| 78 | Dibenzofuran-2-yl | 1 | $CH_2CH_2CO$-1-(4-acetyl)-piperazinyl |

-continued

| Ex. n° | Ring Ar | q | Y-R¹ |
|---|---|---|---|
| 79 | Dibenzofuran-2-yl | 1 | CH$_2$CON-[3-(2-oxo-pyrrolidin-1-yl)-propyl] |
|  | Dibenzofuran-2-yl | 0 | CH$_2$CON-(2-pyrrolidin-1-yl-ethyl) |
| 80 | Dibenzofuran-2-yl | 1 | CH$_2$CON-(2-pyrrolidin-1-yl-ethyl) |
|  | Dibenzofuran-2-yl | 0 | CH$_2$CON-(2-piperidin-1-yl-ethyl) |
| 81 | Dibenzofuran-2-yl | 1 | CH$_2$CON-(2-piperidin-1-yl-ethyl) |
|  | Dibenzofuran-2-yl | 0 | CH$_2$CON-(2-morpholin-4-yl-ethyl) |
| 82 | Dibenzofuran-2-yl | 1 | CH$_2$CON-(2-morpholin-4-yl-ethyl) |
|  | Dibenzofuran-2-yl | 0 | H |
| 83 | Dibenzofuran-2-yl | 1 | H |
|  | 6-Chloro-dibenzofuran-2-yl | 0 | CH$_2$CO-1-piperazinyl-N-Boc |
| 84 | 6-Chloro-dibenzofuran-2-yl | 1 | CH$_2$CO-1-piperazinyl |
|  | 6-Chloro-dibenzofuran-2-yl | 0 | CH$_2$CO-1-(4-acetyl)-piperazinyl |
| 85 | 6-Chloro-dibenzofuran-2-yl | 1 | CH$_2$CO-1-(4-acetyl)-piperazinyl |
| 22 | 8-Chloro-dibenzofuran-2-yl | 0 | CH$_2$CO-1-piperazinyl-N-Boc |
| 41 | 8-Chloro-dibenzofuran-2-yl | 1 | CH$_2$CO-1-piperazinyl |
|  | 8-Chloro-dibenzofuran-2-yl | 0 | CH$_2$CONH$_2$ |
| 86 | 8-Chloro-dibenzofuran-2-yl | 1 | CH$_2$CONH$_2$ |
| 23 | 8-Chloro-dibenzofuran-2-yl | 0 | CH$_2$CO-1-(4-acetyl)-piperazinyl |
| 42 | 8-Chloro-dibenzofuran-2-yl | 1 | CH$_2$CO-1-(4-acetyl)-piperazinyl |
| 146 | 8-Chloro-dibenzofuran-2-yl | 2 | CH$_2$CO-1-(4-acetyl)-piperazinyl |
| 21 | 8-Chloro-dibenzofuran-2-yl | 0 | CH$_2$CO-1-(4-hydroxyethyl)-piperazinyl |
| 40 | 8-Chloro-dibenzofuran-2-yl | 1 | CH$_2$CO-1-(4-hydroxyethyl)-piperazinyl |
| 17 | 8-Methoxy-dibenzofuran-2-yl | 0 | CH$_2$CONH$_2$ |
| 37 | 8-Methoxy-dibenzofuran-2-yl | 1 | CH$_2$CONH$_2$ |
|  | 8-Methoxy-dibenzofuran-2-yl | 0 | CH$_2$CO-1-piperazinyl-N-Boc |
| 87 | 8-Methoxy-dibenzofuran-2-yl | 1 | CH$_2$CO-1-piperazinyl |
|  | 8-Methoxy-dibenzofuran-2-yl | 0 | CH$_2$CO-1-(4-acetyl)-piperazinyl |
| 88 | 8-Methoxy-dibenzofuran-2-yl | 1 | CH$_2$CO-1-(4-acetyl)-piperazinyl |
| 26 | 8-Fluoro-dibenzofuran-2-yl | 0 | CH$_2$CO-1-piperazinyl-N-Boc |
| 45 | 8-Fluoro-dibenzofuran-2-yl | 1 | CH$_2$CO-1-piperazinyl |
|  | 8-Fluoro-dibenzofuran-2-yl | 0 | CH$_2$CO-1-(4-acetyl)-piperazinyl |
| 89 | 8-Fluoro-dibenzofuran-2-yl | 1 | CH$_2$CO-1-(4-acetyl)-piperazinyl |
| 19 | 8-Fluoro-dibenzofuran-2-yl | 0 | CH$_2$CONH$_2$ |
| 38 | 8-Fluoro-dibenzofuran-2-yl | 1 | CH$_2$CONH$_2$ |
|  | 4-Chloro-dibenzofuran-2-yl | 0 | CH$_2$CONH$_2$ |
| 90 | 4-Chloro-dibenzofuran-2-yl | 1 | CH$_2$CONH$_2$ |
|  | 4-Fluoro-dibenzofuran-2-yl | 0 | CH$_2$CONH$_2$ |
| 91 | 4-Fluoro-dibenzofuran-2-yl | 1 | CH$_2$CONH$_2$ |
|  | 4-Chloro-dibenzofuran-2-yl | 0 | CH$_2$CO-1-(4-acetyl)-piperazinyl |
| 92 | 4-Chloro-dibenzofuran-2-yl | 1 | CH$_2$CO-1-(4-acetyl)-piperazinyl |
|  | 4-Fluoro-dibenzofuran-2-yl | 0 | CH$_2$CO-1-(4-acetyl)-piperazinyl |
| 93 | 4-Fluoro-dibenzofuran-2-yl | 1 | CH$_2$CO-1-(4-acetyl)-piperazinyl |
|  | 4-Fluoro-8-chloro-dibenzofuran-2-yl | 0 | CH$_2$CONH$_2$ |
| 94 | 4-Fluoro-8-chloro-dibenzofuran-2-yl | 1 | CH$_2$CONH$_2$ |
|  | Dibenzofuran-4-yl | 0 | CH$_2$CONHCH$_2$CH$_2$OH |
| 95 | Dibenzofuran-4-yl | 1 | CH$_2$CONHCH$_2$CH$_2$OH |
|  | Dibenzofuran-4-yl | 0 | CH$_2$CONH$_2$ |
| 96 | Dibenzofuran-4-yl | 1 | CH$_2$CONH$_2$ |
|  | Dibenzofuran-4-yl | 0 | CH$_2$CO-1-(4-acetyl)-piperazinyl |
| 97 | Dibenzofuran-4-yl | 1 | CH$_2$CO-1-(4-acetyl)-piperazinyl |
|  | Dibenzofuran-4-yl | 0 | CH$_2$CO-1-(4-hydroxy)piperidinyl |
| 98 | Dibenzofuran-4-yl | 1 | CH$_2$CO-1-(4-hydroxy)piperidinyl |
|  | Dibenzofuran-4-yl | 0 | CH$_2$CO-1-piperazinyl-N-Boc |
| 99 | Dibenzofuran-4-yl | 1 | CH$_2$CO-1-piperazinyl |
|  | Dibenzofuran-4-yl | 0 | CH$_2$CON-(2-pyrrolidin-1-yl-ethyl) |
| 100 | Dibenzofuran-4-yl | 1 | CH$_2$CON-(2-pyrrolidin-1-yl-ethyl) |
|  | Dibenzofuran-4-yl | 0 | CH$_2$CON-[3-(2-oxo-pyrrolidin-1-yl)-propyl] |
| 101 | Dibenzofuran-4-yl | 1 | CH$_2$CON-[3-(2-oxo-pyrrolidin-1-yl)-propyl] |
|  | Dibenzofuran-4-yl | 0 | CH$_2$CON-(2-piperidin-1-yl-ethyl) |
| 102 | Dibenzofuran-4-yl | 1 | CH$_2$CON-(2-piperidin-1-yl-ethyl) |
|  | Dibenzofuran-4-yl | 0 | CH$_2$CON-(2-morpholin-4-yl-ethyl) |
| 103 | Dibenzofuran-4-yl | 1 | CH$_2$CON-(2-morpholin-4-yl-ethyl) |
|  | Dibenzofuran-4-yl | 0 | CH$_2$CO-1-(4-hydroxyethyl)-piperazinyl |
| 104 | Dibenzofuran-4-yl | 1 | CH$_2$CO-1-(4-hydroxyethyl)-piperazinyl |
|  | Dibenzofuran-3-yl | 0 | CH$_2$CO-1-piperazinyl-N-Boc |
| 105 | Dibenzofuran-3-yl | 1 | CH$_2$CO-1-piperazinyl |
|  | Dibenzofuran-1-yl | 0 | CH$_2$CO-1-piperazinyl-N-Boc |
| 106 | Dibenzofuran-1-yl | 1 | CH$_2$CO-1-piperazinyl |
|  | Dibenzofuran-3-yl | 0 | CH$_2$CO-1-(4-acetyl)-piperazinyl |
| 107 | Dibenzofuran-3-yl | 1 | CH$_2$CO-1-(4-acetyl)-piperazinyl |
| 25 | Dibenzothiophen-2-yl | 0 | CH$_2$CO-1-piperazinyl-N-Boc |
| 44 | Dibenzothiophen-2-yl | 1 | CH$_2$CO-1-piperazinyl |
|  | Dibenzothiophen-2-yl | 0 | CH$_2$CO-1-(4-acetyl)-piperazinyl |
| 108 | Dibenzothiophen-2-yl | 1 | CH$_2$CO-1-(4-acetyl)-piperazinyl |
|  | Dibenzothiophen-2-yl | 0 | CH$_2$CO-1-(4-ethoxycarbonyl)-piperazinyl |

-continued

| Ex. n° | Ring Ar | q | Y-R¹ |
|---|---|---|---|
| 109 | Dibenzothiophen-2-yl | 1 | CH$_2$CO-1-(4-ethoxycarbonyl)-piperazinyl |
| 18 | Dibenzothiophen-2-yl | 0 | CH$_2$CONH$_2$ |
| 39 | Dibenzothiophen-2-yl | 1 | CH$_2$CONH$_2$ |
|  | Dibenzothiophen-4-yl | 0 | CH$_2$CO-1-(4-acetyl)-piperazinyl |
| 110 | Dibenzothiophen-4-yl | 1 | CH$_2$CO-1-(4-acetyl)-piperazinyl |
|  | Fluoren-1-yl | 0 | CH$_2$CONHCH$_2$CH$_2$OH |
| 111 | Fluoren-1-yl | 1 | CH$_2$CONHCH$_2$CH$_2$OH |
|  | Fluoren-1-yl | 0 | CH$_2$CO-1-(4-acetyl)-piperazinyl |
| 112 | Fluoren-1-yl | 1 | CH$_2$CO-1-(4-acetyl)-piperazinyl |
|  | Fluoren-1-yl | 0 | CH$_2$CO-1-(4-hydroxy)piperidinyl |
| 113 | Fluoren-1-yl | 1 | CH$_2$CO-1-(4-hydroxy)piperidinyl |
|  | Fluoren-1-yl | 0 | CH$_2$CO-1-(4-hydroxyethyl)-piperazinyl |
| 115 | Fluoren-1-yl | 1 | CH$_2$CO-1-(4-hydroxyethyl)-piperazinyl |
|  | Fluoren-1-yl | 0 | CH$_2$CO-1-piperazinyl-N-Boc |
| 116 | Fluoren-1-yl | 1 | CH$_2$CO-1-piperazinyl |
|  | Fluoren-2-yl | 0 | CH$_2$CON(CH$_3$)$_2$ |
| 118 | Fluoren-2-yl | 1 | CH$_2$CON(CH$_3$)$_2$ |
|  | Fluoren-2-yl | 0 | CH$_2$CO-N-pyrrolidinyl |
| 119 | Fluoren-2-yl | 1 | CH$_2$CO-N-pyrrolidinyl |
|  | Fluoren-2-yl | 0 | CH$_2$CONHCH(CH$_3$)$_2$ |
| 120 | Fluoren-2-yl | 1 | CH$_2$CONHCH(CH$_3$)$_2$ |
|  | Fluoren-2-yl | 0 | CH$_2$CONHCH$_2$CH$_2$OH |
| 121 | Fluoren-2-yl | 1 | CH$_2$CONHCH$_2$CH$_2$OH |
|  | Fluoren-2-yl | 0 | CH$_2$CO-1-(4-hydroxy)piperidinyl |
| 122 | Fluoren-2-yl | 1 | CH$_2$CO-1-(4-hydroxy)piperidinyl |
|  | Fluoren-2-yl | 0 | CH$_2$CO-1-(4-acetyl)-piperazinyl |
| 123 | Fluoren-2-yl | 1 | CH$_2$CO-1-(4-acetyl)-piperazinyl |
|  | Fluoren-4-yl | 0 | CH$_2$CON(CH$_3$)$_2$ |
| 125 | Fluoren-4-yl | 1 | CH$_2$CON(CH$_3$)$_2$ |
|  | Fluoren-4-yl | 0 | CH$_2$CONHCH(CH$_3$)$_2$ |
| 126 | Fluoren-4-yl | 1 | CH$_2$CONHCH(CH$_3$)$_2$ |
|  | Fluoren-4-yl | 0 | CH$_2$CONHCH$_2$CH$_2$OH |
| 127 | Fluoren-4-yl | 1 | CH$_2$CONHCH$_2$CH$_2$OH |
|  | Fluoren-4-yl | 0 | CH$_2$CO-1-(4-hydroxy)piperidinyl |
| 128 | Fluoren-4-yl | 1 | CH$_2$CO-1-(4-hydroxy)piperidinyl |
|  | Fluoren-4-yl | 0 | CH$_2$CO-1-(4-acetyl)-piperazinyl |
| 129 | Fluoren-4-yl | 1 | CH$_2$CO-1-(4-acetyl)-piperazinyl |
|  | Fluoren-4-yl | 0 | CH$_2$CO-1-piperazinyl-N-Boc |
| 130 | Fluoren-4-yl | 1 | CH$_2$CO-1-piperazinyl |
| 24 | Fluoren-4-yl | 0 | CH$_2$CO-1-(4-hydroxyethyl)-piperazinyl |
| 43 | Fluoren-4-yl | 1 | CH$_2$CO-1-(4-hydroxyethyl)-piperazinyl |
|  | Fluoren-4-yl | 0 | CH$_2$CO-1-(4-formyl)-piperazinyl |
| 131 | Fluoren-4-yl | 1 | CH$_2$CO-1-(4-formyl)-piperazinyl |
|  | 2-Phenylbenzofuran-3-yl | 0 | CH$_2$CONH$_2$ |
| 132 | 2-Phenylbenzofuran-3-yl | 1 | CH$_2$CONH$_2$ |
|  | 2-Phenylbenzofuran-3-yl | 0 | CH$_2$CO-N-pyrrolidinyl |
| 133 | 2-Phenylbenzofuran-3-yl | 1 | CH$_2$CO-N-pyrrolidinyl |
|  | 2-Phenybenzofuran-3-yl | 0 | CH$_2$CH$_2$CONH$_2$ |
| 134 | 2-Phenylbenzofuran-3-yl | 1 | CH$_2$CH$_2$CONH$_2$ |
|  | 2-Phenylbenzofuran-3-yl | 0 | CH$_2$CH$_2$CO-N-pyrrolidinyl |
| 135 | 2-Phenylbenzofuran-3-yl | 1 | CH$_2$CH$_2$CO-N-pyrrolidinyl |
| 20 | 2-Phenylbenzofuran-3-yl | 0 | CH$_2$CON(CH$_3$)$_2$ |
| 46 | 2-Phenylbenzofuran-3-yl | 1 | CH$_2$CON(CH$_3$)$_2$ |
|  | 2-Phenylbenzofuran-3-yl | 0 | CH$_2$CH$_2$CON(CH$_3$)$_2$ |
| 136 | 2-Phenylbenzofuran-3-yl | 1 | CH$_2$CH$_2$CON(CH$_3$)$_2$ |
|  | 2-Phenylbenzofuran-3-yl | 0 | CH$_2$CONHCH(CH$_3$)$_2$ |
| 137 | 2-Phenylbenzofuran-3-yl | 1 | CH$_2$CONHCH(CH$_3$)$_2$ |
|  | 2-Phenylbenzofuran-3-yl | 0 | CH$_2$CH$_2$CONHCH(CH$_3$)$_2$ |
| 138 | 2-Phenylbenzofuran-3-yl | 1 | CH$_2$CH$_2$CONHCH(CH$_3$)$_2$ |
|  | 2-Phenylbenzofuran-3-yl | 0 | CH$_2$CO-1-(4-acetyl)-piperazinyl |
| 139 | 2-Phenylbenzofuran-3-yl | 1 | CH$_2$CO-1(4-acetyl)-piperazinyl |
|  | 2-Phenylbenzofuran-3-yl | 0 | CH$_2$CH$_2$CO-1-(4-acetyl)-piperazinyl |
| 140 | 2-Phenylbenzofuran-3-yl | 1 | CH$_2$CH$_2$CO-1-(4-acetyl)-piperazinyl |
|  | 3-Phenylbenzothiophen-2-yl | 0 | CH$_2$CONH$_2$ |
| 141 | 3-Phenylbenzothiophen-2-yl | 1 | CH$_2$CONH$_2$ |
| 27 | 3-phenylbenzothiophen-2-yl | 0 | CH2-CO-N-pyrrolidinyl |
| 28 | 3-phenylbenzothiophen-2-yl | 0 | CH2-CON(CH$_3$)$_2$ |
| 29 | 3-phenylbenzothiophen-2-yl | 0 | CH2-CONHCH(CH$_3$)$_2$ |
| 30 | 3-phenylbenzothiophen-2-yl | 0 | CH2-CO-1-(4-hydroxy)-piperidinyl |
| 31 | 3-phenylbenzothiophen-2-yl | 0 | CH2-CO-1-(4-acetyl)-piperazinyl |
| 32 | 3-phenylbenzothiophen-2-yl | 0 | CH2-CONH(CH$_2$)$_2$OH |
| 47 | 3-phenylbenzothiophen-2-yl | 1 | CH2-CO-N-pyrrolidinyl |
| 48 | 3-phenylbenzothiophen-2-yl | 1 | CH2-CON(CH$_3$)$_2$ |
| 49 | 3-phenylbenzothiophen-2-yl | 1 | CH2-CONHCH(CH$_3$)$_2$ |
| 50 | 3-phenylbenzothiophen-2-yl | 1 | CH2-CO-1-(4-hydroxy)-piperidinyl |
| 51 | 3-phenylbenzothiophen-2-yl | 1 | CH2-CO-1-(4-acetyl)-piperazinyl |
| 52 | 3-phenylbenzothiophen-2-yl | 1 | CH2-CONH(CH$_2$)$_2$OH |

-continued

| Ex. n° | Ring Ar | q | Y-R$^1$ |
|---|---|---|---|
| 33 | 3-phenyl-1,4-benzodioxin-2-yl | 0 | CH$_2$CO-1-(4-acetyl)-piperazinyl |
| 53 | 3-phenyl-1,4-benzodioxin-2-yl | 1 | CH$_2$CO-1-(4-acetyl)-piperazinyl |
|  | 3-phenyl-1,4-benzodioxin-2-yl | 0 | CH$_2$CONHCH(CH$_3$)$_2$ |
| 142 | 3-phenyl-1,4-benzodioxin-2-yl | 1 | CH$_2$CONHCH(CH$_3$)$_2$ |
|  | 3-phenyl-1,4-benzodioxin-2-yl | 0 | CH$_2$CONH$_2$ |
| 143 | 3-phenyl-1,4-benzodioxin-2-yl | 1 | CH$_2$CONH$_2$ |
|  | 6,7-dichloro-3-phenyl-1,4-benzodioxin-2-yl | 0 | CH$_2$CONH$_2$ |
| 144 | 6,7-dichloro-3-phenyl-1,4-benzodioxin-2-yl | 1 | CH$_2$CONH$_2$ |
|  | 6,7-dichloro-3-phenyl-1,4-benzodioxin-2-yl | 0 | CH$_2$CO-1-(4-acetyl)-piperazinyl |
| 145 | 6,7-dichloro-3-phenyl-1,4-benzodioxin-2-yl | 1 | CH$_2$CO-1-(4-acetyl)-piperazinyl |
| 148 | 3-phenyl-1H-indol-2-yl | 0 | CH$_2$CONH$_2$ |
| 149 | 3-phenyl-1H-indol-2-yl | 1 | CH$_2$CONH$_2$ |
| 150 | 7-chlorodibenzofuran-1-yl | 0 | CH$_2$CONH$_2$ |
| 151 | 7-chlorodibenzofuran-1-yl | 1 | CH2CONH2 |
|  | 8-chlorodibenzofuran-1-yl | 0 | CH2CONH2 |
| 152 | 8-chlorodibenzofuran-1-yl | 1 | CH2CONH2 |
|  | 7,8-dichlorodibenzofuran-1-yl | 0 | CH2CONH2 |
| 153 | 7,8-dichlorodibenzofuran-1-yl | 1 | CH2CONH2 |

48. A use of a compound of formula (A):

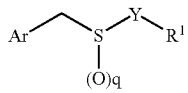

(A)

wherein:
Ar is

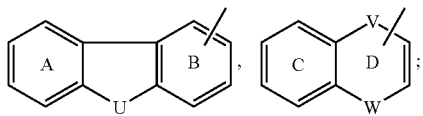

wherein
U is CH$_2$, CR$^{25}$R$^{26}$, O, S(O)$_y$, NR$^{10}$, C(=O), C(=S), CHOH, CHOR$^{14}$, C=NOR$^{14}$, or C=NNR$^{12}$R$^{13}$;

V and W are independently selected from a bond, CH$_2$, CR$^{25}$R$^{26}$, O, S(O)$_y$, NR$^{10}$, C(=O), C(=S), CHOH, CHOR$^{14}$, C=NOR$^{14}$, or C=NNR$^{12}$R$^{13}$;

rings A, B, and C are optionally substituted with one to three groups selected from F, Cl, Br, I, OR$^{22}$, OR$^{27}$, NR$^{23}$R$^{24}$, NHOH, NO$_2$, CN, CF$_3$, C$_1$–C$_6$ alkyl, C$_2$–C$_6$ alkenyl, C$_2$–C$_6$ alkynyl, C$_3$–C$_7$ cycloalkyl, 3–7 membered heterocycloalkyl, phenyl, 5 or 6 membered heteroaryl, arylalkyl, C(=O)R$^{22}$, CO$_2$R$^{22}$, OC(=O)R$^{22}$, C(=O)NR$^{23}$R$^{24}$, NR$^{21}$C(=O)R$^{22}$, NR$^{21}$CO$_2$R$^{22}$, OC(=O)NR$^{23}$R$^{24}$, NR$^{21}$C(=S)R$^{22}$, and S(O)$_y$R$^{22}$;

ring D is optionally substituted with one group selected from C$_1$–C$_6$ alkyl, phenyl, and 5–10 membered heteroaryl; provided that when V is a bond, and W is O, S(O)y or NR$^{10}$, ring D is substituted by a phenyl group;

Y is C$_1$–C$_6$ alkylene; or
(C$_1$–C$_4$ alkylene)$_m$-Z-(C$_1$–C$_4$ alkylene)$_n$;
wherein said alkylene groups are optionally substituted with one to three R$^{20}$ groups;

Z is O, NR$^{10A}$, S(O)$_y$, CR$^{21}$=CR$^{21}$, C≡C, C$_6$–C$_{10}$ arylene, 5–10 membered heteroarylene, C$_3$–C$_6$ cycloalkylene, or 3–6 membered heterocycloalkylene; wherein said arylene, heteroarylene, cycloalkylene, and heterocycloalkylene groups are optionally substituted with one to three R$^{20}$ groups;

R$^1$ is selected from H, NR$^{12}$R$^{13}$, NR$^{21}$C(=O)R$^{14}$, C(=O)R$^{14}$, CO$_2$R$^{11}$, OC(=O)R$^{11}$, C(=O)NR$^{12}$R$^{13}$, C(=NR$^{11}$)NR$^{12}$R$^{13}$, OC(=O)NR$^{12}$R$^{13}$, NR$^{21}$S(O)$_2$R$^{11}$, NR$^{21}$C(=O)NR$^{12}$R$^{13}$, NR$^{21}$(SO$_2$)NR$^{12}$R$^{13}$, and C(=O)NR$^{11}$OR$^{22}$;

R$^{10}$ and R$^{10A}$ are each independently selected from H, C$_1$–C$_6$ alkyl, C$_6$–C$_{10}$ aryl, C(=O)R$^{14}$, and S(O)$_y$R$^{14}$; wherein said alkyl and aryl groups are optionally substituted with one to three R$^{20}$ groups;

R$^{11}$ at each occurrence is independently selected from H, C$_1$–C$_6$ alkyl, and C$_6$–C$_{10}$ aryl; wherein said alkyl and aryl groups are optionally substituted with one to three R$^{20}$ groups;

R$^{12}$ and R$^{13}$ at each occurrence are each independently selected from H, C$_1$–C$_6$ alkyl, C$_6$–C$_{10}$ aryl, and NR$^{23}$R$^{24}$, or R$^{12}$ and R$^{13}$, together with the nitrogen to which they are attached, form a 3–7 membered heterocyclic ring; wherein said alkyl and aryl groups and heterocyclic ring are optionally substituted with one to three R$^{20}$ groups;

R$^{14}$ at each occurrence is independently selected from C$_1$–C$_6$ alkyl, C$_6$–C$_{10}$ aryl, and alkylaryl;
wherein said alkyl, aryl and alkylaryl groups are optionally substituted with one to three R$^{20}$ groups;

R$^{20}$ at each occurrence is independently selected from F, Cl, Br, I, OR$^{22}$, OR$^{27}$, NR$^{23}$R$^{24}$, NHOH, NO$_2$, CN, CF$_3$, C$_1$–C$_6$ alkyl optionally substituted with OH, C$_2$–C$_6$ alkenyl, C$_2$–C$_6$ alkynyl, C$_3$–C$_7$ cycloalkyl, 3–7 membered heterocycloalkyl, phenyl, 5 or 6 membered heteroaryl, arylalkyl, =O, C(=O)R$^{22}$, CO$_2$R$^{22}$, OC(=O)R$^{22}$, C(=O)NR$^{23}$R$^{24}$, NR$^{21}$C(=O)R$^{22}$, NR$^{21}$CO$_2$R$^{22}$, OC(=O)NR$^{23}$R$^{24}$, NR$^{21}$C(=S)R$^{22}$ and S(O)$_y$R$^{22}$;

R$^{21}$ at each occurrence is independently selected from H and C$_1$–C$_6$ alkyl;

R$^{22}$ at each occurrence is independently selected from H, C$_1$–C$_6$ alkyl optionally substituted with OH, arylalkyl and C$_6$–C$_{10}$ aryl;

$R^{23}$ and $R^{24}$ at each occurrence are each independently selected from H, $C_1$–$C_6$ alkyl, and $C_6$–$C_{10}$ aryl, or $R^{23}$ and $R^{24}$, together with the nitrogen to which they are attached, form a 3–7 membered heterocyclic ring optionally substituted with =O;

$R^{25}$ and $R^{26}$ at each occurrence are each independently selected from H, $C_1$–$C_6$ alkyl, and $C_6$–$C_{10}$aryl, or $R^{25}$ and $R^{26}$, together with the carbon to which they are attached, form a 3–7 membered heterocyclic ring;

$R^{27}$ at each occurrence is independently the residue of an amino acid after the hydroxyl group of the carboxyl group is removed;

m is 0 or 1;

n is 0 or 1;

q is 0, 1, or 2;

y is 0, 1, or 2;

and the stereoisomeric forms, mixtures of stereoisomeric forms or pharmaceutically acceptable salts forms thereof, for the manufacture of a medicament useful for the treatment of a disease or a disorder selected from the group consisting of sleepiness associated with narcolepsy, obstructive sleep apnea or shift work disorder; Parkinson's disease; Alzheimer's disease; attention deficit disorder; attention deficit hyperactivity disorder; depression; and fatigue.

49. The use of a compound of formula (A) according to claim 48 for the manufacture of a medicament useful for the treatment of sleepiness associated with narcolepsy.

50. A use of a compound of formula (A)

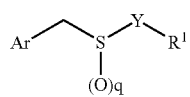

(A)

wherein:
Ar is:

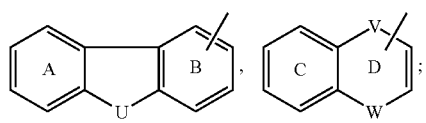

wherein:
U is $CH_2$, $CR^{25}R^{26}$, O, $S(O)_y$, $NR^{10}$, C(=O), C(=S), CHOH, $CHOR^{14}$, C=$NOR^{14}$, or C=$NNR^{12}R^{13}$;

V and W are independently selected from a bond, $CH_2$, $CR^{25}R^{26}$, O, $S(O)_y$, $NR^{10}$, C(=O), C(=S), CHOH, $CHOR^{14}$, C=$NOR^{14}$, or C=$NNR^{12}R^{13}$;

rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1$–$C_6$ alkyl, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, C(=O)$R^{22}$, $CO_2R^{22}$, OC(=O)$R^{22}$, C(=O)$NR^{23}R^{24}$, $NR^{21}$C(=O)$R^{22}$, $NR^{21}CO_2R^{22}$, OC(=O)$NR^{23}R^{24}$, $NR^{21}$C(=S)$R^{22}$, and $S(O)_yR^{22}$;

ring D is optionally substituted with one group selected from $C_1$–$C_6$ alkyl, phenyl, and 5–10 membered heteroaryl; provided that when V is a bond, and W is O, $S(O)y$ or $NR^{10}$, ring D is substituted by a phenyl group;

Y is $C_1$–$C_6$ alkylene; or
($C_1$–$C_4$ alkylene)$_m$-Z-($C_1$–$C_4$ alkylene)$_n$;
wherein said alkylene groups are optionally substituted with one to three $R^{20}$ groups;

Z is O, $NR^{10A}$, $S(O)_y$, $CR^{21}$=$CR^{21}$, C≡C, $C_6$–$C_{10}$ arylene, 5–10 membered heteroarylene, $C_3$–$C_6$ cycloalkylene, or 3–6 membered heterocycloalkylene; wherein said arylene, heteroarylene, cycloalkylene, and heterocycloalkylene groups are optionally substituted with one to three $R^{20}$ groups;

$R^1$ is selected from H, $NR^{12}R^{13}$, $NR^{21}$C(=O)$R^{14}$, C(=O)$R^{14}$, $CO_2R^{11}$, OC(=O)$R^{11}$, C(=O)$NR^{12}R^{13}$, C(=$NR^{11}$)$NR^{12}R^{13}$, OC(=O)$NR^{12}R^{13}$, $NR^{21}S(O)_2R^{11}$, $NR^{21}$C(=O)$NR^{12}R^{13}$, $NR^{21}(SO_2)NR^{12}R^{13}$, and C(=O)$NR^{11}OR^{22}$;

$R^{10}$ and $R^{10A}$ are each independently selected from H, $C_1$–$C_6$ alkyl, $C_6$–$C_{10}$ aryl, C(=O)$R^{14}$, and $S(O)_yR^{14}$; wherein said alkyl and aryl groups are optionally substituted with one to three $R^{20}$ groups;

$R^{11}$ at each occurrence is independently selected from H, $C_1$–$C_6$ alkyl, and $C_6$–$C_{10}$ aryl; wherein said alkyl and aryl groups are optionally substituted with one to three $R^{20}$ groups;

$R^{12}$ and $R^{13}$ at each occurrence are each independently selected from H, $C_1$–$C_6$ alkyl, $C_6$–$C_{10}$ aryl, and $NR^{23}R^{24}$, or $R^{12}$ and $R^{13}$, together with the nitrogen to which they are attached, form a 3–7 membered heterocyclic ring; wherein said alkyl and aryl groups and heterocyclic ring are optionally substituted with one to three $R^{20}$ groups;

$R^{14}$ at each occurrence is independently selected from $C_1$–$C_6$ alkyl, $C_6$–$C_{10}$ aryl, and alkylaryl; wherein said alkyl, aryl and alkylaryl groups are optionally substituted with one to three $R^{20}$ groups;

$R^{20}$ at each occurrence is independently selected from F, Cl, Br, I, $OR^{22}$, $OR^{27}$, $NR^{23}R^{24}$, NHOH, $NO_2$, CN, $CF_3$, $C_1$–$C_6$ alkyl optionally substituted with OH, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, =O, C(=O)$R^{22}$, $CO_2R^{22}$, OC(=O)$R^{22}$, C(=O)$NR^{23}R^{24}$, $NR^{21}$C(=O)$R^{22}$, $NR^{21}CO_2R^{22}$, OC(=O)$NR^{23}R^{24}$4, $NR^{21}$C(=S)$R^{22}$, and $S(O)_yR^{22}$;

$R^{21}$ at each occurrence is independently selected from H and $C_1$–$C_6$ alkyl $R^{22}$ at each occurrence is independently selected from H, $C_1$–$C_6$ alkyl optionally substituted with OH, arylalkyl and $C_6$–$C_{10}$ aryl;

$R^{23}$ and $R^{24}$ at each occurrence are each independently selected from H, $C_1$–$C_6$ alkyl, and $C_6$–$C_{10}$ aryl, or $R^{23}$ and $R^{24}$, together with the nitrogen to which they are attached, form a 3–7 membered heterocyclic ring optionally substituted with =O;

$R^{25}$ and $R^{26}$ at each occurrence are each independently selected from H, $C_1$–$C_6$ alkyl and $C_6$–$C_{10}$ aryl, or $R^{25}$ and $R^{26}$, together with the carbon to which they are attached, form a 3–7 membered heterocyclic ring;

$R^{27}$ at each occurrence is independently the residue of an amino acid after the hydroxyl group of the carboxyl group is removed;

m is 0 or 1;

n is 0 or 1;

q is 0, 1, or 2;

y is 0, 1, or 2;

and the stereoisomeric forms, mixtures of stereoisomeric forms or pharmaceutically acceptable salts forms thereof, for the manufacture of a medicament useful for the treatment of a sleep-affecting disease or disorder in order to promote wakefulness.

51. A use of a compound of formula (A)

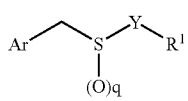

wherein:
Ar is:

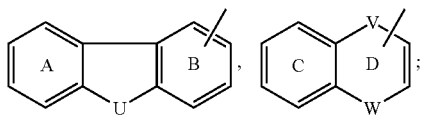

wherein:
U is $CH_2$, $CR^{25}R^{26}$, O, $S(O)_y$, $NR^{10}$, $C(=O)$, $C(=S)$, CHOH, $CHOR^{14}$, $C=NOR^{14}$, or $C=NNR^{12}R^{13}$;
V and W are independently selected from a bond, $CH_2$, $CR^{25}R^{26}$, O, $S(O)_y$, $NR^{10}$, $C(=O)$, $C(=S)$, CHOH, $CHOR^{14}$, $C=NOR^{14}$, or $C=NNR^{12}R^{13}$;
rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1$–$C_6$ alkyl, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
ring D is optionally substituted with one group selected from $C_1$–$C_6$ alkyl, phenyl, and 5–10 membered heteroaryl; provided that when V is a bond, and W is O, $S(O)_y$, or $NR^{10}$, ring D is substituted by a phenyl group;
Y is $C_1$–$C_6$ alkylene; or
($C_1$–$C_4$ alkylene)$_m$-Z-($C_1$–$C_4$ alkylene)$_n$;
wherein said alkylene groups are optionally substituted with one to three $R^{20}$ groups;
Z is O, $NR^{10A}$, $S(O)_y$, $CR^{21}=CR^{21}$, C≡C, $C_6$–$C_{10}$ arylene, 5–10 membered heteroarylene, $C_3$–$C_6$ cycloalkylene, or 3–6 membered heterocycloalkylene; wherein said arylene, heteroarylene, cycloalkylene, and heterocycloalkylene groups are optionally substituted with one to three $R^{20}$ groups;
$R^1$ is selected from H, $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, $NR^{21}(SO_2)NR^{12}R^{13}$, and $C(=O)NR^{11}OR^{22}$;
$R^{10}$ and $R^{10A}$ are each independently selected from H, $C_1$–$C_6$ alkyl, $C_6$–$C_{10}$ aryl, $C(=O)R^{14}$, and $S(O)_yR^{14}$; wherein said alkyl and aryl groups are optionally substituted with one to three $R^{20}$ groups;
$R^{11}$ at each occurrence is independently selected from H, $C_1$–$C_6$ alkyl, and $C_6$–$C_{10}$ aryl; wherein said alkyl and aryl groups are optionally substituted with one to three $R^{20}$ groups;
$R^{12}$ and $R^{13}$ at each occurrence are each independently selected from H, $C_1$–$C_6$ alkyl, $C_6$–$C_{10}$ aryl, and $NR^{23}R^{24}$, or $R^{12}$ and $R^{13}$, together with the nitrogen to which they are attached, form a 3–7 membered heterocyclic ring; wherein said alkyl and aryl groups and heterocyclic ring are optionally substituted with one to three $R^{20}$ groups;

$R^{14}$ at each occurrence is independently selected from $C_1$–$C_6$ alkyl, $C_6$–$C_{10}$ aryl, and alkylaryl;
wherein said alkyl, aryl and alkylaryl groups are optionally substituted with one to three $R^{20}$ groups;
$R^{20}$ at each occurrence is independently selected from F, Cl, Br, I, $OR^{22}$, $OR^{27}$, $NR^{23}R^{24}$, NHOH, $NO_2$, CN, $CF_3$, $C_1$–$C_6$ alkyl optionally substituted with OH, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
$R^{21}$ at each occurrence is independently selected from H and $C_1$–$C_6$ alkyl;
$R^{22}$ at each occurrence is independently selected from H, $C_1$–$C_6$ alkyl optionally substituted with OH, arylalkyl and $C_6$–$C_{10}$ aryl;
$R^{23}$ and $R^{24}$ at each occurrence are each independently selected from H, $C_1$–$C_6$ alkyl, and $C_6$–$C_{10}$ aryl, or $R^{23}$ and $R^{24}$, together with the nitrogen to which they are attached, form a 3–7 membered heterocyclic ring optionally substituted with =O;
$R^{25}$ and $R^{26}$ at each occurrence are each independently selected from H, $C_1$–$C_6$ alkyl, and $C_6$–$C_{10}$ aryl, or $R^{25}$ and $R^{26}$, together with the carbon to which they are attached, form a 3–7 membered heterocyclic ring;
$R^{27}$ at each occurrence is independently the residue of an amino acid after the hydroxyl group of the carboxyl group is removed;
m is 0 or 1;
n is 0 or 1;
q is 0, 1, or 2;
y is 0, 1, or 2;

and the stereoisomeric forms, mixtures of stereoisomeric forms or pharmaceutically acceptable salts forms thereof, for the manufacture of a medicament useful for the treatment of a neurological disease or disorder selected from Parkinson's disease; Alzheimer's disease; attention deficit disorder; attention deficit hyperactivity disorder; depression; and fatigue associated with a neurological disease or disorder.

52. A pharmaceutical composition comprising a compound of formula (A):

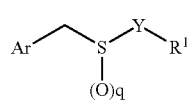

wherein
Ar is:

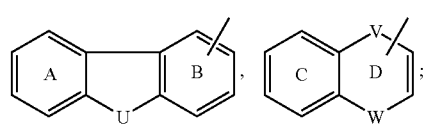

wherein:
U is $CH_2$, $CR^{25}R^{26}$, O, $S(O)_y$, $NR^{10}$, $C(=O)$, $C(=S)$, CHOH, $CHOR^{14}$, $C=NOR^{14}$, or $C=NNR^{12}R^{13}$;

V and W are independently selected from a bond, $CH_2$, $CR^{25}R^{26}$, O, $S(O)_y$, $NR^{10}$, $C(=O)$, $C(=S)$, CHOH, $CHOR^{14}$, $C=NOR^{14}$, or $C=NNR^{12}R^{13}$;

rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1$–$C_6$ alkyl, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

ring D is optionally substituted with one group selected from $C_1$–$C_6$ alkyl, phenyl, and 5–10 membered heteroaryl; provided that when V is a bond, and W is O, S(O)y or $NR^{10}$, ring D is substituted by a phenyl group;

Y is $C_1$–$C_6$ alkylene; or ($C_1$–$C_4$ alkylene)$_m$-Z-($C_1$–$C_4$ alkylene)$_n$;

wherein said alkylene groups are optionally substituted with one to three $R^{20}$ groups;

Z is O, $NR^{10A}$, $S(O)_y$, $CR^{21}=CR^{21}$, C≡C, $C_6$–$C_{10}$ arylene, 5–10 membered heteroarylene, $C_3$–$C_6$ cycloalkylene, or 3–6 membered heterocycloalkylene; wherein said arylene, heteroarylene, cycloalkylene, and heterocycloalkylene groups are optionally substituted with one to three $R^{20}$ groups;

$R^1$ is selected from H, $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, $NR^{21}(SO_2)NR^{12}R^{13}$, and $C(=O)NR^{11}OR^{22}$;

$R^{10}$ and $R^{10A}$ are each independently selected from H, $C_1$–$C_6$ alkyl, $C_6$–$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_1$–$C_6$ alkyl, and $C_6$–$C_{10}$ aryl; wherein said alkyl and aryl groups are optionally substituted with one to three $R^{20}$ groups;

$R^{12}$ and $R^{13}$ at each occurrence are each independently selected from H, $C_1$–$C_6$ alkyl, $C_6$–$C_{10}$ aryl, and $NR^{23}R^{24}$, or $R^{12}$ and $R^{13}$, together with the nitrogen to which they are attached, form a 3–7 membered heterocyclic ring; wherein said alkyl and aryl groups and heterocyclic ring are optionally substituted with one to three $R^{20}$ groups;

$R^{14}$ at each occurrence is independently selected from $C_1$–$C_6$ alkyl, $C_6$–$C_{10}$ aryl, and alkylaryl;

wherein said alkyl, aryl and alkylaryl groups are optionally substituted with one to three $R^{20}$ groups;

$R^{20}$ at each occurrence is independently selected from F, Cl, Br, I, $OR^{22}$, $OR^{27}$, $NR^{23}R^{24}$, NHOH, $NO_2$, CN, $CF_3$, $C_1$–$C_6$ alkyl optionally substituted with OH, $C_2$–$C_6$ alkenyl, $C_2$–$C_6$ alkynyl, $C_3$–$C_7$ cycloalkyl, 3–7 membered heterocycloalkyl, phenyl, 5 or 6 membered heteroaryl, arylalkyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

$R^{21}$ at each occurrence is independently selected from H and $C_1$–$C_6$ alkyl;

$R^{22}$ at each occurrence is independently selected from H, $C_1$–$C_6$ alkyl optionally substituted with OH, arylalkyl and $C_6$–$C_{10}$ aryl;

$R^{23}$ and $R^{24}$ at each occurrence are each independently selected from H, $C_1$–$C_6$ alkyl, and $C_6$–$C_{10}$aryl, or $R^{23}$ and $R^{24}$, together with the nitrogen to which they are attached, form a 3–7 membered heterocyclic ring optionally substituted with =O;

$R^{25}$ and $R^{26}$ at each occurrence are each independently selected from H, $C_1$–$C_6$ alkyl, and $C_6$–$C_{10}$aryl, or $R^{25}$ and $R^{26}$, together with the carbon to which they are attached, form a 3–7 membered heterocyclic ring;

$R^{27}$ at each occurrence is independently the residue of an amino acid after the hydroxyl group of the carboxyl group is removed;

m is 0 or 1;

n is 0 or 1;

q is 0, 1, or 2;

y is 0, 1, or 2;

and with the exclusion of the compounds wherein:

U is $CH_2$; and

Y is $C_1$–$C_6$ alkylene optionally substituted with $C_1$–$C_6$ alkylene; and $R^1$ is $CONH_2$, or $CO_2R^{11}$ with $R^{11}$=H or $C_1$–$C_6$ alkyl;

and the stereoisomeric forms, mixtures of stereoisomeric forms or pharmaceutically acceptable salts forms thereof, in admixture with one or more pharmaceutically acceptable excipients.

53. A method for preparing a compound of claims 1 to 47, comprising the steps of:

a1) reacting a compound F with a compound G to form a compound of formula (Ia):

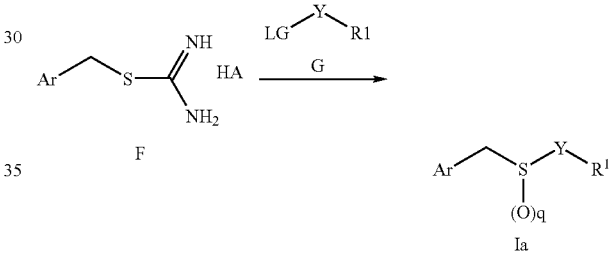

wherein Ar, Y, $R^1$ are as defined in claim 1, q=0 and LG is a leaving group; and optionally b1) isolating the formed compound (Ia).

54. The method according to claim 53, wherein the compound F is formed by reacting a compound C with thiourea and a suitable acid HA:

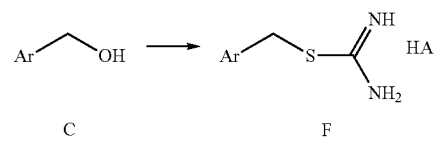

55. A method for preparing a compound of claims 1 to 47, comprising the steps of:

a2) reacting a compound E with a compound G to form a compound of formula (Ia):

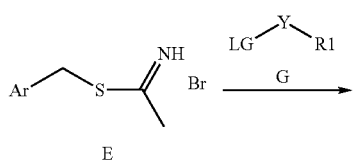

-continued wherein Ar, Y, R$^1$ are as defined in claim 1, q=0 and LG is a leaving group; and optionally b2) isolating the formed compound (Ia).

56. The method according to claim 55, wherein the compound E is formed by reacting a compound B with the thioacetamide:

57. A method for preparing a compound of claims 1 to 47, comprising the steps of:

a3) reacting a compound A with a compound D to form a compound of formula (Ia):

wherein Ar, Y, R$^1$ are as defined in claim 1 and q=0; and optionally b3) isolating the formed compound of formula (Ia).

58. A method for preparing a compound of claims 1 to 47 comprising the steps of:

a4) reacting a compound C with a compound H to form a compound (Ia):

wherein Ar, Y, R$^1$ are as defined in claim 1 and q=0; and optionally b4) isolating the formed compound (Ia).

59. A method for preparing a compound of claims 1 to 47 comprising the steps of:

a4) reacting a compound B with a compound H to form a compound (Ia):

wherein Ar, Y, R$^1$ are as defined in claim 1 and q=0; and optionally b4) isolating the formed compound (Ia).

60. The method according to any of claims 53 to 59, further comprising the steps of:

a5) reacting the compound (Ia) with an appropriate oxidizing agent fo form a compound (Ib):

wherein Ar, Y, R$^1$ are as defined in claim 1 and q is 1 or 2; and optionally b5) isolating the formed compound (Ib).

Although the present invention has been described in considerable detail, those skilled in the art will appreciate that numerous changes and modifications may be made to the embodiments and preferred embodiments of the invention and that such changes and modifications may be made without departing from the spirit of the invention. It is therefore intended that the appended claims cover all equivalent variations as fall within the scope of the invention.

What is claimed is:

1. A compound of formula (A):

(A)

wherein:

Ar is:

wherein:

U is O or S;

rings A and B are optionally substituted with one to three groups selected from F, cl, Br, I, OR$^{22}$, OR$^{27}$, NR$^{23}$R$^{24}$, NHOH, NO$_2$, CN, CF$_3$, C$_1$–C$_6$ alkyl, C$_2$–C$_6$ alkenyl, C$_2$–C$_6$ alkynyl, C$_3$–C$_7$ cycloalkyl, 3–7 membered heterocycloalkyl, phenyl, 5 or 6 membered heteroaryl, arylalkyl, C(=O)R$^{22}$, CO$_2$R$^{22}$, OC(=O)R$^{22}$, C(=O)NR$^{23}$R$^{24}$, NR$^{21}$C(=O)R$^{22}$, NR$^{21}$CO$_2$R$^{22}$, OC(=O)NR$^{23}$R$^{24}$, NR$^{21}$C(=S)R$^{22}$, and S(O)$_y$R$^{22}$;

Y is C$_1$–C$_6$ alkylene;

wherein said alkylene groups are optionally substituted with one to three R$^{20}$ groups;

R$_1$ is C(=O)NR$^{12}$R$^{13}$,

R$^{12}$ and R$^{13}$ at each occurrence are each independently selected from H, C$_1$–C$_6$ alkyl, or R$^{12}$ and R$^{13}$, together with the nitrogen to which they are attached, form a 3–7 membered heterocyclic ring;

wherein said alkyl groups and heterocyclic ring are optionally substituted with one to three R$^{20}$ groups;

R$^{20}$ at each occurrence is independently selected from F, Cl, Br, I, OR$^{22}$, OR$^{27}$, NR$^{23}$R$^{24}$, NHOH, NO$_2$, CN, CF$_3$, C$_1$–C$_6$ alkyl optionally substituted with OH, C$_2$–C$_6$ alkenyl, C$_2$–C$_6$ alkynyl, C$_3$–C$_7$ cycloalkyl, 3–7 membered heterocycloalkyl, phenyl, 5 or 6 membered heteroaryl, arylalkyl, =O, C(=O)$R^{22}$, $CO_2R^{22}$, OC(=O)$R^{22}$, C(=O)$NR^{23}R^{24}$, $NR^{21}$C(=O)$R^{22}$, $NR^{21}$C(=O)$OR^{22}$, OC(=O)$NR^{23}R^{24}$, $NR^{21}$C(=S)$R^{22}$, and S(O)$_y R^{22}$;

$R^{21}$ at each occurrence is independently selected from H and $C_1$–$C_6$ alkyl;

$R^{22}$ at each occurrence is independently selected from H, $C_1$–$C_6$ alkyl optionally substituted with OH, arylalkyl and $C_6$–$C_{10}$ aryl;

$R^{23}$ and $R^{24}$ at each occurrence are each independently selected from H, $C_1$–$C_6$ alkyl, and $C_6$–$C_{10}$ aryl, or $R^{23}$ and $R^{24}$, together with the nitrogen to which they are attached, form a 3–7 membered heterocyclic ring optionally substituted with =O;

$R^{27}$ at each occurrence is independently the residue of an naturally occurred amino acid after the hydroxyl group of the carboxyl group is removed;

q is 1, or 2;

y is 0, 1, or 2;

and the stereoisomeric forms, mixtures of stereoisomeric forms or pharmaceutically acceptable salts forms thereof.

2. The compound according to claims 1, wherein q is 1.

3. The compound according to claim 1, wherein $R^{12}$ and $R^{13}$ are each independently selected from H and $C_1$–$C_6$ alkyl.

4. The compound according to claim 1, wherein $R^{12}$ and $R^{13}$ together with the nitrogen to which they are attached, form a 3–7 membered heterocyclic ring, wherein said heterocyclic ring is optionally substituted with one $R^{20}$ group.

5. The compound according to claim 4, wherein said heterocyclic ring is unsubstituted.

6. The compound according to claim 1, wherein Y is $C_1$ to $C_6$ alkylene.

7. The compound according to claim 1, wherein Y is $CH_2$.

8. The compound according to claim 1, wherein rings A, B, and C are optionally substituted with one to three groups selected from F, Cl, Br, I, $OR^{22}$, $OR^{27}$, $NR^{23}R^{24}$, NHOH, $NO_2$, CN, $CF_3$, $C_1$–$C_6$ alkyl, phenyl, arylalkyl, and C(=O)$R^{22}$;

$R^{20}$ at each occurrence is independently selected from F, Cl, Br, I, $OR^{22}$, $OR^{27}$, $NR^{23}R^{24}$, NHOH, $NO_2$, CN, $CF_3$, $C_1$–$C_6$ alkyl optionally substituted with OH, phenyl, =O, C(=O)$R^{22}$, $CO_2R^{22}$, OC(=O)$R^{22}$, C(=O)$NR^{23}R^{24}$, $NR^{21}$C(=O)$R^{22}$, $NR^{21}CO_2R^{22}$, OC(=O)$NR^{23}R^{24}$, $NR^{21}$C(=S)$R^{22}$, and S(O)$_y R^{22}$;

and the stereoisomeric forms, mixtures of stereoisomeric forms or pharmaceutically acceptable salts forms thereof.

9. The compound according to claim 8, wherein Y is $CH_2$, or $CH_2$—$CH_2$.

10. The compound according to claim 1, selected in accordance with the following table:

(I)

wherein Ar, q, Y—$R^1$ are defined in the table below;

| Ex. No. | Ring Ar | q | Y-$R^1$ |
|---|---|---|---|
| 36 | Dibenzofuran-2-yl | 1 | $CH_2CONH_2$ |
| 54 | Dibenzofuran-2-yl | 1 | $CH_2CON(CH_3)_2$ |
| 55 | Dibenzofuran-2-yl | 1 | $CH_2$CO-N-pyrrolidinyl |
| 56 | Dibenzofuran-2-yl | 1 | $CH_2$CONHCH$(CH_3)_2$ |
| 57 | Dibenzofuran-2-yl | 1 | $CH_2$CO-1-piperazinyl |
| 58 | Dibenzofuran-2-yl | 1 | $CH_2$CO-1-(4-acetyl)-piperazinyl |
| 59 | Dibenzofuran-2-yl | 1 | $CH_2$CONHCH$_2$CH$_2$OH |
| 60 | Dibenzofuran-2-yl | 1 | $CH_2$CO-1-(4-hydroxy)piperidinyl |
| 61 | Dibenzofuran-2-yl | 1 | $CH_2$CONHCH$_2$CH$_2$OCH$_2$CH$_2$OH |
| 34 | Dibenzofuran-2-yl | 1 | $CH_2$CO-1-[4-(2-hydroxyethyl)-piperazinyl] |
| 62 | Dibenzofuran-2-yl | 1 | $CH_2$CO-1-(4-formyl)-piperazinyl |
| 63 | Dibenzofuran-2-yl | 1 | $CH_2$CO-1-(4-tert-butoxycarbonyl)-piperazinyl |
| 35 | Dibenzofuran-2-yl | 1 | $CH_2$CO-1-(4-ethoxycarbonyl)-piperazinyl |
| 64 | Dibenzofuran-2-yl | 1 | $CH_2$CO-1-(4-methyl)-piperazinyl |
| 65 | Dibenzofuran-2-yl | 1 | $CH_2$CO-1-(4-ethyl)-piperazinyl |
| 66 | Dibenzofuran-2-yl | 1 | $CH_2$CO-1-(4-propyl)-piperazinyl |
| 67 | Dibenzofuran-2-yl | 1 | $CH_2$CON-morpholinyl |
| 69 | Dibenzofuran-2-yl | 1 | $CH_2$CONHN-morpholinyl |
| 70 | Dibenzofuran-2-yl | 1 | $CH_2$CO-4-(2-oxo-piperazinyl) |
| 71 | Dibenzofuran-2-yl | 1 | $CH_2$CO-1-(4-isopropylaminocarbonyl)-piperazinyl |
| 72 | Dibenzofuran-2-yl | 1 | $CH_2$CO-1-(4-aminocarbonyl)-piperazinyl |
| 73 | Dibenzofuran-2-yl | 1 | $CH_2$CO-1-(4-pyrrolidinylcarbonyl)-piperazinyl |
| 74 | Dibenzofuran-2-yl | 1 | $CH_2$CO-1-(4-dimethylaminocarbonyl)-piperazinyl |
| 75 | Dibenzofuran-2-yl | 1 | $CH_2$CO-1-(4-benzyloxycarbonyl)-piperazinyl |
| 76 | Dibenzofuran-2-yl | 1 | $CH_2CH_2CONH_2$ |
| 77 | Dibenzofuran-2-yl | 1 | $CH_2CH_2$CO-1-piperazinyl |
| 78 | Dibenzofuran-2-yl | 1 | $CH_2CH_2$CO-1-(4-acetyl)-piperazinyl |
| 79 | Dibenzofuran-2-yl | 1 | $CH_2$CON-[3-(2-oxo-pyrrolidin-1-yl)-propyl] |
| 80 | Dibenzofuran-2-yl | 1 | $CH_2$CON-(2-pyrrolidin-1-yl-ethyl) |
| 81 | Dibenzofuran-2-yl | 1 | $CH_2$CON-(2-piperidin-1-yl-ethyl) |
| 82 | Dibenzofuran-2-yl | 1 | $CH_2$CON-(2-morpholin-4-yl-ethyl |
| 84 | 6-Chloro-dibenzofuran-2-yl | 1 | $CH_2$CO-1-piperazinyl |
| 85 | 6-Chloro-dibenzofuran-2-yl | 1 | $CH_2$CO-1-(4-acetyl)-piperazinyl |
| 41 | 8-Chloro-dibenzofuran-2-yl | 1 | $CH_2$CO-1-piperazinyl |

-continued

| Ex. No. | Ring Ar | q | Y-R$^1$ |
|---|---|---|---|
| 86 | 8-Chloro-dibenzofuran-2-yl | 1 | CH$_2$CONH$_2$ |
| 42 | 8-Chloro-dibenzofuran-2-yl | 1 | CH$_2$CO-1-(4-acetyl)-piperazinyl |
| 146 | 8-Chloro-dibenzofuran-2-yl | 2 | CH$_2$CO-1-(4-acetyl)-piperazinyl |
| 40 | 8-Chloro-dibenzofuran-2-yl | 1 | CH$_2$CO-1-(4-hydroxyethyl)-piperazinyl |
| 37 | 8-Methoxy-dibenzofuran-2-yl | 1 | CH$_2$CONH$_2$ |
| 87 | 8-Methoxy-dibenzofuran-2-yl | 1 | CH$_2$CO-1-piperazinyl |
| 88 | 8-Methoxy-dibenzofuran-2-yl | 1 | CH$_2$CO-1-(4-acetyl)-piperazinyl |
| 45 | 8-Fluoro-dibenzofuran-2-yl | 1 | CH$_2$CO-1-piperazinyl |
| 89 | 8-Fluoro-dibenzofuran-2-yl | 1 | CH$_2$CO-1-(4-acetyl)-piperazinyl |
| 38 | 8-Fluoro-dibenzofuran-2-yl | 1 | CH$_2$CONH$_2$ |
| 90 | 4-Chloro-dibenzofuran-2-yl | 1 | CH$_2$CONH$_2$ |
| 91 | 4-Fluoro-dibenzofuran-2-yl | 1 | CH$_2$CONH$_2$ |
| 92 | 4-Chloro-dibenzofuran-2-yl | 1 | CH$_2$CO-1-(4-acetyl)-piperazinyl |
| 93 | 4-Fluoro-dibenzofuran-2-yl | 1 | CH$_2$CO-1-(4-acetyl)-piperazinyl |
| 94 | 4-Fluoro-8-chloro-dibenzofuran-2-yl | 1 | CH$_2$CONH$_2$ |
| 95 | Dibenzofuran-4-yl | 1 | CH$_2$CONHCH$_2$CH$_2$OH |
| 96 | Dibenzofuran-4-yl | 1 | CH$_2$CONH$_2$ |
| 97 | Dibenzofuran-4-yl | 1 | CH$_2$CO-1-(4-acetyl)-piperazinyl |
| 98 | Dibenzofuran-4-yl | 1 | CH$_2$CO-1-(4-hydroxy)piperidinyl |
| 99 | Dibenzofuran-4-yl | 1 | CH$_2$CO-1-piperazinyl |
| 100 | Dibenzofuran-4-yl | 1 | CH$_2$CON-(2-pyrrolidin-1-yl-ethyl) |
| 101 | Dibenzofuran-4-yl | 1 | CH$_2$CON-[3-(2-oxo-pyrrolidin-1-yl)-propyl] |
| 102 | Dibenzofuran-4-yl | 1 | CH$_2$CON-(2-piperidin-1-yl-ethyl) |
| 103 | Dibenzofuran-4-yl | 1 | CH$_2$CON-(2-morpholin-4-yl-ethyl) |
| 104 | Dibenzofuran-4-yl | 1 | CH$_2$CO-1-(4-hydroxyethyl)-piperazinyl |
| 105 | Dibenzofuran-3-yl | 1 | CH$_2$CO-1-piperazinyl |
| 106 | Dibenzofuran-1-yl | 1 | CH$_2$CO-1-piperazinyl |
| 107 | Dibenzofuran-3-yl | 1 | CH$_2$CO-1-(4-acetyl)-piperazinyl |
| 44 | Dibenzothiophen-2-yl | 1 | CH$_2$CO-1-piperazinyl |
| 108 | Dibenzothiophen-2-yl | 1 | CH$_2$CO-1-(4-acetyl)-piperazinyl |
| 109 | Dibenzothiophen-2-yl | 1 | CH$_2$CO-1-(4-ethoxycarbonyl)-piperazinyl |
| 39 | Dibenzothiophen-2-yl | 1 | CH$_2$CONH$_2$ |
| 110 | Dibenzothiophen-4-yl | 1 | CH$_2$CO-1-(4-acetyl)-piperazinyl |
| 111 | Fluoren-1-yl | 1 | CH$_2$CONHCH$_2$CH$_2$OH |
| 112 | Fluoren-1-yl | 1 | CH$_2$CO-1-(4-acetyl)-piperazinyl |
| 113 | Fluoren-1-yl | 1 | CH$_2$CO-1-(4-hydroxy)piperidinyl |
| 115 | Fluoren-1-yl | 1 | CH$_2$CO-1-(4-hydroxyethyl)-piperazinyl |
| 116 | Fluoren-1-yl | 1 | CH$_2$CO-1-piperazinyl |
| 118 | Fluoren-2-yl | 1 | CH$_2$CON(CH$_3$)$_2$ |
| 119 | Fluoren-2-yl | 1 | CH$_2$CO-N-pyrrolidinyl |
| 120 | Fluoren-2-yl | 1 | CH$_2$CONHCH(CH$_3$)$_2$ |
| 121 | Fluoren-2-yl | 1 | CH$_2$CONHCH$_2$CH$_2$OH |
| 122 | Fluoren-2-yl | 1 | CH$_2$CO-1-(4-hydroxy)piperidinyl |
| 123 | Fluoren-2-yl | 1 | CH$_2$CO-1-(4-acetyl)-piperazinyl |
| 125 | Fluoren-4-yl | 1 | CH$_2$CON(CH$_3$)$_2$ |
| 126 | Fluoren-4-yl | 1 | CH$_2$CONHCH(CH$_3$)$_2$ |
| 127 | Fluoren-4-yl | 1 | CH$_2$CONHCH$_2$CH$_2$OH |
| 128 | Fluoren-4-yl | 1 | CH$_2$CO-1-(4-hydroxy)piperidinyl |
| 129 | Fluoren-4-yl | 1 | CH$_2$CO-1-(4-acetyl)-piperazinyl |
| 130 | Fluoren-4-yl | 1 | CH$_2$CO-1-piperazinyl |
| 43 | Fluoren-4-yl | 1 | CH$_2$CO-1-(4-hydroxyethyl)-piperazinyl |
| 131 | Fluoren-4-yl | 1 | CH$_2$CO-1-(4-formyl)-piperazinyl |
| 151 | 7-chlorodibenzofuran-1-yl | 1 | CH2CONH2 |
| 152 | 8-chlorodibenzofuran-1-yl | 1 | CH2CONH2 |
| 153 | 7,8-dichlorodibenzofuran-1-yl | 1 | CH2CONH2. |

11. A method of treating sleepiness associated with narcolepsy comprising administering to a patient in need thereof a compound of claim 1, or a stereoisomeric form, mixture of stereoisomeric forms or a pharmaceutically acceptable salt form thereof.

12. A pharmaceutical composition comprising a compound of claim 1, or the stereoisomeric forms, mixtures of stereoisomeric forms or pharmaceutically acceptable salts forms thereof, in admixture with one or more pharmaceutically acceptable excipients.

13. A method for preparing a compound of claim 1, comprising the steps of:

a1) reacting a compound F with a compound G to form a compound of formula (Ia):

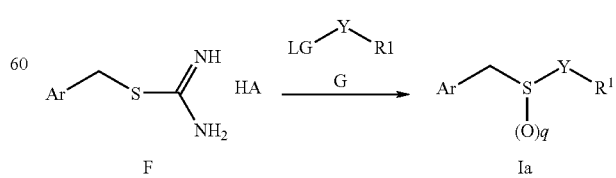

wherein Ar, Y, R$^1$ are as defined in claim 1, q=0 and LG is a leaving group; and optionally b1) isolating the formed compound (Ia); and reacting the compound (Ia) with an appropriate oxidizing agent to form a compound (Ib):

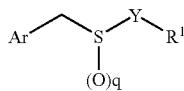

wherein Ar, Y, $R^1$ are as defined in claim 1 and q is 1 or 2; and optionally isolating the formed compound (Ib).

14. The method according to claim 13, wherein the compound F is formed by reacting a compound C with thiourea and a suitable acid HA:

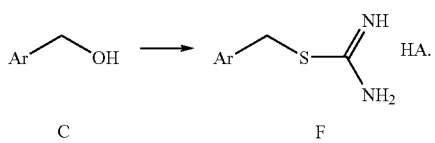

15. A method for preparing a compound of claim 1, comprising the steps of:

a2) reacting a compound E with a compound G to form a compound of formula (Ia):

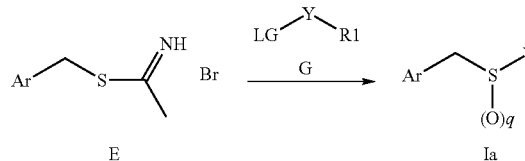

wherein Ar, Y, $R^1$ are as defined in claim 1, q=0 and LG is a leaving group; and optionally b2) isolating the formed compound (Ia); and reacting the compound (Ia) with an appropriate oxidizing agent to form a compound (Ib):

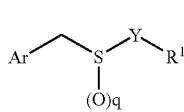

wherein Ar, Y, $R^1$ are as defined in claim 1 and q is 1 or 2; and optionally isolating the formed compound (Ib).

16. The method according to claim 15, wherein the compound E is formed by reacting a compound B with the thioacetamide:

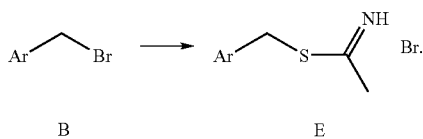

17. A method for preparing a compound of claim 1, comprising the steps of:

a3) reacting a compound A with a compound D to form a compound of formula (Ia):

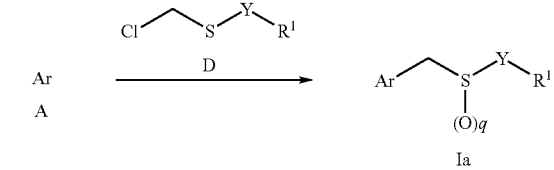

wherein Ar, Y, $R^1$ are as defined in claim 1 and q=0; and optionally b3) isolating the formed compound of formula (Ia); and reacting the compound (Ia) with an appropriate oxidizing agent to form a compound (Ib):

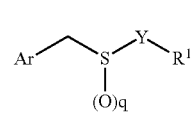

wherein Ar, Y, $R^1$ are as defined in claim 1 and q is 1 or 2; and optionally isolating the formed compound (Ib).

18. A method for preparing a compound of claim 1 comprising the steps of:

a4) reacting a compound C with a compound H to form a compound (Ia):

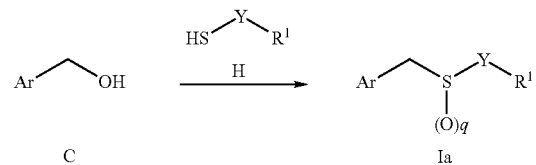

wherein Ar, Y, $R^1$ are as defined in claim 1 and q=0; and optionally b4) isolating the formed compound (Ia); and reacting the compound (Ia) with an appropriate oxidizing agent to form a compound (Ib):

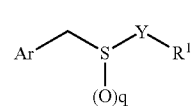

wherein Ar, Y, $R^1$ are as defined in claim 1 and q is 1 or 2; and optionally isolating the formed compound (Ib).

19. A method for preparing a compound of claim 1 comprising the steps of:

a4) reacting a compound B with a compound H to form a compound (Ia):

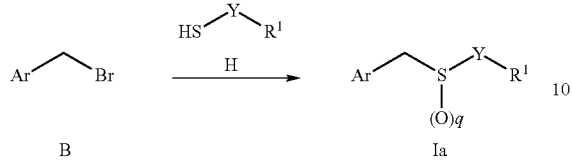

wherein Ar, Y, $R^1$ are as defined in claim 1 and q=0; and optionally b4) isolating the formed compound (Ia); and reacting the compound (Ia) with an appropriate oxidizing agent to form a compound (Ib):

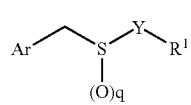

wherein Ar, Y, $R^1$ are as defined in claim 1 and q is 1 or 2; and optionally isolating the formed compound (Ib).

* * * * *